US005739326A

United States Patent [19]

Selby et al.

[11] Patent Number: 5,739,326

[45] Date of Patent: Apr. 14, 1998

[54] HETEROBICYCLIC HERBICIDES

[75] Inventors: Thomas Paul Selby, Wilmington; Michael Peter Winters, New Castle, both of Del.

[73] Assignee: E. I. du Pont de Nemours and Company, Wilmington, Del.

[21] Appl. No.: 759,742

[22] Filed: Dec. 3, 1996

Related U.S. Application Data

[60] Provisional application No. 60/008,581, Dec. 13, 1995.

[51] Int. Cl. $^6$ ...................... C07D 498/04; A61K 31/535

[52] U.S. Cl. ............................ 544/66; 544/236; 544/10; 544/184; 544/11; 544/235; 544/183; 504/236; 504/237; 504/238; 504/222; 504/229; 504/223

[58] Field of Search ............................ 544/66; 504/223

[56] References Cited

U.S. PATENT DOCUMENTS

| | | | |
|---|---|---|---|
| 3,423,409 | 1/1969 | Blatter | 544/183 |
| 4,025,510 | 5/1977 | Elliott | 544/9 |

FOREIGN PATENT DOCUMENTS

| | | |
|---|---|---|
| 555957-A1 | 1/1993 | European Pat. Off. . |
| 634413-A1 | 7/1994 | European Pat. Off. . |

OTHER PUBLICATIONS

Elliott et al., The Rearrangement of Aryl Thiohydrazonates, *Can. J. Chem.*, 53, pp. 1484–1490, 1975.

Vukof et al., J. Chem. Soc., Perk., *Trans.* 1, (2), pp. 192–196, 1977.

Elliott et al., Hydrazides and Thiohydrazides as Sources of Condensed Oxadiazines and Thiadiazines, Including Novel Azo Derivatives Based on Dithizone, *J. Org. Chem.*, 45, pp. 3677–3681, 1980.

Blatter et al., A New Stable Free Radical(1), *Tetrahedron Letters*, 22, pp. 2701–2705, 1968.

Elliott et al., Smiles Rearrangement in Hydrazonyl Systems: *Can. J. Chem.*, 51, pp. 4115–4121, 1973.

*Primary Examiner*—Matthew V. Grumbling
*Assistant Examiner*—King Lit Wong

[57] ABSTRACT

Compounds of Formula I, and their N-oxides and agriculturally-suitable salts, are disclosed which are useful for controlling undesired vegetation

I

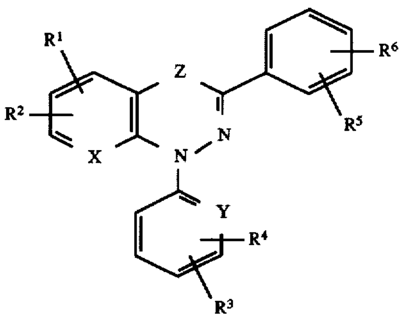

wherein:

X and Y are independently N or CH;

Z is O, $S(O)_n$, $NR^7$, C(=O), C(=S), $C(=N—OR^8)$, $CH(OR^9)$, or $CR^{10}(R^{11})$;

n is 0, 1 or 2; and $R^1$–$R^{11}$ are as defined in the disclosure.

Also disclosed are compositions containing the compounds of Formula I and a method for controlling undesired vegetation which involves contacting the vegetation or its environment with an effective amount of a compound of Formula I.

9 Claims, No Drawings

HETEROBICYCLIC HERBICIDES

CROSS REFERENCE TO RELATED APPLICATIONS

This application claims the benefit of U.S. Provisional Application Ser. No. 60/008,581 filed Dec. 13, 1995.

BACKGROUND OF THE INVENTION

This invention relates to certain heterobicyclic compounds, their N-oxides, agriculturally-suitable salts and compositions, and methods of their use for controlling undesirable vegetation.

The control of undesired vegetation is extremely important in achieving high crop efficiency. Achievement of selective control of the growth of weeds especially in such useful crops as rice, soybean, sugar beet, corn (maize), potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds which are more effective, less costly, environmentally safer or have different modes of action.

SUMMARY OF THE INVENTION

This invention is directed to compounds of Formula I including all geometric and stereoisomers, N-oxides, and agriculturally suitable salts thereof, agricultural compositions containing them and their use for controlling undesirable vegetation:

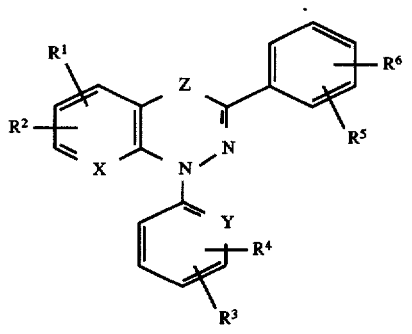

I wherein

X and Y are independently N or CH;

Z is O, $S(O)_n$, $NR^7$, C(=O), C(=S), $C(=N—OR^8)$, $CH(OR^9)$, or $CR^{10}(R^{11})$;

$R^1$ and $R^2$ are independently H, halogen, cyano, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ haloalkylthio, $C_1$–$C_4$ alkylsulfinyl, or $C_1$–$C_4$ alkylsulfonyl;

$R^3$ is halogen, cyano, nitro, $SF_5$, $C_1$–$C_4$ haloalkyl, $C_1$–$C_4$ haloalkoxy, $C_1$–$C_4$ alkylthio, $C_1$–$C_4$ haloalkylthio, $C_1$–$C_4$ alkylsulfinyl, or $C_1$–$C_4$ alkylsulfonyl;

$R^4$ is H, halogen, cyano, nitro, $SF_5$, $C_1$–$C_4$ haloalkyl, $C_1C_4$ haloalkoxy, $C_1$–$C_4$ alkylthio, $C_1$–$C_4$ haloalkylthio, $C_1$–$C_4$ alkylsulfinyl, or $C_1$–$C_4$ alkylsulfonyl; or when $R^3$ and an $R^4$ are attached to adjacent atoms, $R^3$ and $R^4$ can be taken together as $—OCH_2O—$ or $—OCH_2CH_2O—$; each $CH_2$ group of said taken together $R^3$ and $R^4$ optionally substituted with 1–2 fluorine atoms;

$R^5$ and $R^6$ are independently H, 1–2 halogen, cyano, nitro, $SF_5$, $C_1$–$C_4$ alkyl, $C_1$–$C_4$ haloalkyl, $C_1$–$C_4$ alkoxy, $C_1$–$C_4$ haloalkoxy, $C_3$–$C_4$ alkenyloxy, $C_3$–$C_4$ haloalkenyloxy, $C_3$–$C_4$ alkynyloxy, $C_3$–$C_4$ haloalkynyloxy, $C_1$–$C_4$ alkylthio, $C_1$–$C_4$ haloalkylthio, $C_1$–$C_4$ alkylsulfinyl, or $C_1$–$C_4$ alkylsulfonyl;

$R^7$ is H, $C_1$–$C_4$ alkyl, $C_3$–$C_4$ alkenyl, $C_3$–$C_4$ alkynyl, $C_2$–$C_4$ alkylcarbonyl, or $C_2$–$C_4$ alkoxycarbonyl;

$R^8$, $R^9$, $R^{10}$, and $R^{11}$ are independently H or $C_1$–$C_4$ alkyl; and n is 0, 1 or 2.

In the above recitations, the term "alkyl", used either alone or in compound words such as "alkylthio" or "haloalkyl" includes straight-chain or branched alkyl, such as, methyl, ethyl, n-propyl, i-propyl, or the different butyl isomers. "Alkenyl" includes straight-chain or branched alkenes such as 1-propenyl, 2-propenyl, and the different butenyl isomers. "Alkenyl" also includes polyenes such as 1,2-propadienyl. "Alkynyl" includes straight-chain or branched alkynes such as ethynyl, 1-propynyl, 2-propynyl and the different butynyl isomers. "Alkoxy" includes, for example, methoxy, ethoxy, n-propyloxy, isopropyloxy and the different butoxy isomers. "Alkenyloxy" includes straight-chain or branched alkenyloxy moieties. Examples of "alkenyloxy" include $H_2C=CHCH_2O$, $(CH_3)CH=CHCH_2O$ and $CH_2=CHCH_2CH_2O$. "Alkynyloxy" includes straight-chain or branched alkynyloxy moieties. Examples of "alkynyloxy" include $HC≡CCH_2O$ and $CH_3C≡CCH_2O$. "Alkylthio" includes branched or straight-chain alkylthio moieties such as methylthio, ethylthio, and the different propylthio and butylthio isomers. "Alkylsulfinyl" includes both enantiomers of an alkylsulfinyl group Examples of "alkylsulfinyl" include $CH_3S(O)$, $CH_3CH_2S(O)$, $CH_3CH_2CH_2S(O)$, $(CH_3)_2CHS(O)$ and the different butylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and different butylsulfonyl isomers.

The term "halogen", either alone or in compound words such as "haloalkyl", includes fluorine, chlorine, bromine or iodine. The term "1–2 halogen" indicates that one or two of the available positions for that substituent may be halogen. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", and the like, are defined analogously to the term "haloalkyl". Examples of "haloalkenyl" include $(Cl)_2C=CHCH_2$ and $CF_3CH=CHCH_2$. Examples of "haloalkynyl" include $HC≡CCHCl$, $CF_3C≡C$, $CCl_3C≡C$ and $FCH_2C≡CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$.

The total number of carbon atoms in a substituent group is indicated by the "$C_i$–$C_j$" prefix where i and j are numbers from 1 to 4. For example, $C_1$–$C_3$ alkylsulfonyl designates methylsulfonyl through propylsulfonyl. Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$ and $(CH_3)_2CHOC(=O)$. In the above recitations, when a compound of Formula I is comprised of one or more heterocyclic rings, all substituents are attached to these rings through any available carbon or nitrogen by replacement of a hydrogen on said carbon or nitrogen.

When a group contains a substituent which can be hydrogen, for example $R^4$ or $R^8$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, or triethylamine) or inorganic bases (e.g., hydrides, hydroxides, or carbonates of sodium, potassium, lithium, calcium, magnesium or barium) when the compound contains an acidic Preferred compounds for reasons of better activity and/or ease of synthesis are:

Preferred 1. Compounds of Formula I above, and N-oxides and agriculturally-suitable salts thereof, wherein:

X and Y are N;

Z is O or C(=O);

$R^3$ is halogen, $C_1$–$C_4$ haloalkyl, or $C_1$–$C_4$ haloalkoxy;

$R^4$ is H, halogen, $C_1$–$C_4$ haloalkyl, or $C_1$–$C_4$ haloalkoxy; or when $R^3$ and an $R^4$ are attached to adjacent atoms, $R^3$ and $R^4$ can be taken together as —$OCH_2O$— or —$OCH_2CH_2O$—; each $CH_2$ group of said taken together $R^3$ and $R^4$ optionally substituted with 1–2 fluorine atoms.

Preferred 2. Compounds of Preferred 1 wherein $R^1$ and $R^2$ are independently H, halogen, $C_1$–$C_4$ alkyl, $C_1$–$C_4$ haloalkyl, or $C_1$–$C_4$ haloalkoxy; and $R^5$ and $R^6$ are independently H, 1–2 halogen, $C_1$–$C_4$ alkyl, $C_1$–$C_4$ haloalkyl, or $C_1$–$C_4$ haloalkoxy.

Most preferred are compounds of Preferred 2 selected from the group:

a) 3-(4-fluorophenyl)-1-[6-(trifluoromethyl)-2-pyridinyl]-1H-pyrido[2,3-e][1,3,4]oxadiazine;

b) 3-(3,4-difluorophenyl)-6-fluoro-1-[6-(trifluoromethyl)-2-pyridinyl]-1H-pyrido[2,3-e][1,3,4]oxadiazine;

c) 6-fluoro-3-(4-fluorophenyl)-1-[3-(trifluoromethyl)phenyl]-1H-pyrido[2,3-e][1,3,4]oxadiazine;

d) 6-fluoro-3-[2-fluoro-4-(trifluoromethyl)phenyl]-1-[6-(trifluoromethyl)-2-pyridinyl]-1H-pyrido[2,3-e][1,3,4]oxadiazine; and e) 6-fluoro-3-(4-fluorophenyl)-1-[3-(trifluoromethoxy)phenyl]-1H-pyrido[2,3-e][1,3,4]oxadiazine.

This invention also relates to herbicidal compositions comprising herbicidally effective amounts of the compounds of Formula I and at least one of a surfactant, a solid diluent or a liquid diluent. The preferred compositions of the present invention are those which comprise the above preferred compounds.

This invention also relates to a method for controlling undesired vegetation comprising applying to the locus of the vegetation herbicidally effective amounts of the compounds of Formula I (e.g., as a composition described herein). The preferred methods of use are those involving the above preferred compounds.

DETAILS OF THE INVENTION

The compounds of Formula I can be prepared by one or more of the following methods and variations as described in Schemes 1–14. The definitions of X, Y, Z, $R^1$–$R^{11}$ and n in the compounds of Formulae 1–22 below are as defined above in the Summary of the Invention. Compounds of Formulae Ia–Id are various subsets of the compounds of Formula I, and all substituents for Formulae Ia–Id are as defined above for Formula I.

Sulfoxides and sulfones of Formula Ia can be prepared from the thioethers of Formula Ib by oxidation of the sulfur by a variety of methods known in the art (Scheme 1). Typical oxidants are m-chloroperoxybenzoic acid or Oxone® (potassium peroxymonosulfate), but there are many others. For examples in the literature of many of these methods, see: March, J. *Advanced Organic Chemistry*, 4th Ed.; John Wiley & Sons, Inc.: New York, (1992), pp 1201–1203.

Scheme 1

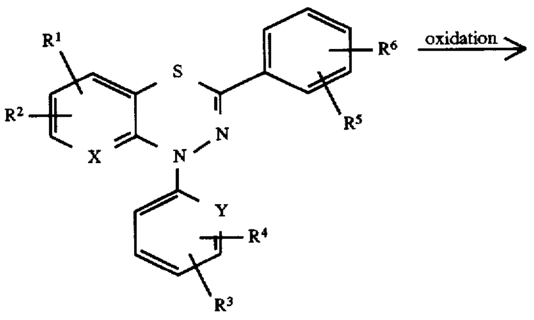

Ib

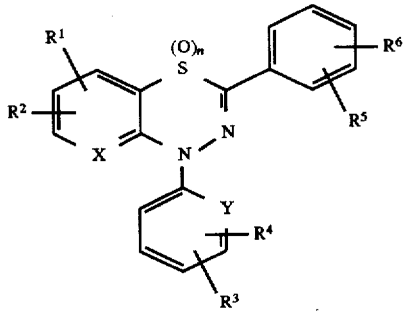

Ia

Scheme 2 illustrates the preparation of compounds of Formula Ic where Z is oxygen or sulfur by the reduction of the nitro group of compounds of Formula 2 to the amine followed by conversion of the amino moiety to hydrogen, fluorine, chlorine, bromine, or iodine. The reduction of an aryl- or pyridinylnitro group to an amine is carried out using methods known in the art: Larock, R. *Comprehensive Organic Transformations*; VCH Publishers, Inc.: New York, (1989), pp 412–415; Boothroyd S., Kerr, M. *Tet. Lett.* (1995), 36, 2411. The amino group can then be reduced to hydrogen by a variety of known methods, most utilizing diazotization followed by introduction of a hydride source. For examples, see: Larock, R. *Comprehensive Organic Transformations*; VCH Publishers, Inc.: New York, (1989), p 25; Cadogan, J., Molina, G. *J. Chem. Soc. Perkin I* (1973), 541. Conversion of the amino group to fluorine, chlorine, bromine or iodine can be readily accomplished by a variety of known methods in the art, most utilizing the same diazonium intermediate: Larock, R. *Comprehensive Organic*

*Transformations*; VCH Publishers, Inc.: New York, (1989), pp 345–346.

Scheme 2

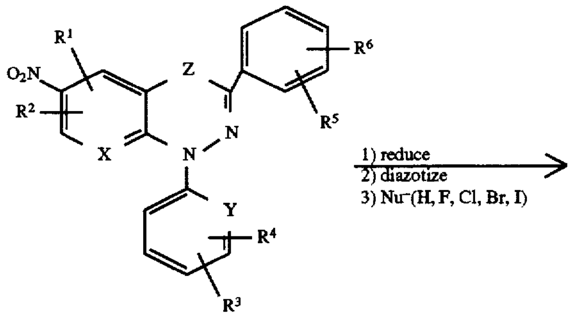

2

Z is O or S

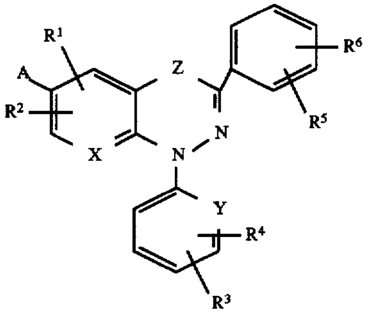

Ic

Z is O or S
A is H, F, Cl, Br, or I

The preparation of compounds of Formula 2 is accomplished by reaction of compounds of Formula 3 with an appropriately substituted 2-chloro-3,5-dinitropyridine or 2,4-dinitrofluorobenzene of Formula 4 and a base (Scheme 3). Examples of this chemistry are described in Elliot, A., Gibson, M. *J. Org. Chem.* (1980), 45, 3677. Typical solvents for these reactions are acetonitrile or dimethylformamide, and typical bases are triethylamine or sodium hydroxide.

Scheme 3

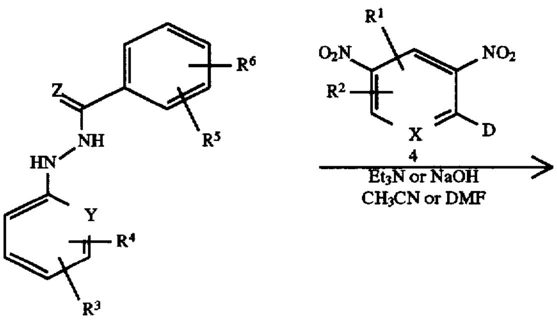

3

Z is O or S

D is Cl or F

-continued
Scheme 3

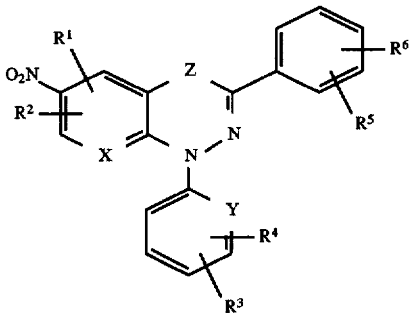

2

Z is O or S

The preparation of hydrazides of Formula 3a can be by addition of an aryl- or pyridylhydrazine of Formula 5 to an aryl acid chloride of Formula 6 in the presence of a nitrogen base such as triethylamine or pyridine (Scheme 4). Examples are well known in the art: Dekeyser, M., McDonald, P. U.S. Pat. No. 5,367,093. Another method involves coupling an aryl- or pyridylhydrazine to an aryl carboxylic acid in the presence of N,N'-dicyclohexylcarbodiimide. See for example: Smith, R., Bates, A., Battisti, A., Byrnes, P., Mroz, C., Smearing, T., Albrecht, F. *J. Org. Chem.* (1968), 33, 851. Other similar methods are known in the literature.

Scheme 4

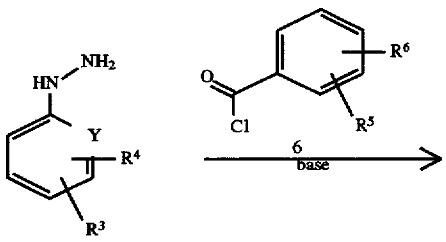

5

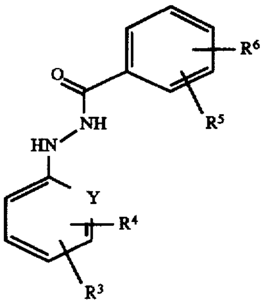

3a

The preparation of thiohydrazides of Formula 3b can be by reaction of an aryl- or pyridylhydrazine of Formula 5 with an S-(thiobenzoyl)thioglycolic acid of Formula 7 in the presence of aqueous sodium hydroxide (Scheme 5). For example, see: Ramarias, S., Srinivasan, P., Ramachandran, J., Sastry, V. *Synthesis*, (1983), 605; Jensen, K., Pedersen, C. *Acta Chem. Scand.* (1961), 15, 1097. These compounds cain also be made from the reaction of compounds of Formula 3a with Lawesson's reagent. For example see: El-Barbary, A., Scheibye, S., Lawesson, S., Fritz, H. *Acta Chem. Scand.* (1980), B34, 597. Another method for the preparation of compounds of Formula 3b is by reaction of a hydrazonyl halide of Formula 8 with hydrogen sulfide in the presence of triethylamine. For example, see: Wolkoff, P., Hammerurn, S. *Acta Chem. Scand.* (1976), B30, 831.

Scheme 5

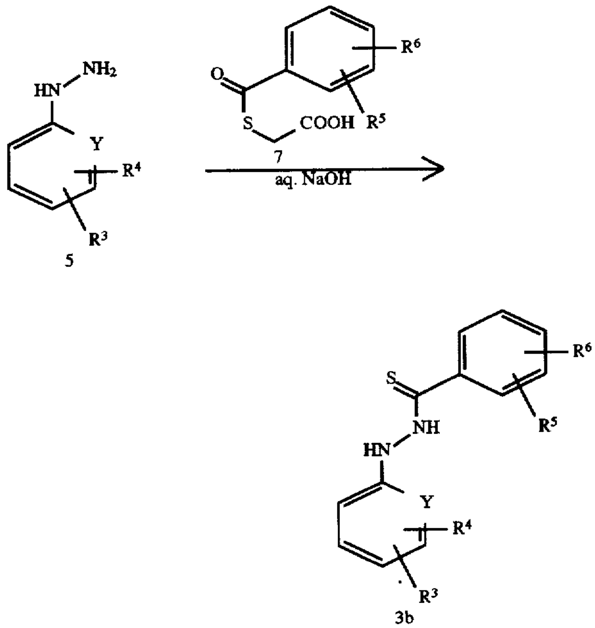

5

7

3b

-continued

Scheme 5

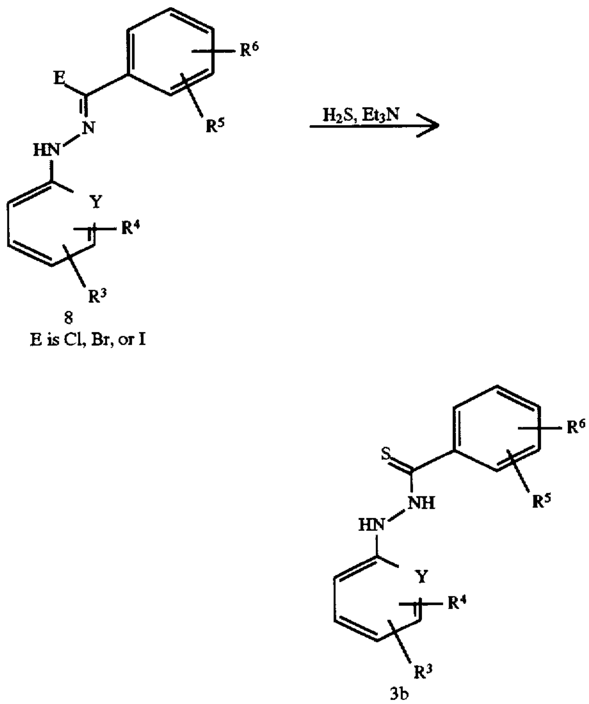

8

E is Cl, Br, or I

3b

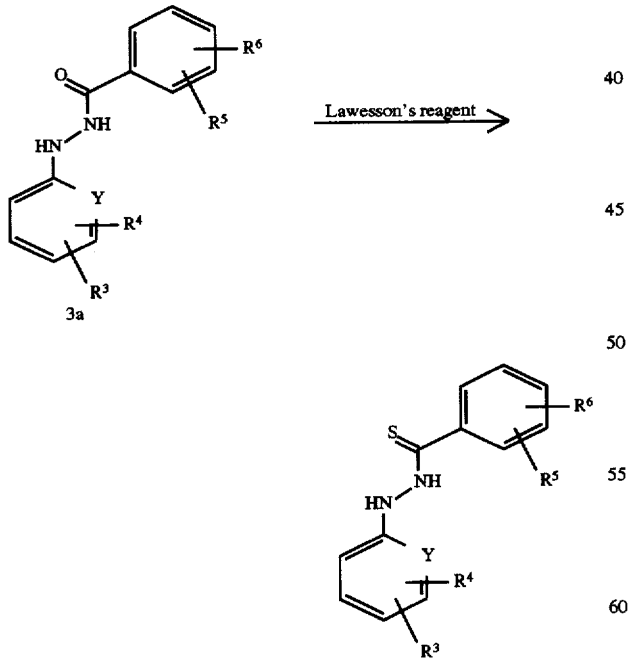

3a

3b

Compounds of Formula Ic can be prepared from compounds of Formula 9 where G is an appropriate leaving group and J is a ketone, cyano or ester group by treatment with a base such as aqueous sodium hydroxide in tetrahydrofuran or potassium carbonate in refluxing 2-butanone (Scheme 6). For example, see: Ames, D., Leung, O., Singh, A. *Synthesis* (1983), 52; Labovitz, J., Fang, L. U.S. Pat. No. 4,729,782.

Scheme 6

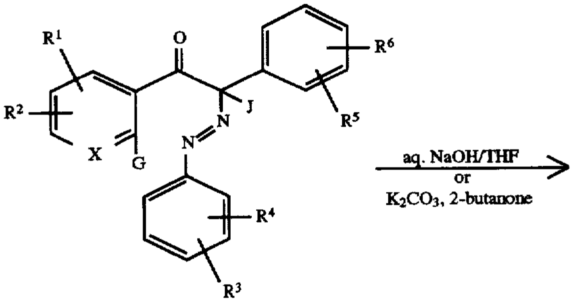

9

G is Cl or F

J is a ketone, an ester or a nitrile

-continued

Scheme 6

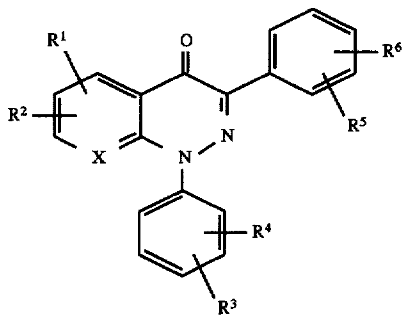

Ic

Compounds of Formula 9 can be prepared from compounds of Formula 10 by treatment with base followed by diazonium salts of Formula 11 (Scheme 7). Examples of related Japp-Klingemann reactions can be found in: Ames, D., Leung, O., Singh, A. *Synthesis* (1983), 52; Labovitz, J., Fang, L. U.S. Pat. No. 4,729,782; Phillips, R. *Org. React.* (1959), 10, 143. When J is an acetyl group, compounds of Formula 9 are isolable, but this is not necessarily the case.

Scheme 7

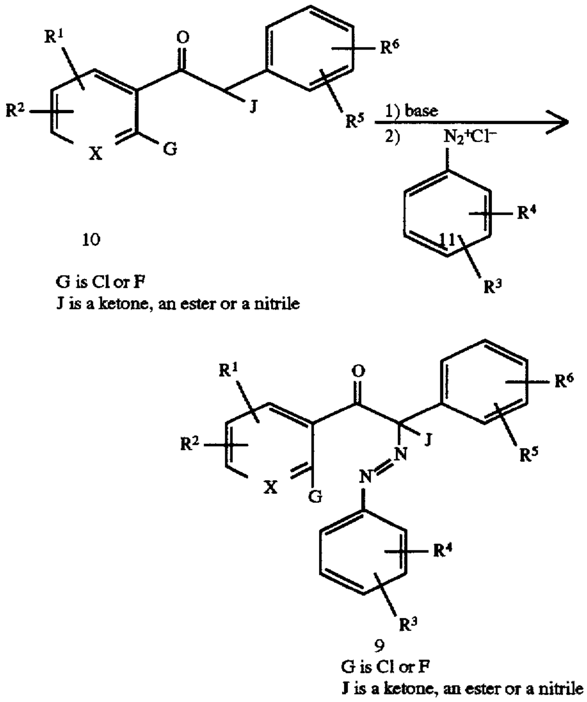

Compounds of Formula 10 can be prepared by a variety of methods (Scheme 8). Reaction of an arylacetic ester of Formula 12 with base to give the enolate followed by quenching with an aryl- or pyridyl acid chloride of Formula 13 gives compounds of Formula 10 where J is an ester. Reaction of an aryl acetone of Formula 12 with base to form the thermodynamic enolate followed by quenching with an aryl- or pyridyl acid chloride of Formula 13 gives compounds of Formula 10 where J is a ketone. For examples of these reactions, see: House, H., Trost, B. *J. Org. Chem.* (1965), 30, 1341; Hauser, C., Swammer, F., Adams, *J. Org. React.* (1954), 8, 59. Other methods involve addition of an enolate of Formula 12 to an aryl- or pyridyl aldehyde of Formula 14 and oxidation of the resulting hydroxyl group to the ketone. Addition of an enolate to an aryl- or pyridyl ester can also give the desired diketone compounds of Formula 10.

Scheme 8

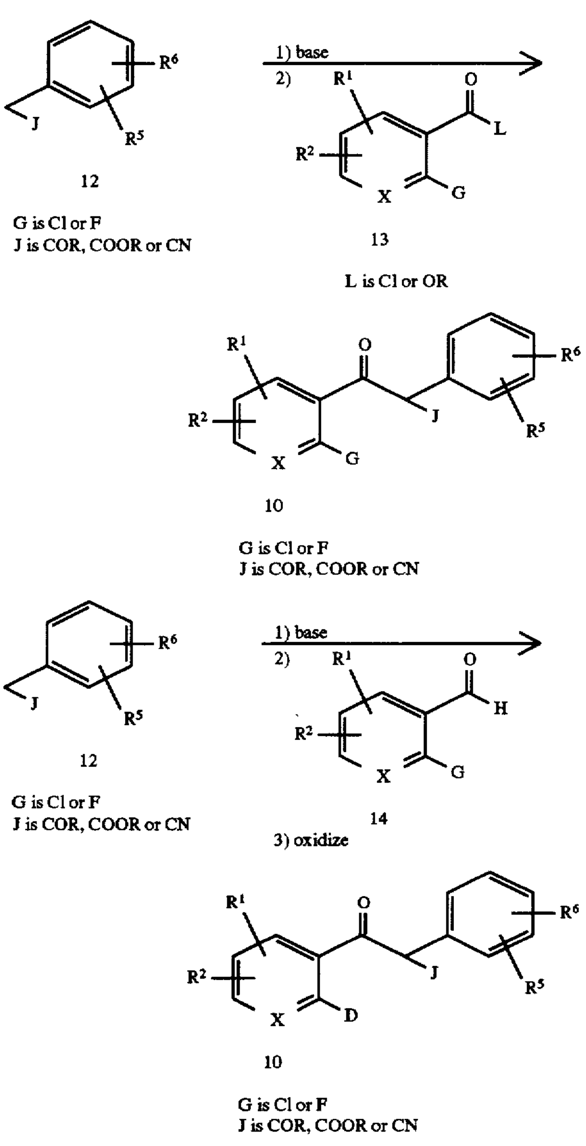

Compounds of Formula Id where Z is $NR^7$, C(=O), C(=S), C(=N—$OR^8$), CH($OR^9$), and $CR^{10}(R^{11})$ can all be formed from the ring-closure of hydrazines of Formula 15 under basic conditions (Scheme 9). Typical bases for the intramolecular ring-closure are aqueous hydroxide and potassium carbonate at temperatures of 20°–100° C. An example of an analogous reaction in the literature can be found in Ames, D., Leung, O., Singh, A. *Synthesis* (1983), 52.

Scheme 9

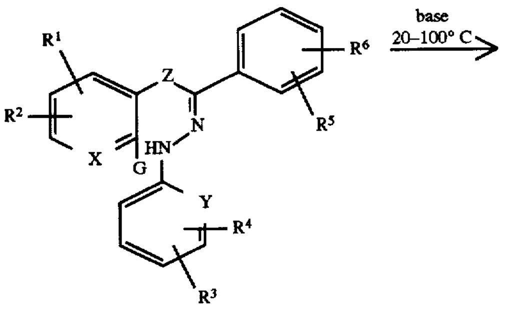

15

Z is $NR^7$, C=O, C=S
C=$NOR^8$, $CHOR^9$, $CR^{10}R^{11}$
G is Cl or F

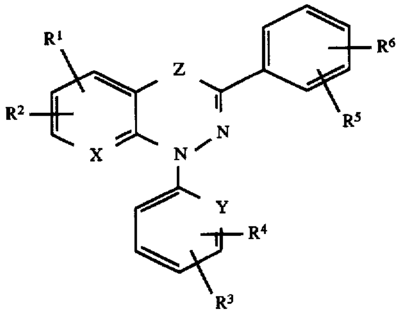

Id

Z is $NR^7$, C=O, C=S,
C=$NOR^8$, $CHOR^9$, $CR^{10}R^{11}$

Compounds of Formula 15a where Z is C(=NZ—$OR^8$) are prepared from the corresponding ketone compound of Formula 15b by treatment with a substituted hydroxylamine (Scheme 10). Examples of this type of reaction are found in *Org. Syn., Coll. Vol. II,* 70 and Hoffman, R., Buntain, G. *Synthesis* (1987), p. 831. Ketone compounds of Formula 15b can in turn be formed by the oxidation of hydroxy compounds of Formula 15c. For examples, see: Larock, R. *Comprehensive Organic Transformations*; VCH Publishers, Inc.: New York, (1989), pp 604–614.

Scheme 10

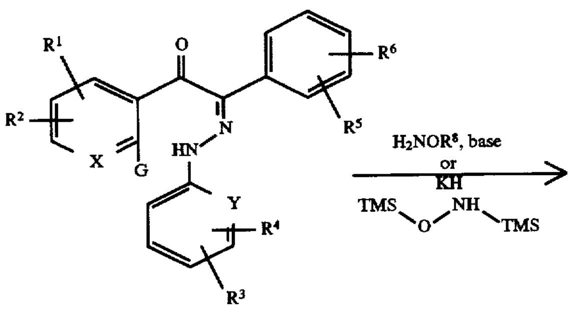

15b

G is Cl or F

-continued
Scheme 10

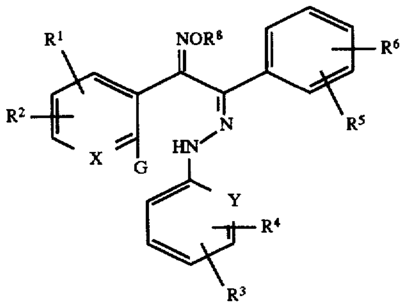

15a

G is Cl or F

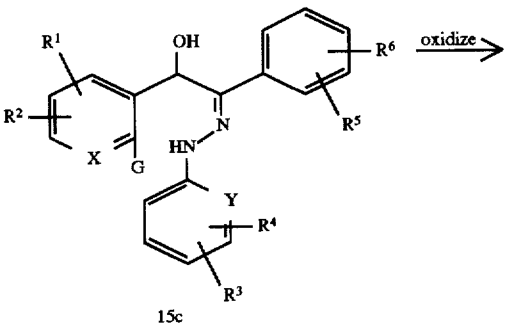

15c

G is Cl or F

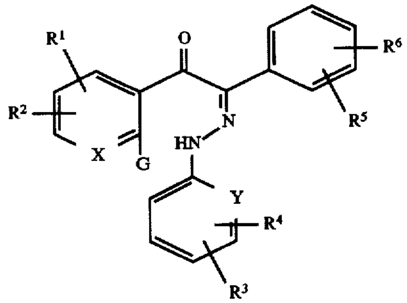

15b

G is Cl or F

Hydrazones of Formula 15d where Z is $NR^7$, $CH(OR^9)$, or $CR^{10}(R^{11})$ can be synthesized from the condensation of ketones of Formula 16 with an aryl- or pyridylhydrazine of Formula 17 (Scheme 11). The formation of hydrazones from ketones is well-known in the art. For example, see: McMurry, J. *J. Am. Chem. Soc.* (1968), 90, 6821. Condensation of amides with hydrazines is not as well known, but there are examples in the literature: Rapoport, H., Bonner, R. J. *Am. Chem. Soc.* (1950), 72, 2783.

Scheme 11

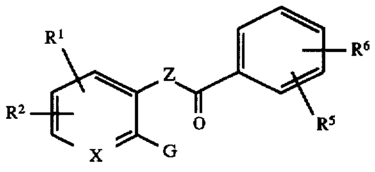

16

Z is $NR^7$, $CHOR^9$, $CR^{10}R^{11}$
G is Cl or F

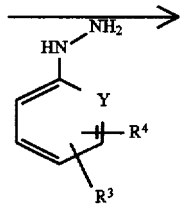

17

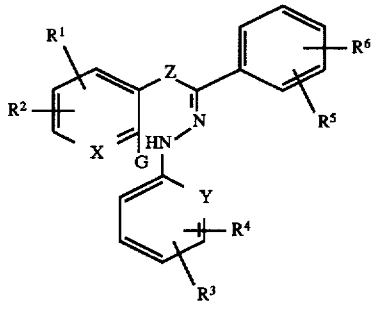

15d

Z is $NR^7$, $CHOR^9$, $CR^{10}R^{11}$
G is Cl or F

α-Hydroxyketones of Formula 16a are available from ketones of Formula 16b by the oxidation of the enolate of compounds of Formula 16b with reagents such as dimethyldioxirane, 3-phenyl-2-(phenylsulfonyl)oxaziridine, or MoOPH (Scheme 12). For examples of these reactions, see: Larock, R. *Comprehensive Organic Transformations*; VCH Publishers, Inc.: New York, (1989), pp 490–491; Guertin, K., Chan, T. *Tel. Lett.*, (1991), 32, 715; Davis, F., Vishwakarma, L., Billmers, J., Finn, J. *J. Org. Chem.* (1984), 49, 3241. α-alkoxyketones of Formula 16c can be prepared from α-hydroxyketones of Formula 16a by treatment with an alkylating agent $R^9M$ and base. For examples, see: Larock, R. *Comprehensive Organic Transformations*; VCH Publishers, Inc.: New York, 1989, pp 445–447. These same enolates can be treated with alkylating agents to form ketones of Formula 16d. For examples of enolate alkylation, see: Larock, R. *Comprehensive Organic Transformations*; VCH Publishers, Inc.: New York, (1989), pp 738–742.

Scheme 12

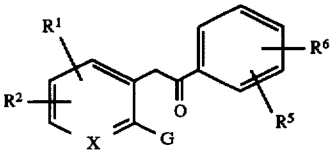

16b

G is Cl or F

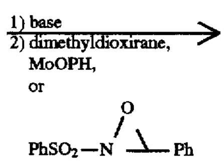

-continued
Scheme 12

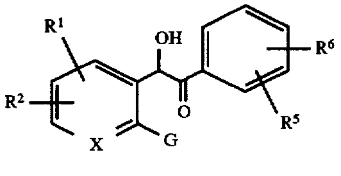

16a

G is Cl or F

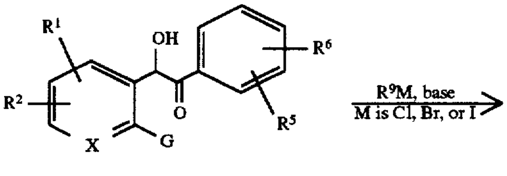

16a

G is Cl or F

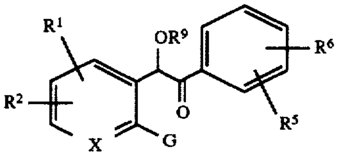

16c

G is Cl or F

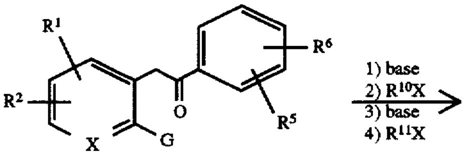

16b

G is Cl or F

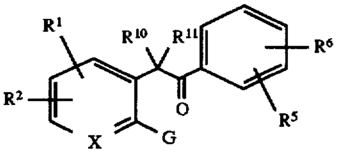

16d

G is Cl or F

Ketones of Formula 16b can be synthesized by a variety of methods known in the literature (Scheme 13). One method utilizes trimethylsilyl cyanohydrins of Formula 18 to add to bromides of Formula 19 (Klose, W., Schwarz, K. *J. Het. Chem.* (1985), 22,669). Another method involves the Pd catalyzed coupling of bromides of Formula 19 to acid chlorides of Formula 20 (Iyoda, M., Sakaitani, M., Otsuka, H., Oda, M. *Tel. Lett.* (1985), 26, 4777; Sato, T., Naruse, K., Enokiya, M., Fujisawa, *T. Chem. Lett.* (1981), 1135). Yet another method uses the anion derived from bromides of Formula 19 to add to acid chlorides or esters of Formula 21 (Kaiser, E., Petty, J. *Synthesis* (1975), 705).

Scheme 13

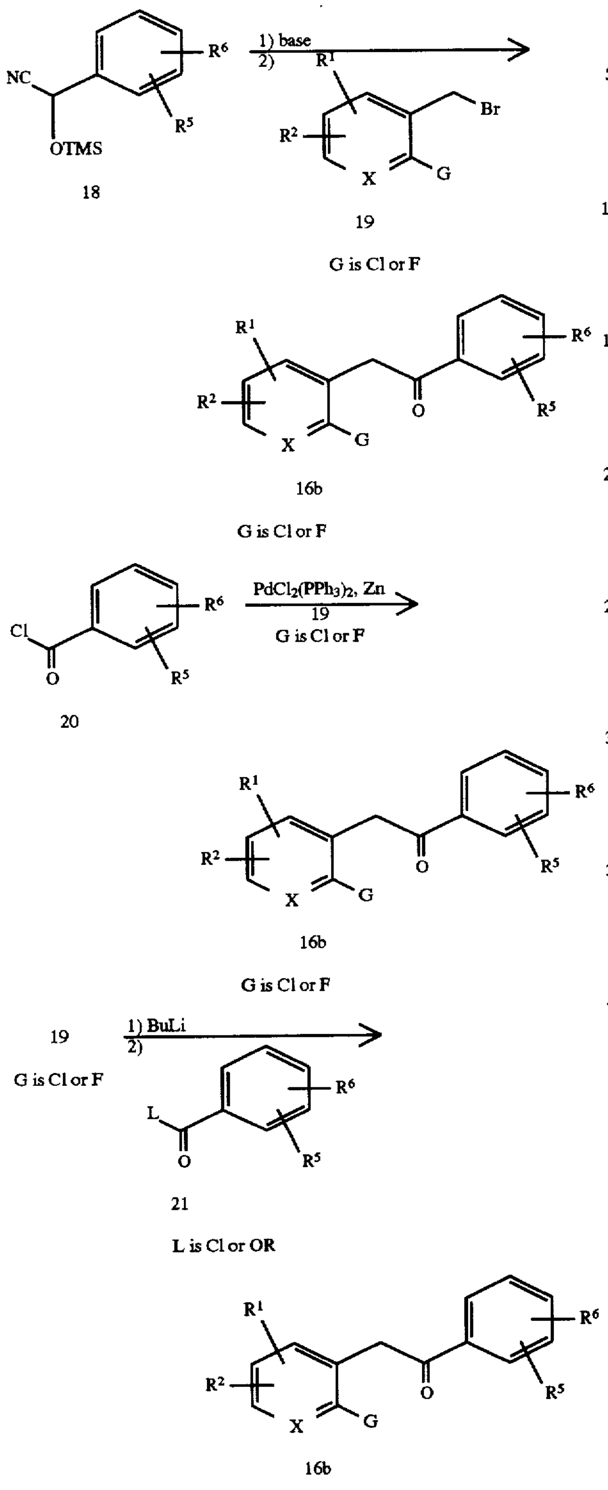

18

19

G is Cl or F

16b

G is Cl or F

20

16b

G is Cl or F

19

G is Cl or F

21

L is Cl or OR

16b

G is Cl or F

Amides of Formula 16e can be synthesized in a variety of ways, the simplest being addition of an amine of Formula 22 to an alkyl halide followed by condensation of the secondary amine with an acid chloride of Formula 20 (Scheme 14). For examples of these reactions, see: *Org. Syn, Coll. Vol. I*, 99;

Larock, R. *Comprehensive Organic Transformations*; VCH Publishers, Inc.: New York, (1989), p 397.

Scheme 14

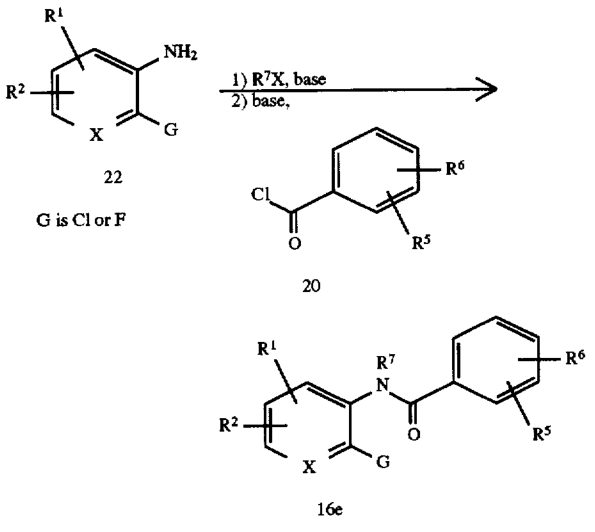

22

G is Cl or F

20

16e

G is Cl or F

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P G. M. *Protective Groups in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1H$ NMR spectra are reported in ppm downfield from tetramethylsilane; s=singlet, d=doublet, t=triplet, m=multiplet, dd=doublet of doublets, br s=broad singlet.

EXAMPLE 1

Step A

4-Fluorobenzoic acid 2-[6-(trifluoromethyl)-2-pyridinyl]hydrazide

To a stirred solution of 6-(trifluoromethyl)pyridin-2-ylhydrazine (3.00 g, 16.4 mmol) and 4-fluorobenzoyl chloride (2.95 g, 18.63 mmol) in anhydrous THF (20 mL) at 0° C. under $N_2$ was added diisopropylethylamine (2.41 g, 18.63 mmol). After 15 min, the solution was allowed to warm to room temperature over 1 h. Water (80 mL) was added, and the aqueous layer was extracted with ethyl acetate (2×100 mL). The organic extracts were combined, washed with water (100 mL), dried over $MgSO_4$, and concentrated in vacuo to a tan solid. Recrystallization from ethyl acetate afforded the title compound of Step A as a white solid (3.16 g). $^1$H NMR ($Me_2SO-d_6$, 400 MHz) δ10.55 (s,1H), 9.10 (s, 1H), 8.00 (m,2H), 7.80 (t, 1H), 7.40 (t,2H), 7.15 (d, 1H), 6.90 (d, 1H).

Step B 3-(4-Fluorophenyl)-6-nitro-1-[6-(trifluoromethyl)-2-pyridinyl]-1H-pyrido[2,3-e][1,3,4]oxadiazine To a stirred suspension of the title compound of Step A (5.14 g, 17.18 mmol) and 2-chloro-3,5-dinitropyridine (4.20 g, 20.61 mmol) in acetonitrile (60 mL) at room temperature under $N_2$ was added triethylamine (23 mL., 171.8 mmol). The dark solution was stirred for 1 h, and then was heated to reflux overnight. After cooling to room temperature, 1N aqueous HCl (80 mL) was added, and the aqueous mixture was extracted with ethyl acetate (2×150 mL). The combined organic layers were washed with water and saturated aqueous NaCl, dried over $MgSO_4$, and concentrated in vacuo to a dark solid (6.5 g). Purification by flash chromatography eluting with 20% ethyl acetate hexanes afforded an orange solid (4.2 g). Trituration with 20% ethyl acetate/hexanes gave the title compound of Step B (3.6 g) as an orange solid melting at 159°–161° C. $^1$H NMR ($CDCl_3$, 400 MHz) δ8.70 (d, 1H), 7.80–8.00 (m,4H), 7.80 (d, 1H), 7.62 (d, 1H), 7.16 (t, 1H).

Step C 3-(4-Fluorophenyl)-1-[6-(trifluoromethyl)-2-pyridinyl]-1H-pyrido[2,3-e][1,3,4]oxadiazin-6-amine A stirred suspension of the title compound of Step B (3.30 g, 7.87 mmol), ferric chloride hexahydrate (27 mg, 0.10 mmol), N,N-dimethylhydrazine (6.0 mL., 78.7 mmol) and charcoal (0.2 g) in methanol (10 mL) was heated to reflux for 1.5 h. When the reaction appeared incomplete by TLC analysis, additional ferric chloride hexahydrate (27 mg) and N,N-dimethylhydrazine (6.0 mL) were added. After 1.5 h, the suspension was allowed to cool to room temperature and filtered through Celite® washed with ethyl acetate. The filtrate was concentrated in vacuo to an oil. Purification by flash chromatography eluting with 50% ethyl acetate/hexanes afforded the title compound of Step C as a yellow solid (2.77 g) melting at 132°–134° C. 1H NMR ($CDCl_3$, 400 MHz) δ7.9–8.0 (m,3H), 7.83 (t, 1H), 7.41 (d, 1H), 7.37 (d, 1H), 7.10 (t,2H), 6.60 (d, 1H) (br s, 2H).

Step D 3-(4-Fluorophenyl)-1-[6-(trifluoromethyl)-2-pyridinyl]-1H-pyrido[2,3-e][1,3,4]oxadiazine To a stirred solution of butyl nitrite (0.69 g, 6.66 mol) in THF (15 mL) at reflux under $N_2$ was added a solution of the title compound of Step C (1.30 g, 3.33 mmol) in THF (15 mL) dropwise over 5 min. The dark brown solution was allowed to reflux 2 h. When TLC analysis was inconclusive, additional butyl nitrite (0.35 g, 3.33 mmol) was added. After 1 h, the solution was allowed to cool to room temperature and concentrated in vacuo to give a purple solid (1.6 g). Purification by flash chromatography eluting with 20–30% ethyl acetate/hexanes afforded the title compound of Step D, a compound of the invention, as a brown solid (0.45 g) melting at 67°–72° C. $^1$H NMR ($CDCl_3$, 300 MHz) δ7.80–8.00 (m,5H), 7.46 (dd, 1H), 7.08–7.16 (m,3H), 6.88 (dd, 1H).

EXAMPLE 2

Step A 1-(2-Chloro-3-pyridinyl)-2-(4-fluorophenyl)-2-[[3-(trifluoromethyl)phenyl]azo]-1,3-butanedione To a stirred solution of (4-fluorophenyl)acetone (1.52 g, 10 mmol) in anhydrous THF (10 mL) at −78° C. under $N_2$ was added lithium diisopropylamide mono(tetrahydrofuran) (5.33 mL of a 1.5M solution in THF, 8 mmol). The solution was allowed to warm to room temperature over 1 h, and then was cooled to −78° C. This solution was then transferred via cannula to a solution of 2-chloronicotinyl chloride (3.50 g, 20 mmol) in anhydrous THF (20 mL) at −78° C. After stirring at −78° C. for 1 h, the solution was poured into 10% $NH_4Cl$ (50 mL), and the aqueous layer extracted with ether (2×80 mL). The combined organic extracts were washed with 5% $NaHCO_3$, dried over $MgSO_4$, and concentrated in vacuo to a brown oil (4.75 g). Prior to the workup above, 3-(trifluoromethyl)diazonium chloride was prepared by addition of concentrated HCl (1 mL) to a suspension of 3-(trifluoromethyl)aniline (1.29 g, 8 mmol) in water (5 mL) followed by addition of acetic acid (0.5 mL for solubility) and sodium nitrite (0.55 g, 8 mmol) at 0° C. To the brown oil (4.75 g) from the reaction above dissolved in ethanol (25 mL) at 0° C. was added potassium hydroxide (1.5 g, 26.7 mmol) in water (10 mL) followed by more water (60 mL). To this solution was added the diazonium salt solution over 2 min. After 5 min, the aqueous solution was extracted with ethyl acetate (2×80 mL). The combined organic extracts were dried over $MgSO_4$ and concentrated in vacuo to a brown oil. Purification by flash chromatography eluting with 15–20% ethyl acetate/hexanes afforded the title compound of Step A as a brown oil (1.27 g) which was somewhat impure by $^1$H NMR. $^1$H NMR ($CDCl_3$, 400 MHz) δ8.35 (m, 1H), 7.90 (s,1H), 7.80 (m,2H), 7.64 (t, 1H), 7.53 (m,2H), 7.43 (m, 1H), 7.20 (m,3H), 2.15 (s,3H).

Step B 3-(4-Fluorophenyl)-1-[3-(trifluoromethyl)phenyl]pyrido[2,3-c]pyridazin-4(1H)-one To a stirred solution of the title compound of Step A (1.20 g, 2.59 mmol) in THF (30 mL) at room temperature was added 1N NaOH. After 2 h, the solution was extracted with ethyl acetate (2×100 mL). The combined organic extracts were washed with water (100 mL) and saturated aqueous NaCl (80 mL), dried over $MgSO_4$, and concentrated in vacuo to a yellow solid (1.19 g). Purification by trituration with petroleum ether afforded the title compound of Step B, a compound of the invention, as a yellow solid (0.64 g) melting at 165°–167° C. $^1$H NMR ($CDCl_3$, 400 MHz) δ8.77 (m,2H), 8.22 (m,2H), 7.98 (s,1H), 7.90 (d, 1H), 7.68–7.77 (m,2H), 7.47 (dd, 1H), 7.16 (t,2H).

EXAMPLE 3

Step A

2-Chloro-3-pyridinemethanol

To a stirred solution of 2-chloronicotinic acid (10.0 g, 63.4 mmol) in anhydrous THF (150 mL) at 0° C. under $N_2$ was added lithium aluminum hydride (63 mL of a 1.0M solution in THF, 63 mmol) over 10 minutes. The solution was allowed to warm to room temperature over 2 h. Small quantities of ice were carefully added to quench the reaction followed by water. The aqueous solution was extracted with ether. The combined organic extracts were washed with water and saturated aqueous NaCl, dried over $MgSO_4$, and concentrated in vacuo to give the title compound of Step A as an orange solid (6.18 g). $^1H$ NMR ($CDCl_3$, 300 MHz) δ8.30 (dd, 1H), 7.90 (dd, 1H), 7.29 (dd, 1H), 4.80 (s,2H), 2.42 (br s,1H).

Step B

3-Bromomethyl-2-chloropyridine

To a stirred solution of the title compound of Step A (5.50 g, 38.3 mmol) in $CH_2Cl_2$ (60 mL) at 0° C. under $N_2$ was added phosphorus tribromide (3.60 mL, 38.3 mmol). The solution was allowed to warm to room temperature overnight. The solution was poured into ice water and the aqueous layer was extracted with $CHCl_3$. The combined organic extracts were washed with water, 5% $NaHCO_3$, and saturated aqueous NACl, dried over $MgSO_4$ and concentrated in vacuo to a yellow oil. Purification by flash chromatography during with 20% ethyl acetate/hexanes afforded the title compound of Step B as a white solid (5.06 g). $^1H$ NMR ($CDCl_3$, 300 MHz) δ8.34 (dd, 1H), 7.80 (dd,1H), 7.26 (dd, 1H), 4.56 (s,2H).

Step C 2-(2-Chloro-3-pyridinyl)-1-(4-fluorophenyl)ethanone

To a stirred suspension of 4-fluorobenzoyl chloride (2.89 mL, 24.5 mmol), bis(triphenylphosphine)palladium (II) chloride (1.08 g, 1.54 mmol) and zinc dust (3.20 g, 49 mmol) in anhydrous dimethoxyethane (50 mL) was added a solution of the title compound of Step B (5.06 g, 24.5 mmol) in dimethoxyethane (50 mL) at room temperature under $N_2$ over 45 min. After 20 h, the suspension was filtered through Celite® washed with ethyl acetate. The filtrate was washed with water and saturated aqueous NaCl, dried over $MgSO_4$, and concentrated in vacuo to a yellow solid. Purification by flash chromatography eluting with 17–60% ethyl acetate/hexanes afforded the title compound of Step C as a yellow solid (0.77 g) which was somewhat impure by $^1H$ NMR. $^1H$ NMR ($CDCl_3$, 300 MHz) δ8.30 (dd, 1H), 8.10 (m,2H), 7.6 (dd, 1H), 7.0–7.4 (m,3H), 4.40 (s,2H).

Step D 2-(2-Chloro-3-pyridinyl)-1-(4-fluorophenyl)-2-hydroxyethanone

To a stirred solution of the title compound of Step C (0.73 g, 2.92 mmol) in anhydrous THF (10 mL) at −78° C. under $N_2$ was added potassium bis(trimethylsilyl)amide (6.43 mL of a 0.5M solution in toluene, 3.22 mmol). After 10 min, a solution of 3-phenyl-2-(phenylsulfonyl)oxaziridine (1.14 g, 4.38 mmol) in THF (10 mL) was added via syringe causing the brown solution to turn yellow. After 20 min, 10% aqueous $NH_4Cl$ was added and the aqueous layer was extracted with ether (2×60 mL). The combined organic extracts were dried over $MgSO_4$ and concentrated in vacuo to an oily solid. This solid was triturated with hexanes and filtered off. Purification of the filtrate by column chromatography eluting with 4–25% ethyl acetate/hexanes afforded the title compound of Step D as a colorless oil (0.29 g). $^1H$ NMR ($CDCl_3$, 300 MHz) δ8.36 (dd, 1H), 7.9–8.1 (m,2H), 7.51 (m, 1H), 7.22 (m, 1H), 7.05–7.18 (m,2H), 6.32 (m, 1H), 4.21 (br s, 1H). $APCI^+$ found 266 (M+1); calc 265 (M).

Step E 2-(2-Chloro-3-pyridinyl)-1-(4-fluorophenyl)-2-hydroxyethanone[6-(trifluoromethyl)-2-pyridinyl] hydrazone A stirred solution of the title compound of Step D (0.29 g, 1.09 mmol) and 6-(trifluoromethyl)pyridin-2-yl hydrazine (213 mg, 1.20 mmol) in toluene (10 mL) was heated to reflux for 1 h. The solution was cooled to room temperature, water was added, and the aqueous layer was extracted with ethyl acetate. The combined organic extracts were dried over $MgSO_4$ and concentrated in vacuo to a yellow oil (0.47 g). Purification by flash chromatography eluting with 20–60% ethyl acetate/hexanes afforded the title compound of Step E as a yellow oil (0.29 g) which was slightly impure by $^1H$ NMR. $^1H$ NMR ($CDCl_3$, 300 MHz) δ8.30 (dd, 1H), 8.20 (s, 1H), 7.80 (dd, 1H), 7.70 (t, 1H), 7.35 (d, 1H), 7.25 (m, 1H), 7.00–7.20 (m,5H), 5.93 (d, 1 H), 4.20 (d,1H). $APCI^+$ found 425 (M+1), calc 424 (M). $APCI^-$ found 423 (M−1).

Step F (2-Chloro-3-pyridinyl)(4-fluorophenyl)ethanedione 2-[6-(trifluoromethyl)-2-pyridinyl]hydrazone To a stirred suspension of the title compound of Step E (270 mg, 0.64 mmol) and powdered 4A molecular sieves (about 1.0 g) in $CH_2Cl_2$ (40 mL) was added pyridinium chlorochromate (206 mg, 0.95 mmol). After 3 h, ether (40 mL) was added and the suspension was filtered through silica gel with ethyl acetate. After concentration in vacuo, purification by flash chromatography eluting with 20% ethyl acetate/hexanes afforded the title compound of Step F as a yellow oil (80 mg). $^1H$ NMR ($CDCl_3$, 300 MHz) δ8.91 (s, 1H), 8.57 (dd, 1H), 7.82 (dd, 1H), 7.69 (t, 1H), 7.20–7.50 (m,6H), 7.00 (d, 1H).

Step G 3-(4-Fluorophenyl)-1-[6-(trifluoromethyl)-2-pyridinyl]pyrido[2,3-c]pyridazin-4(1H)-one To a solution of the title compound of Step F (80 mg, 0.19 mmol) in THF (10 mL) was added 1M NaOH (10 mL). After stirring at room temperature overnight, the reaction was not complete. The solution was heated to reflux for 1 h, and then was cooled to room temperature. Water was added, and the aqueous layer was extracted with ether. The combined organic extracts were washed with saturated aqueous NaCl, dried over $MgSO_4$, and concentrated in vacuo to give the title compound of Step G, a compound of the invention, as a yellow solid (70 mg) melting at 192°–196° C. $^1H$ NMR ($CDCl_3$, 400 MHz) δ8.72 (m,2H), 8.19 (m,3H), 7.87 (d,2H), 7.47 (dd,1H), 7.15 (t,2H).

By the procedures described herein together with methods known in the art, the following compounds of Tables 1 to 46 can be prepared. The following abbreviations are used in the Tables which follow: t=tertiary, s=secondary, n=normal, i=iso, Me=methyl, Et=ethyl, Pr=propyl, i-Pr=isopropyl, Bu=butyl, OMe=methoxy, SEt=ethylthio, CN=cyano, $NO_2$=nitro, MeS(O)=methylsulfinyl, and $MeS(O)_2$=methylsulfonyl.

Key Structure for Tables 1–46

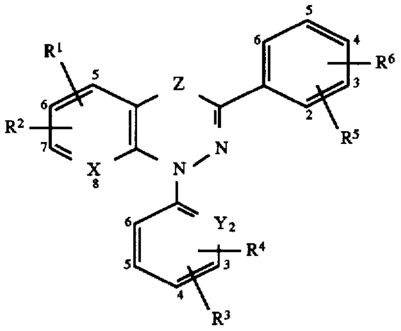

I

TABLE 1

Compounds of Formula I wherein Z = O, X = CH, Y = CH, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 2

Compounds of Formula I wherein Z = O, X = CH, Y = N, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 3

Compounds of Formula I wherein Z = O, X = N, Y = CH, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |

TABLE 3-continued

Compounds of Formula I wherein Z = O, X = N, Y = CH, $R^2 = R^4 = R^6$ = H and

| $R^1$ | $R^3$ | $R^5$ | $R^1$ | $R^3$ | $R^5$ |
|---|---|---|---|---|---|
| H | 3-CN | 2-Cl | 5-SEt | 3-$NO_2$ | 4-$NO_2$ |

TABLE 4

Compounds of Formula I wherein Z = O, X = N, Y = N, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |
| H | 3-$CF_3CF_2$ | 4-F | 6-F | 3-$CF_3$ | 4-F |
| H | 3-$SF_5$ | 4-Cl | 6-F | 3-$CF_3$ | 4-Cl |
| H | 3-MeS(O) | 4-F | 6-Cl | 3-$CF_3$ | 4-F |
| H | 3-MeS$(O)_2$ | 4-Cl | 6-Cl | 3-$CF_3$ | 4-Cl |
| H | 3-F | 4-F | 6-Br | 3-$CF_3$ | 4-F |
| H | 3-I | 4-Cl | 6-Br | 3-$CF_3$ | 4-Cl |
| H | 3-Br | 4-F | 6-I | 3-$CF_3$ | 4-F |
| H | 3-Cl | 4-Cl | 6-I | 3-$CF_3$ | 4-Cl |
| H | 3-$CF_3O$ | 4-F | 7-Me | 3-$CF_3$ | 4-F |
| H | 4-$SF_5$ | 4-Cl | 7-Cl | 3-$CF_3$ | 4-Cl |
| H | 5-SEt | 4-F | 7-OMe | 3-$CF_3$ | 4-F |
| H | 3-$NO_2$ | 4-Cl | 5-SEt | 3-$CF_3$ | 4-Cl |
| H | 3-$CF_3O$ | 4-F | 6-F | 3-$CF_3O$ | 4-F |
| H | 3-$CF_3O$ | 4-Cl | 6-F | 3-$CF_3O$ | 4-Cl |
| H | 3-$HCF_2O$ | 4-F | 6-Cl | 3-$HCF_2O$ | 4-F |
| H | 3-$HCF_2O$ | 4-Cl | 6-Cl | 3-$HCF_2O$ | 4-Cl |

TABLE 5

Compounds of Formula I wherein Z = S, X = CH, Y = CH, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 6

Compounds of Formula I wherein Z = S, X = CH, Y = N, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |

TABLE 6-continued

Compounds of Formula I wherein Z = S, X = CH, Y = N, $R^2 = R^4 = R^6 = H$ and

| $R^1$ | $R^3$ | $R^5$ | $R^1$ | $R^3$ | $R^5$ |
|---|---|---|---|---|---|
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 7

Compounds of Formula I wherein Z = S, X = N, Y = CH, $R^2 = R^4 = R^6 = H$ and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 8

Compounds of Formula I wherein Z = S, X = N, Y = N, $R^2 = R^4 = R^6 = H$ and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |
| H | 3-$CF_3CF_2$ | 4-F | 6-F | 3-$CF_3$ | 4-F |
| H | 3-$SF_5$ | 4-Cl | 6-F | 3-$CF_3$ | 4-Cl |
| H | 3-MeS(O) | 4-F | 6-Cl | 3-$CF_3$ | 4-F |
| H | 3-MeS$(O)_2$ | 4-Cl | 6-Cl | 3-$CF_3$ | 4-Cl |
| H | 3-F | 4-F | 6-Br | 3-$CF_3$ | 4-F |
| H | 3-I | 4-Cl | 6-Br | 3-$CF_3$ | 4-Cl |
| H | 3-Br | 4-F | 6-I | 3-$CF_3$ | 4-F |
| H | 3-Cl | 4-Cl | 6-I | 3-$CF_3$ | 4-Cl |
| H | 3-$CF_3O$ | 4-F | 7-Me | 3-$CF_3$ | 4-F |
| H | 4-$SF_5$ | 4-Cl | 7-Cl | 3-$CF_3$ | 4-Cl |
| H | 5-SEt | 4-F | 7-OMe | 3-$CF_3$ | 4-F |
| H | 3-$NO_2$ | 4-Cl | 5-SEt | 3-$CF_3$ | 4-Cl |
| H | 3-$CF_3O$ | 4-F | 6-F | 3-$CF_3O$ | 4-F |
| H | 3-$CF_3O$ | 4-Cl | 6-F | 3-$CF_3O$ | 4-Cl |

TABLE 8-continued

Compounds of Formula I wherein Z = S, X = N, Y = N, $R^2 = R^4 = R^6 = H$ and

| $R^1$ | $R^3$ | $R^5$ | $R^1$ | $R^3$ | $R^5$ |
|---|---|---|---|---|---|
| H | 3-$HCF_2O$ | 4-F | 6-Cl | 3-$HCF_2O$ | 4-F |
| H | 3-$HCF_2O$ | 4-Cl | 6-Cl | 3-$HCF_2O$ | 4-Cl |

TABLE 9

Compounds of Formula I wherein Z = S(O), X = CH, Y = CH, $R^2 = R^4 = R^6 = H$ and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 10

Compounds of Formula I wherein Z = S(O), X = CH, Y = N, $R^2 = R^4 = R^6 = H$ and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 11

Compounds of Formula I wherein Z = S(O), X = N, Y = CH, $R^2 = R^4 = R^6 = H$ and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 12

Compounds of Formula I wherein Z = S(O), X = N, Y = N, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |
| H | 3-$CF_3CF_2$ | 4-F | 6-F | 3-$CF_3$ | 4-F |
| H | 3-$SF_5$ | 4-Cl | 6-F | 3-$CF_3$ | 4-Cl |
| H | 3-MeS(O) | 4-F | 6-Cl | 3-$CF_3$ | 4-F |
| H | 3-MeS$(O)_2$ | 4-Cl | 6-Cl | 3-$CF_3$ | 4-Cl |
| H | 3-F | 4-F | 6-Br | 3-$CF_3$ | 4-F |
| H | 3-I | 4-Cl | 6-Br | 3-$CF_3$ | 4-Cl |
| H | 3-Br | 4-F | 6-I | 3-$CF_3$ | 4-F |
| H | 3-Cl | 4-Cl | 6-I | 3-$CF_3$ | 4-Cl |
| H | 3-$CF_3O$ | 4-F | 7-Me | 3-$CF_3$ | 4-F |
| H | 4-$SF_5$ | 4-Cl | 7-Cl | 3-$CF_3$ | 4-Cl |
| H | 5-SEt | 4-F | 7-OMe | 3-$CF_3$ | 4-F |
| H | 3-$NO_2$ | 4-Cl | 5-SEt | 3-$CF_3$ | 4-Cl |
| H | 3-$CF_3O$ | 4-F | 6-F | 3-$CF_3O$ | 4-F |
| H | 3-$CF_3O$ | 4-Cl | 6-F | 3-$CF_3O$ | 4-Cl |
| H | 3-$HCF_2O$ | 4-F | 6-Cl | 3-$HCF_2O$ | 4-F |
| H | 3-$HCF_2O$ | 4-Cl | 6-Cl | 3-$HCF_2O$ | 4-Cl |

TABLE 13

Compounds of Formula I wherein Z = $S(O)_2$, X = CH, Y = CH, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 14

Compounds of Formula I wherein Z = $S(O)_2$, X = CH, Y = N, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 15

Compounds of Formula I wherein Z = $S(O)_2$, X = N, Y = CH, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 16

Compounds of Formula I wherein Z = $S(O)_2$, X = N, Y = N, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |
| H | 3-$CF_3CF_2$ | 4-F | 6-F | 3-$CF_3$ | 4-F |
| H | 3-$SF_5$ | 4-Cl | 6-F | 3-$CF_3$ | 4-Cl |
| H | 3-MeS(O) | 4-F | 6-Cl | 3-$CF_3$ | 4-F |
| H | 3-MeS$(O)_2$ | 4-Cl | 6-Cl | 3-$CF_3$ | 4-Cl |
| H | 3-F | 4-F | 6-Br | 3-$CF_3$ | 4-F |
| H | 3-I | 4-Cl | 6-Br | 3-$CF_3$ | 4-Cl |
| H | 3-Br | 4-F | 6-I | 3-$CF_3$ | 4-F |
| H | 3-Cl | 4-Cl | 6-I | 3-$CF_3$ | 4-Cl |
| H | 3-$CF_3O$ | 4-F | 7-Me | 3-$CF_3$ | 4-F |
| H | 4-$SF_5$ | 4-Cl | 7-Cl | 3-$CF_3$ | 4-Cl |
| H | 5-SEt | 4-F | 7-OMe | 3-$CF_3$ | 4-F |
| H | 3-$NO_2$ | 4-Cl | 5-SEt | 3-$CF_3$ | 4-Cl |
| H | 3-$CF_3O$ | 4-F | 6-F | 3-$CF_3O$ | 4-F |
| H | 3-$CF_3O$ | 4-Cl | 6-F | 3-$CF_3O$ | 4-Cl |
| H | 3-$HCF_2O$ | 4-F | 6-Cl | 3-$HCF_2O$ | 4-F |
| H | 3-$HCF_2O$ | 4-Cl | 6-Cl | 3-$HCF_2O$ | 4-Cl |

TABLE 17

Compounds of Formula I wherein Z = C(═O), X = CH, Y = CH, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 18

Compounds of Formula I wherein Z = C(═O), X = CH, Y = N, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 19

Compounds of Formula I wherein Z = C(═O), X = N, Y = CH, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 20

Compounds of Formula I wherein Z = C(═O), X = N, Y = N, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |
| H | 3-$CF_3CF_2$ | 4-F | 6-F | 3-$CF_3$ | 4-F |
| H | 3-$SF_5$ | 4-Cl | 6-F | 3-$CF_3$ | 4-Cl |
| H | 3-MeS(O) | 4-F | &Cl | 3-$CF_3$ | 4-F |
| H | 3-MeS$(O)_2$ | 4-Cl | 6-Cl | 3-$CF_3$ | 4-Cl |
| H | 3-F | 4-F | 6-Br | 3-$CF_3$ | 4-F |
| H | 3-I | 4-Cl | 6-Br | 3-$CF_3$ | 4-Cl |
| H | 3-Br | 4-F | 6-I | 3-$CF_3$ | 4-F |
| H | 3-Cl | 4-Cl | 6-I | 3-$CF_3$ | 4-Cl |
| H | 3-$CF_3O$ | 4-F | 7-Me | 3-$CF_3$ | 4-F |
| H | 4-$SF_5$ | 4-Cl | 7-Cl | 3-$CF_3$ | 4-Cl |
| H | 5-SEt | 4-F | 7-OMe | 3-$CF_3$ | 4-F |
| H | 3-$NO_2$ | 4-Cl | 5-SEt | 3-$CF_3$ | 4-Cl |
| H | 3-$CF_3O$ | 4-F | 6-F | 3-$CF_3O$ | 4-F |
| H | 3-$CF_3O$ | 4-Cl | 6-F | 3-$CF_3O$ | 4-Cl |

TABLE 20-continued

Compounds of Formula I wherein Z = C(═O), X = N, Y = N, $R^2 = R^4 = R^6$ = H and

| $R^1$ | $R^3$ | $R^5$ | $R^1$ | $R^3$ | $R^5$ |
|---|---|---|---|---|---|
| H | 3-$HCF_2O$ | 4-F | 6-Cl | 3-$HCF_2O$ | 4-F |
| H | 3-$HCF_2O$ | 4-Cl | 6-Cl | 3-$HCF_2O$ | 4-Cl |

TABLE 21

Compounds of Formula I wherein Z = C(═S), X = CH, Y = CH, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 22

Compounds of Formula I wherein Z = C(═S), X = CH, Y = N, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 23

Compounds of Formula I wherein Z = C(═S), X = N, Y = N, $R^2 = R^4 = R^6$ = H and

| $R^1$ | $R^3$ | $R^5$ | $R^1$ | $R^3$ | $R^5$ |
|---|---|---|---|---|---|
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 24

| Compounds of Formula I wherein Z = C(=S), X = N, Y = N, $R^2 = R^4 = R^6$ = H and | | | | | |
|---|---|---|---|---|---|
| $R^1$ | $R^3$ | $R^5$ | $R^1$ | $R^3$ | $R^5$ |
| H | 3-$CF_3$ | 4-F | 6-F | 3-$CF_3CF_2$ | 4-F |
| H | 3-$CF_3$ | 4-Cl | 6-F | 3-$SF_5$ | 4-F |
| H | 3-$CF_3$ | 2-F, 4-F | 6-Cl | 3-MeS(O) | 4-CN |
| H | 3-$CF_3$ | 4-$CF_3$ | 6-Cl | 3-MeS$(O)_2$ | 4-$CF_3CF_2$ |
| H | 3-$CF_3$ | 4-Br | 6-Br | 3-F | 4-$SF_5$ |
| H | 3-$CF_3$ | 4-CN | 6-Br | 3-I | H |
| H | 3-$CF_3$ | 4-$NO_2$ | 6-I | 3-Br | 2-Me |

TABLE 24-continued

| Compounds of Formula I wherein Z = C(=S), X = N, Y = N, $R^2 = R^4 = R^6$ = H and | | | | | |
|---|---|---|---|---|---|
| $R^1$ | $R^3$ | $R^5$ | $R^1$ | $R^3$ | $R^5$ |
| H | 3-$CF_3$ | 4-I | 6-I | 3-Cl | 3-OMe |
| H | 3-$CF_3$ | 4-MeS(O) | 7-Me | 3-$CF_3O$ | 3-SEt |
| H | 3-$CF_3$ | 4-MeS$(O)_2$ | 7-Cl | 4-$SF_5$ | 4-$CF_3O$ |
| H | 6-CN | 2-F | 7-OMe | 5-SEt | H |
| H | 3-CN | 2-Cl | 5-SEt | 3-$NO_2$ | 4-$NO_2$ |

TABLE 25

| Compounds of Formula I wherein Z = $NR^7$, X = CH, $R^2 = R^4 = R^6$ = H and | | | | | | | |
|---|---|---|---|---|---|---|---|
| $R^1$ | $R^3$ | $R^5$ | $R^7$ | $R^1$ | $R^3$ | $R^5$ | $R^7$ |
| H | 3-$CF_3$ | 4-F | H | 6-F | 3-$CF_3C_2$ | 4-F | propargyl |
| H | 3-$CF_3$ | 4-Cl | H | 6-F | 3-$SF_5$ | 4-F | propargyl |
| H | 3-$CF_3$ | 2-F, 4-F | H | 6-Cl | 3-MeS(O) | 4-CN | propargyl |
| H | 3-$CF_3$ | 4-$CF_3$ | H | 6-Cl | 3-MeS$(O)_2$ | 4-$CF_3CF_2$ | propargyl |
| H | 3-$CF_3$ | 4-Br | Me | 6-Br | 3-F | 4-$SF_5$ | EtC(O) |
| H | 3-$CF_3$ | 4-CN | Me | 6-Br | 3-I | H | EtC(O) |
| H | 3-$CF_3$ | 4-$NO_2$ | Me | 6-I | 3-Br | 2-Me | EtC(O) |
| H | 3-$CF_3$ | 4-I | Me | 6-I | 3-Cl | 3-OMe | EtC(O) |
| H | 3-$CF_3$ | 4-MeS(O) | allyl | 7-Me | 3-$CF_3O$ | 3-SEt | MeOC(O) |
| H | 3-$CF_3$ | 4-MeS$(O)_2$ | allyl | 7-Cl | 4-$SF_5$ | 4-$CF_3O$ | MeOC(O) |
| H | 6-CN | 2-F | allyl | 7-OMe | 5-SEt | H | MeOC(O) |
| H | 3-CN | 2-Cl | allyl | 5-SEt | 3-$NO_2$ | 4-$NO_2$ | MeOC(O) |

TABLE 26

| Compounds of Formula I wherein Z = $NR^7$, X = CH, Y = N, $R^2 = R^4 = R^6$ = H and | | | | | | | |
|---|---|---|---|---|---|---|---|
| $R^1$ | $R^3$ | $R^5$ | $R^7$ | $R^1$ | $R^3$ | $R^5$ | $R^7$ |
| H | 3-$CF_3$ | 4-F | H | 6-F | 3-$CF_3C_2$ | 4-F | propargyl |
| H | 3-$CF_3$ | 4-Cl | H | 6-F | 3-$SF_5$ | 4-F | propargyl |
| H | 3-$CF_3$ | 2-F, 4-F | H | 6-Cl | 3-MeS(O) | 4-CN | propargyl |
| H | 3-$CF_3$ | 4-$CF_3$ | H | 6-Cl | 3-MeS$(O)_2$ | 4-$CF_3CF_2$ | propargyl |
| H | 3-$CF_3$ | 4-Br | Me | 6-Br | 3-F | 4-$SF_5$ | EtC(O) |
| H | 3-$CF_3$ | 4-CN | Me | 6-Br | 3-I | H | EtC(O) |
| H | 3-$CF_3$ | 4-$NO_2$ | Me | 6-I | 3-Br | 2-Me | EtC(O) |
| H | 3-$CF_3$ | 4-I | Me | 6-I | 3-Cl | 3-OMe | EtC(O) |
| H | 3-$CF_3$ | 4-MeS(O) | allyl | 7-Me | 3-$CF_3O$ | 3-SEt | MeOC(O) |
| H | 3-$CF_3$ | 4-MeS$(O)_2$ | allyl | 7-Cl | 4-$SF_5$ | 4-$CF_3O$ | MeOC(O) |
| H | 6-CN | 2-F | allyl | 7-OMe | 5-SEt | H | MeOC(O) |
| H | 3-CN | 2-Cl | allyl | 5-SEt | 3-$NO_2$ | 4-$NO_2$ | MeOC(O) |

TABLE 27

| Compounds of Formula I wherein Z = $NR^7$, X = N, Y = CH, $R^2 = R^4 = R^6$ = H and | | | | | | | |
|---|---|---|---|---|---|---|---|
| $R^1$ | $R^3$ | $R^5$ | $R^7$ | $R^1$ | $R^3$ | $R^5$ | $R^7$ |
| H | 3-$CF_3$ | 4-F | H | 6-F | 3-$CF_3C_2$ | 4-F | propargyl |
| H | 3-$CF_3$ | 4-Cl | H | 6-F | 3-$SF_5$ | 4-F | propargyl |
| H | 3-$CF_3$ | 2-F, 4-F | H | 6-Cl | 3-MeS(O) | 4-CN | propargyl |
| H | 3-$CF_3$ | 4-$CF_3$ | H | 6-Cl | 3-MeS$(O)_2$ | 4-$CF_3CF_2$ | propargyl |
| H | 3-$CF_3$ | 4-Br | Me | 6-Br | 3-F | 4-$SF_5$ | EtC(O) |
| H | 3-$CF_3$ | 4-CN | Me | 6-Br | 3-I | H | EtC(O) |

TABLE 27-continued

| Compounds of Formula I wherein Z = $NR^7$, X = N, Y = CH, $R^2 = R^4 = R^6$ = H and | | | | | | | |
|---|---|---|---|---|---|---|---|
| $R^1$ | $R^3$ | $R^5$ | $R^7$ | $R^1$ | $R^3$ | $R^5$ | $R^7$ |
| H | 3-$CF_3$ | 4-$NO_2$ | Me | 6-I | 3-Br | 2-Me | EtC(O) |
| H | 3-$CF_3$ | 4-I | Me | 6-I | 3-Cl | 3-OMe | EtC(O) |
| H | 3-$CF_3$ | 4-MeS(O) | allyl | 7-Me | 3-$CF_3$O | 3-SEt | MeOC(O) |
| H | 3-$CF_3$ | 4-MeS$(O)_2$ | allyl | 7-Cl | 4-$SF_5$ | 4-$CF_3$O | MeOC(O) |
| H | 6-CN | 2-F | allyl | 7-OMe | 5-SEt | H | MeOC(O) |
| H | 3-CN | 2-Cl | allyl | 5-SEt | 3-$NO_2$ | 4-$NO_2$ | MeOC(O) |

TABLE 28

| Compounds of Formula I wherein Z = $NR^7$, X = N, Y = N, $R^2 = R^4 = R^6$ = H and | | | | | | | |
|---|---|---|---|---|---|---|---|
| $R^1$ | $R^3$ | $R^5$ | $R^7$ | $R^1$ | $R^3$ | $R^5$ | $R^7$ |
| H | 3-$CF_3$ | 4-F | H | 6-F | 3-$CF_3C_2$ | 4-F | propargyl |
| H | 3-$CF_3$ | 4-Cl | H | 6-F | 3-$SF_5$ | 4-F | propargyl |
| H | 3-$CF_3$ | 2-F, 4-F | H | 6-Cl | 3-MeS(O) | 4-CN | propargyl |
| H | 3-$CF_3$ | 4-$CF_3$ | H | 6-Cl | 3-MeS$(O)_2$ | 4-$CF_3CF_2$ | propargyl |
| H | 3-$CF_3$ | 4-Br | Me | 6-Br | 3-F | 4-$SF_5$ | EtC(O) |
| H | 3-$CF_3$ | 4-CN | Me | 6-Br | 3-I | H | EtC(O) |
| H | 3-$CF_3$ | 4-$NO_2$ | Me | 6-I | 3-Br | 2-Me | EtC(O) |
| H | 3-$CF_3$ | 4-I | Me | 6-I | 3-Cl | 3-OMe | EtC(O) |
| H | 3-$CF_3$ | 4-MeS(O) | allyl | 7-Me | 3-$CF_3$O | 3-SEt | MeOC(O) |
| H | 3-$CF_3$ | 4-MeS$(O)_2$ | allyl | 7-Cl | 4-$SF_5$ | 4-$CF_3$O | MeOC(O) |
| H | 6-CN | 2-F | allyl | 7-OMe | 5-SEt | H | MeOC(O) |
| H | 3-CN | 2-Cl | allyl | 5-SEt | 3-$NO_2$ | 4-$NO_2$ | MeOC(O) |

TABLE 29

| Compounds of Formula I wherein Z = C═$NOR^8$, X = CH, Y = CH, $R^2 = R^4 = R^6$ = H and | | | | | | | |
|---|---|---|---|---|---|---|---|
| $R^1$ | $R^3$ | $R^5$ | $R^8$ | $R^1$ | $R^3$ | $R^5$ | $R^8$ |
| H | 3-$CF_3$ | 4-F | H | 6-F | 3-$CF_3CF_2$ | 4-F | Me |
| H | 3-$CF_3$ | 4-Cl | H | 6-F | 3-$SF_5$ | 4-F | Me |
| H | 3-$CF_3$ | 2-F, 4-F | H | 6-Cl | 3-MeS(O) | 4-CN | Me |
| H | 3-$CF_3$ | 4-$CF_3$ | H | 6-Cl | 3-MeS$(O)_2$ | 4-$CF_3CF_2$ | Et |
| H | 3-$CF_3$ | 4-Br | H | 6-Br | 3-F | 4-$SF_5$ | Et |
| H | 3-$CF_3$ | 4-CN | H | 6-Br | 3-I | H | Et |
| H | 3-$CF_3$ | 4-$NO_2$ | H | 6-I | 3-Br | 2-Me | n-Pr |
| H | 3-$CF_3$ | 4-I | H | 6-I | 3-Cl | 3-OMe | n-Pr |
| H | 3-$CF_3$ | 4-MeS(O) | H | 7-Me | 3-$CF_3$O | 3-SEt | i-Pr |
| H | 3-$CF_3$ | 4-MeS$(O)_2$ | H | 7-Cl | 4-$SF_5$ | 4-$CF_3$O | n-Bu |
| H | 6-CN | 2-F | H | 7-OMe | 5-SEt | H | s-Bu |
| H | 3-CN | 2-Cl | H | 5-SEt | 3-$NO_2$ | 4-$NO_2$ | t-Bu |

TABLE 30

| Compounds of Formula I wherein Z = C═$NOR^8$, X = CH, Y = N, $R^2 = R^4 = R^6$ = H and | | | | | | | |
|---|---|---|---|---|---|---|---|
| $R^1$ | $R^3$ | $R^5$ | $R^8$ | $R^1$ | $R^3$ | $R^5$ | $R^8$ |
| H | 3-$CF_3$ | 4-F | H | 6-F | 3-$CF_3CF_2$ | 4-F | Me |
| H | 3-$CF_3$ | 4-Cl | H | 6-F | 3-$SF_5$ | 4-F | Me |
| H | 3-$CF_3$ | 2-F, 4-F | H | 6-Cl | 3-MeS(O) | 4-CN | Me |
| H | 3-$CF_3$ | 4-$CF_3$ | H | 6-Cl | 3-MeS$(O)_2$ | 4-$CF_3CF_2$ | Et |
| H | 3-$CF_3$ | 4-Br | H | 6-Br | 3-F | 4-$SF_5$ | Et |
| H | 3-$CF_3$ | 4-CN | H | 6-Br | 3-I | H | Et |
| H | 3-$CF_3$ | 4-$NO_2$ | H | 6-I | 3-Br | 2-Me | n-Pr |
| H | 3-$CF_3$ | 4-I | H | 6-I | 3-Cl | 3-OMe | n-Pr |

TABLE 30-continued

| Compounds of Formula I wherein Z = C=NOR[8], X = CH, Y = N, $R^2 = R^4 = R^6$ = H and | | | | | | | |
|---|---|---|---|---|---|---|---|
| $R^1$ | $R^3$ | $R^5$ | $R^8$ | $R^1$ | $R^3$ | $R^5$ | $R^8$ |
| H | 3-$CF_3$ | 4-MeS(O) | H | 7-Me | 3-$CF_3$O | 3-SEt | i-Pr |
| H | 3-$CF_3$ | 4-MeS$(O)_2$ | H | 7-Cl | 4-$SF_5$ | 4-$CF_3$O | n-Bu |
| H | 6-CN | 2-F | H | 7-OMe | 5-SEt | H | s-Bu |
| H | 3-CN | 2-Cl | H | 5-SEt | 3-$NO_2$ | 4-$NO_2$ | t-Bu |

TABLE 31

| Compounds of Formula I wherein Z = C=NOR[8], X = N, Y = CH, $R^2 = R^4 = R^6$ = H and | | | | | | | |
|---|---|---|---|---|---|---|---|
| $R^1$ | $R^3$ | $R^5$ | $R^8$ | $R^1$ | $R^3$ | $R^5$ | $R^8$ |
| H | 3-$CF_3$ | 4-F | H | 6-F | 3-$CF_3CF_2$ | 4-F | Me |
| H | 3-$CF_3$ | 4-Cl | H | 6-F | 3-$SF_5$ | 4-F | Me |
| H | 3-$CF_3$ | 2-F, 4-F | H | 6-Cl | 3-MeS(O) | 4-CN | Me |
| H | 3-$CF_3$ | 4-$CF_3$ | H | 6-Cl | 3-MeS$(O)_2$ | 4-$CF_3CF_2$ | Et |
| H | 3-$CF_3$ | 4-Br | H | 6-Br | 3-F | 4-$SF_5$ | Et |
| H | 3-$CF_3$ | 4-CN | H | 6-Br | 3-I | H | Et |
| H | 3-$CF_3$ | 4-$NO_2$ | H | 6-I | 3-Br | 2-Me | n-Pr |
| H | 3-$CF_3$ | 4-I | H | 6-I | 3-Cl | 3-OMe | n-Pr |
| H | 3-$CF_3$ | 4-MeS(O) | H | 7-Me | 3-$CF_3$O | 3-SEt | i-Pr |
| H | 3-$CF_3$ | 4-MeS$(O)_2$ | H | 7-Cl | 4-$SF_5$ | 4-$CF_3$O | n-Bu |
| H | 6-CN | 2-F | H | 7-OMe | 5-SEt | H | s-Bu |
| H | 3-CN | 2-Cl | H | 5-SEt | 3-$NO_2$ | 4-$NO_2$ | t-Bu |

TABLE 32

| Compounds of Formula I wherein Z = C=NOR[8], X = N, Y = N, $R^2 = R^4 = R^6$ = H and | | | | | | | |
|---|---|---|---|---|---|---|---|
| $R^1$ | $R^3$ | $R^5$ | $R^8$ | $R^1$ | $R^3$ | $R^5$ | $R^8$ |
| H | 3-$CF_3$ | 4-F | H | 6-F | 3-$CF_3CF_2$ | 4-F | Me |
| H | 3-$CF_3$ | 4-Cl | H | 6-F | 3-$SF_5$ | 4-F | Me |
| H | 3-$CF_3$ | 2-F, 4-F | H | 6-Cl | 3-MeS(O) | 4-CN | Me |
| H | 3-$CF_3$ | 4-$CF_3$ | H | 6-Cl | 3-MeS$(O)_2$ | 4-$CF_3CF_2$ | Et |
| H | 3-$CF_3$ | 4-Br | H | 6-Br | 3-F | 4-$SF_5$ | Et |
| H | 3-$CF_3$ | 4-CN | H | 6-Br | 3-I | H | Et |
| H | 3-$CF_3$ | 4-$NO_2$ | H | 6-I | 3-Br | 2-Me | n-Pr |
| H | 3-$CF_3$ | 4-I | H | 6-I | 3-Cl | 3-OMe | n-Pr |
| H | 3-$CF_3$ | 4-MeS(O) | H | 7-Me | 3-$CF_3$O | 3-SEt | i-Pr |
| H | 3-$CF_3$ | 4-MeS$(O)_2$ | H | 7-Cl | 4-$SF_5$ | 4-$CF_3$O | n-Bu |
| H | 6-CN | 2-F | H | 7-OMe | 5-SEt | H | s-Bu |
| H | 3-CN | 2-Cl | H | 5-SEt | 3-$NO_2$ | 4-$NO_2$ | t-Bu |

TABLE 33

| Compounds of Formula I wherein Z = CHOR[9], X = CH, Y = CH, $R^2 = R^4 = R^6$ = H and | | | | | | | |
|---|---|---|---|---|---|---|---|
| $R^1$ | $R^3$ | $R^5$ | $R^9$ | $R^1$ | $R^3$ | $R^5$ | $R^9$ |
| H | 3-$CF_3$ | 4-F | H | 6-F | 3-$CF_3CF_2$ | 4-F | Me |
| H | 3-$CF_3$ | 4-Cl | H | 6-F | 3-$SF_5$ | 4-F | Me |
| H | 3-$CF_3$ | 2-F, 4-F | H | 6-Cl | 3-MeS(O) | 4-CN | Me |
| H | 3-$CF_3$ | 4-$CF_3$ | H | 6-Cl | 3-MeS$(O)_2$ | 4-$CF_3CF_2$ | Et |
| H | 3-$CF_3$ | 4-Br | H | 6-Br | 3-F | 4-$SF_5$ | Et |
| H | 3-$CF_3$ | 4-CN | H | 6-Br | 3-I | H | Et |
| H | 3-$CF_3$ | 4-$NO_2$ | H | 6-I | 3-Br | 2-Me | n-Pr |
| H | 3-$CF_3$ | 4-I | H | 6-I | 3-Cl | 3-OMe | n-Pr |
| H | 3-$CF_3$ | 4-MeS(O) | H | 7-Me | 3-$CF_3$O | 3-SEt | i-Pr |
| H | 3-$CF_3$ | 4-MeS$(O)_2$ | H | 7-Cl | 4-$SF_5$ | 4-$CF_3$O | n-Bu |

TABLE 33-continued

Compounds of Formula I wherein Z = $CHOR^9$, X = CH, Y = CH, $R^2$ = $R^4$ = $R^6$ = H and

| $R^1$ | $R^3$ | $R^5$ | $R^9$ | $R^1$ | $R^3$ | $R^5$ | $R^9$ |
|---|---|---|---|---|---|---|---|
| H | 6-CN | 2-F | H | 7-OMe | 5-SEt | H | i-Bu |
| H | 3-CN | 2-Cl | H | 5-SEt | 3-$NO_2$ | 4-$NO_2$ | s-Bu |

TABLE 34

Compounds of Formula I wherein Z = $CHOR^9$, X = CH, Y = N, $R^2$ = $R^4$ = $R^6$ = H and

| $R^1$ | $R^3$ | $R^5$ | $R^9$ | $R^1$ | $R^3$ | $R^5$ | $R^9$ |
|---|---|---|---|---|---|---|---|
| H | 3-$CF_3$ | 4-F | H | 6-F | 3-$CF_3CF_2$ | 4-F | Me |
| H | 3-$CF_3$ | 4-Cl | H | 6-F | 3-$SF_5$ | 4-F | Me |
| H | 3-$CF_3$ | 2-F, 4-F | H | 6-Cl | 3-MeS(O) | 4-CN | Me |
| H | 3-$CF_3$ | 4-$CF_3$ | H | 6-Cl | 3-MeS$(O)_2$ | 4-$CF_3CF_2$ | Et |
| H | 3-$CF_3$ | 4-Br | H | 6-Br | 3-F | 4-$SF_5$ | Et |
| H | 3-$CF_3$ | 4-CN | H | 6-Br | 3-I | H | Et |
| H | 3-$CF_3$ | 4-$NO_2$ | H | 6-I | 3-Br | 2-Me | n-Pr |
| H | 3-$CF_3$ | 4-I | H | 6-I | 3-Cl | 3-OMe | n-Pr |
| H | 3-$CF_3$ | 4-MeS(O) | H | 7-Me | 3-$CF_3O$ | 3-SEt | i-Pr |
| H | 3-$CF_3$ | 4-MeS$(O)_2$ | H | 7-Cl | 4-$SF_5$ | 4-$CF_3O$ | n-Bu |
| H | 6-CN | 2-F | H | 7-OMe | 5-SEt | H | i-Bu |
| H | 3-CN | 2-Cl | H | 5-SEt | 3-$NO_2$ | 4-$NO_2$ | s-Bu |

TABLE 35

Compounds of Formula I wherein Z = $CHOR^9$, X = N, Y = CH, $R^2$ = $R^4$ = $R^6$ = H and

| $R^1$ | $R^3$ | $R^5$ | $R^9$ | $R^1$ | $R^3$ | $R^5$ | $R^9$ |
|---|---|---|---|---|---|---|---|
| H | 3-$CF_3$ | 4-F | H | 6-F | 3-$CF_3CF_2$ | 4-F | Me |
| H | 3-$CF_3$ | 4-Cl | H | 6-F | 3-$SF_5$ | 4-F | Me |
| H | 3-$CF_3$ | 2-F, 4-F | H | 6-Cl | 3-MeS(O) | 4-CN | Me |
| H | 3-$CF_3$ | 4-$CF_3$ | H | 6-Cl | 3-MeS$(O)_2$ | 4-$CF_3CF_2$ | Et |
| H | 3-$CF_3$ | 4-Br | H | 6-Br | 3-F | 4-$SF_5$ | Et |
| H | 3-$CF_3$ | 4-CN | H | 6-Br | 3-I | H | Et |
| H | 3-$CF_3$ | 4-$NO_2$ | H | 6-I | 3-Br | 2-Me | n-Pr |
| H | 3-$CF_3$ | 4-I | H | 6-I | 3-Cl | 3-OMe | n-Pr |
| H | 3-$CF_3$ | 4-MeS(O) | H | 7-Me | 3-$CF_3O$ | 3-SEt | i-Pr |
| H | 3-$CF_3$ | 4-MeS$(O)_2$ | H | 7-Cl | 4-$SF_5$ | 4-$CF_3O$ | n-Bu |
| H | 6-CN | 2-F | H | 7-OMe | 5-SEt | H | i-Bu |
| H | 3-CN | 2-Cl | H | 5-SEt | 3-$NO_2$ | 4-$NO_2$ | s-Bu |

TABLE 36

Compounds of Formula I wherein Z = $CHOR^9$, X = N, Y = N, $R^2$ = $R^4$ = $R^6$ = H and

| $R^1$ | $R^3$ | $R^5$ | $R^9$ | $R^1$ | $R^3$ | $R^5$ | $R^9$ |
|---|---|---|---|---|---|---|---|
| H | 3-$CF_3$ | 4-F | H | 6-F | 3-$CF_3CF_2$ | 4-F | Me |
| H | 3-$CF_3$ | 4-Cl | H | 6-F | 3-$SF_5$ | 4-F | Me |
| H | 3-$CF_3$ | 2-F, 4-F | H | 6-Cl | 3-MeS(O) | 4-CN | Me |
| H | 3-$CF_3$ | 4-$CF_3$ | H | 6-Cl | 3-MeS$(O)_2$ | 4-$CF_3CF_2$ | Et |
| H | 3-$CF_3$ | 4-Br | H | 6-Br | 3-F | 4-$SF_5$ | Et |
| H | 3-$CF_3$ | 4-CN | H | 6-Br | 3-I | H | Et |
| H | 3-$CF_3$ | 4-$NO_2$ | H | 6-I | 3-Br | 2-Me | n-Pr |
| H | 3-$CF_3$ | 4-I | H | 6-I | 3-Cl | 3-OMe | n-Pr |
| H | 3-$CF_3$ | 4-MeS(O) | H | 7-Me | 3-$CF_3O$ | 3-SEt | i-Pr |
| H | 3-$CF_3$ | 4-MeS$(O)_2$ | H | 7-Cl | 4-$SF_5$ | 4-$CF_3O$ | n-Bu |
| H | 6-CN | 2-F | H | 7-OMe | 5-SEt | H | i-Bu |
| H | 3-CN | 2-Cl | H | 5-SEt | 3-$NO_2$ | 4-$NO_2$ | s-Bu |

TABLE 37

Compounds of Formula I wherein Z = $CR^{10}R^{11}$, X = CH, Y = CH, $R^2 = R^4 = R^6$ = H and

| $R^1$ | $R^3$ | $R^5$ | $R^{10}$ | $R^{11}$ | $R^1$ | $R^3$ | $R^5$ | $R^{10}$ | $R^{11}$ |
|---|---|---|---|---|---|---|---|---|---|
| H | 3-$CF_3$ | 4-F | H | H | 6-F | 3-$CF_3CF_2$ | 4-F | Me | H |
| H | 3-$CF_3$ | 4-Cl | H | H | 6-F | 3-$SF_5$ | 4-F | Me | H |
| H | 3-$CF_3$ | 2-F, 4-F | H | H | 6-Cl | 3-MeS(O) | 4-CN | Et | H |
| H | 3-$CF_3$ | 4-$CF_3$ | H | H | 6-Cl | 3-MeS$(O)_2$ | 4-$CF_3CF_2$ | Et | H |
| H | 3-$CF_3$ | 4-Br | H | H | 6-Br | 3-F | 4-$SF_5$ | n-Pr | H |
| H | 3-$CF_3$ | 4-CN | H | H | 6-Br | 3-I | H | n-Pr | H |
| H | 3-$CF_3$ | 4-$NO_2$ | H | H | 6-I | 3-Br | 2-Me | i-Pr | H |
| H | 3-$CF_3$ | 4-I | H | H | 6-I | 3-Cl | 3-OMe | i-Pr | H |
| H | 3-$CF_3$ | 4-MeS(O) | H | H | 7-Me | 3-$CF_3O$ | 3-SEt | n-Bu | H |
| H | 3-$CF_3$ | 4-MeS$(O)_2$ | H | H | 7-Cl | 4-$SF_5$ | 4-$CF_3O$ | Me | Me |
| H | 6-CN | 2-F | H | H | 7-OMe | 5-SEt | H | Me | Et |
| H | 3-CN | 2-Cl | H | H | 5-SEt | 3-$NO_2$ | 4-$NO_2$ | Et | Et |

TABLE 38

Compounds of Formula I wherein Z = $CR^{10}R^{11}$, X = CH, Y = N, $R^2 = R^4 = R^6$ = H and

| $R^1$ | $R^3$ | $R^5$ | $R^{10}$ | $R^{11}$ | $R^1$ | $R^3$ | $R^5$ | $R^{10}$ | $R^{11}$ |
|---|---|---|---|---|---|---|---|---|---|
| H | 3-$CF_3$ | 4-F | H | H | 6-F | 3-$CF_3CF_2$ | 4-F | Me | H |
| H | 3-$CF_3$ | 4-Cl | H | H | 6-F | 3-$SF_5$ | 4-F | Me | H |
| H | 3-$CF_3$ | 2-F, 4-F | H | H | 6-Cl | 3-MeS(O) | 4-CN | Et | H |
| H | 3-$CF_3$ | 4-$CF_3$ | H | H | 6-Cl | 3-MeS$(O)_2$ | 4-$CF_3CF_2$ | Et | H |
| H | 3-$CF_3$ | 4-Br | H | H | 6-Br | 3-F | 4-$SF_5$ | n-Pr | H |
| H | 3-$CF_3$ | 4-CN | H | H | 6-Br | 3-I | H | n-Pr | H |
| H | 3-$CF_3$ | 4-$NO_2$ | H | H | 6-I | 3-Br | 2-Me | i-Pr | H |
| H | 3-$CF_3$ | 4-I | H | H | 6-I | 3-Cl | 3-OMe | i-Pr | H |
| H | 3-$CF_3$ | 4-MeS(O) | H | H | 7-Me | 3-$CF_{3O}$ | 3-SEt | n-Bu | H |
| H | 3-$CF_3$ | 4-MeS$(O)_2$ | H | H | 7-Cl | 4-$SF_5$ | 4-$CF_3O$ | Me | Me |
| H | 6-CN | 2-F | H | H | 7-OMe | 5-SEt | H | Me | Et |
| H | 3-CN | 2-Cl | H | H | 5-SEt | 3-$NO_2$ | 4-$NO_2$ | Et | Et |

TABLE 39

Compounds of Formula I wherein Z = $CR^{10}R^{11}$, X = N, Y = CH, $R^2 = R^4 = R^6$ = H and

| $R^1$ | $R^3$ | $R^5$ | $R^{10}$ | $R^{11}$ | $R^1$ | $R^3$ | $R^5$ | $R^{10}$ | $R^{11}$ |
|---|---|---|---|---|---|---|---|---|---|
| H | 3-$CF_3$ | 4-F | H | H | 6-F | 3-$CF_3CF_2$ | 4-F | Me | H |
| H | 3-$CF_3$ | 4-Cl | H | H | 6-F | 3-$SF_5$ | 4-F | Me | H |
| H | 3-$CF_3$ | 2-F, 4-F | H | H | 6-Cl | 3-MeS(O) | 4-CN | Et | H |
| H | 3-$CF_3$ | 4-$CF_3$ | H | H | 6-Cl | 3-MeS$(O)_2$ | 4-$CF_3CF_2$ | Et | H |
| H | 3-$CF_3$ | 4-Br | H | H | 6-Br | 3-F | 4-$SF_5$ | n-Pr | H |
| H | 3-$CF_3$ | 4-CN | H | H | 6-Br | 3-I | H | n-Pr | H |
| H | 3-$CF_3$ | 4-$NO_2$ | H | H | 6-I | 3-Br | 2-Me | i-Pr | H |
| H | 3-$CF_3$ | 4-I | H | H | 6-I | 3-Cl | 3-OMe | i-Pr | H |
| H | 3-$CF_3$ | 4-MeS(O) | H | H | 7-Me | 3-$CF_{3O}$ | 3-SEt | n-Bu | H |
| H | 3-$CF_3$ | 4-MeS$(O)_2$ | H | H | 7-Cl | 4-$SF_5$ | 4-$CF_3O$ | Me | Me |
| H | 6-CN | 2-F | H | H | 7-OMe | 5-SEt | H | Me | Et |
| H | 3-CN | 2-Cl | H | H | 5-SEt | 3-$NO_2$ | 4-$NO_2$ | Et | Et |

TABLE 40

Compounds of Formula I wherein Z = $CR^{10}R^{11}$, X = N, Y = N, $R^2 = R^4 = R^6$ = H and

| $R^1$ | $R^3$ | $R^5$ | $R^{10}$ | $R^{11}$ | $R^1$ | $R^3$ | $R^5$ | $R^{10}$ | $R^{11}$ |
|---|---|---|---|---|---|---|---|---|---|
| H | 3-$CF_3$ | 4-F | H | H | 6-F | 3-$CF_3CF_2$ | 4-F | Me | H |
| H | 3-$CF_3$ | 4-Cl | H | H | 6-F | 3-$SF_5$ | 4-F | Me | H |

TABLE 40-continued

| Compounds of Formula I wherein Z = $CR^{10}R^{11}$, X = N, Y = N, $R^2$ = $R^4$ = $R^6$ = H and | | | | | | | | | |
|---|---|---|---|---|---|---|---|---|---|
| $R^1$ | $R^3$ | $R^5$ | $R^{10}$ | $R^{11}$ | $R^1$ | $R^3$ | $R^5$ | $R^{10}$ | $R^{11}$ |
| H | 3-$CF_3$ | 2-F, 4-F | H | H | 6-Cl | 3-MeS(O) | 4-CN | Et | H |
| H | 3-$CF_3$ | 4-$CF_3$ | H | H | 6-Cl | 3-MeS$(O)_2$ | 4-$CF_3CF_2$ | Et | H |
| H | 3-$CF_3$ | 4-Br | H | H | 6-Br | 3-F | 4-$SF_5$ | n-Pr | H |
| H | 3-$CF_3$ | 4-CN | H | H | 6-Br | 3-I | H | n-Pr | H |
| H | 3-$CF_3$ | 4-$NO_2$ | H | H | 6-I | 3-Br | 2-Me | i-Pr | H |
| H | 3-$CF_3$ | 4-I | H | H | 6-I | 3-Cl | 3-OMe | i-Pr | H |
| H | 3-$CF_3$ | 4-MeS(O) | H | H | 7-Me | 3-$CF_{3O}$ | 3-SEt | n-Bu | H |
| H | 3-$CF_3$ | 4-MeS$(O)_2$ | H | H | 7-Cl | 4-$SF_5$ | 4-$CF_3O$ | Me | Me |
| H | 6-CN | 2-F | H | H | 7-OMe | 5-SEt | H | Me | Et |
| H | 3-CN | 2-Cl | H | H | 5-SEt | 3-$NO_2$ | 4-$NO_2$ | Et | Et |

TABLE 41

| Compounds of Formula I wherein Z = O, X = CH, Y = CH and | | | | | |
|---|---|---|---|---|---|
| $R^1$ | $R^2$ | $R^3$ | $R^4$ | $R^5$ | $R^6$ |
| 8-Me | 6-F | 2-Cl | 3-Cl | 2-F, 3-F | 4-F |
| 8-Me | 6-Cl | 2-F | 4-F | 2-Cl, 3-Cl | 4-Cl |
| 8-Cl | 6-Br | 2-Br | 5-Cl | 3-F | 4-allyloxy |
| 8-Cl | 6-I | 3-$CF_3$ | 4-F | 2-Cl, 3-Cl | 5-Cl, 6-Cl |
| 8-MeS(O) | H | 3-$NO_2$ | 5-$NO_2$ | H | 4-$Cl_2C{=}CHCH_2O$ |
| 8-MeS$(O)_2$ | H | 3-$SF_5$ | 5-$CF_3$ | H | 4-propargyloxy |
| 6-$CF_3O$ | H | 2-Cl | 6-F | 3-$CF_3$ | 2-Cl |
| 6-CN | H | 3-$CF_3$ | 4-F | 4-CN | 2-HC≡CCHClO— |
| 6-$SF_5$ | H | 3-MeS(O) | 2-Cl | 4-F | H |
| H | H | 2,3-(O—$CF_2$—O—) | | 4-F | H |

TABLE 42

| Compounds of Formula I wherein Z = C(=O), X = CH, Y = CH and | | | | | |
|---|---|---|---|---|---|
| $R^1$ | $R^2$ | $R^3$ | $R^4$ | $R^5$ | $R^6$ |
| 8-Me | 6-F | 2-Cl | 3-Cl | 2-F, 3-F | 4-F |
| 8-Me | 6-Cl | 2-F | 4-F | 2-Cl, 3-Cl | 4-Cl |
| 8-Cl | 6-Br | 2-Br | 5-Cl | 3-F | 4-allyloxy |
| 8-Cl | 6-I | 3-$CF_3$ | 4-F | 2-Cl, 3-Cl | 5-Cl, 6-Cl |
| 8-MeS(O) | H | 3-$NO_2$ | 5-$NO_2$ | H | 4-$Cl_2C{=}CHCH_2O$ |
| 8-MeS$(O)_2$ | H | 3-$SF_5$ | 5-$CF_3$ | H | 4-propargyloxy |
| 6-$CF_3O$ | H | 2-Cl | 6-F | 3-$CF_3$ | 2-Cl |
| 6-CN | H | 3-$CF_3$ | 4-F | 4-CN | 2-HC≡CCHClO— |
| 6-$SF_5$ | H | 3-MeS(O) | 2-Cl | 4-F | H |
| H | H | 2,3-(O—$CF_2$—O—) | | 4-F | H |

TABLE 43

| Compounds of Formula I wherein Z = S, X = CH, Y = CH and | | | | | |
|---|---|---|---|---|---|
| $R^1$ | $R^2$ | $R^3$ | $R^4$ | $R^5$ | $R^6$ |
| 8-Me | 6-F | 2-Cl | 3-Cl | 2-F, 3-F | 4-F |
| 8-Me | 6-Cl | 2-F | 4-F | 2-Cl, 3-Cl | 4-Cl |
| 8-Cl | 6-Br | 2-Br | 5-Cl | 3-F | 4-allyloxy |
| 8-Cl | 6-I | 3-$CF_3$ | 4-F | 2-Cl, 3-Cl | 5-Cl, 6-Cl |
| 8-MeS(O) | H | 3-$NO_2$ | 5-$NO_2$ | H | 4-$Cl_2C{=}CHCH_2O$ |
| 8-MeS$(O)_2$ | H | 3-$SF_5$ | 5-$CF_3$ | H | 4-propargyloxy |
| 6-$CF_3O$ | H | 2-Cl | 6-F | 3-$CF_3$ | 2-Cl |
| 6-CN | H | 3-$CF_3$ | 4-F | 4-CN | 2-HC≡CCHClO— |
| 6-$SF_5$ | H | 3-MeS(O) | 2-Cl | 4-F | H |
| H | H | 2,3-(O—$CF_2$—O—) | | 4-F | H |

TABLE 44

| Compounds of Formula I wherein Z = S(O), X = CH, Y = CH and | | | | | |
|---|---|---|---|---|---|
| $R^1$ | $R^2$ | $R^3$ | $R^4$ | $R^5$ | $R^6$ |
| 8-Me | 6-F | 2-Cl | 3-Cl | 2-F, 3-F | 4-F |
| 8-Me | 6-Cl | 2-F | 4-F | 2-Cl, 3-Cl | 4-Cl |
| 8-Cl | 6-Br | 2-Br | 5-Cl | 3-F | 4-allyloxy |
| 8-Cl | 6-I | 3-$CF_3$ | 4-F | 2-Cl, 3-Cl | 5-Cl, 6-Cl |
| 8-MeS(O) | H | 3-$NO_2$ | 5-$NO_2$ | H | 4-$Cl_2C$=$CHCH_2O$ |
| 8-$MeS(O)_2$ | H | 3-$SF_5$ | 5-$CF_3$ | H | 4-propargyloxy |
| 6-$CF_3O$ | H | 2-Cl | 6-F | 3-$CF_3$ | 2-Cl |
| 6-CN | H | 3-$CF_3$ | 4-F | 4-CN | 2-HC≡CCHClO— |
| 6-$SF_5$ | H | 3-MeS(O) | 2-Cl | 4-F | H |
| H | H | 2,3-(O—$CF_2$—O—) | | 4-F | H |

TABLE 45

| Compounds of Formula I wherein Z = $S(O)_2$, X = CH, Y = CH and | | | | | |
|---|---|---|---|---|---|
| $R^1$ | $R^2$ | $R^3$ | $R^4$ | $R^5$ | $R^6$ |
| 8-Me | 6-F | 2-Cl | 3-Cl | 2-F, 3-F | 4-F |
| 8-Me | 6-Cl | 2-F | 4-F | 2-Cl, 3-Cl | 4-Cl |
| 8-Cl | 6-Br | 2-Br | 5-Cl | 3-F | 4-allyloxy |
| 8-Cl | 6-I | 3-$CF_3$ | 4-F | 2-Cl, 3-Cl | 5-Cl, 6-Cl |
| 8-MeS(O) | H | 3-$NO_2$ | 5-$NO_2$ | H | 4-$Cl_2C$=$CHCH_2O$ |
| 8-$MeS(O)_2$ | H | 3-$SF_5$ | 5-$CF_3$ | H | 4-propargyloxy |
| 6-$CF_3O$ | H | 2-Cl | 6-F | 3-$CF_3$ | 2-Cl |
| 6-CN | H | 3-$CF_3$ | 4-F | 4-CN | 2-HC≡CCHClO— |
| 6-$SF_5$ | H | 3-MeS(O) | 2-Cl | 4-F | H |
| H | H | 2,3-(O—$CF_2$—O—) | | 4-F | H |

TABLE 46

| Compounds of Formula I wherein Z = C(=S), X = CH, Y = CH and | | | | | |
|---|---|---|---|---|---|
| $R^1$ | $R^2$ | $R^3$ | $R^4$ | $R^5$ | $R^6$ |
| 8-Me | 6-F | 2-Cl | 3-Cl | 2-F, 3-F | 4-F |
| 8-Me | 6-Cl | 2-F | 4-F | 2-Cl, 3-Cl | 4-Cl |
| 8-Cl | 6-Br | 2-Br | 5-Cl | 3-F | 4-allyloxy |
| 8-Cl | 6-I | 3-$CF_3$ | 4-F | 2-Cl, 3-Cl | 5-Cl, 6-Cl |
| 8-MeS(O) | H | 3-$NO_2$ | 5-$NO_2$ | H | 4-$Cl_2C$=$CHCH_2O$ |
| 8-$MeS(O)_2$ | H | 3-$SF_5$ | 5-$CF_3$ | H | 4-propargyloxy |
| 6-$CF_3O$ | H | 2-Cl | 6-F | 3-$CF_3$ | 2-Cl |
| 6-CN | H | 3-$CF_3$ | 4-F | 4-CN | 2-HC≡CCHClO— |
| 6-$SF_5$ | H | 3-MeS(O) | 2-Cl | 4-F | H |
| H | H | 2,3-(O—$CF_2$—O—) | | 4-F | H |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable | 5–50 | 40–95 | 0–15 |

-continued

| | Weight Percent | | |
|---|---|---|---|
| | Active Ingredient | Diluent | Surfactant |
| Concentrates) | | | |
| Dusts | 1–25 | 70–99 | 0–5 |
| Granules and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers,* 2nd Ed., Dorland Books, Caldwell, New Jersey. Typical liquid diluents are described in Marsden, *Solvents Guide,* 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering, Dec.* 4, 1967, pp 147–48, *Perry's Chemical Engineer's Handbook,* 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299, 566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, Weed Control as a Science, John Wiley and Sons, Inc., New York, 1961, pp 81–96; and Hance et al., *Weed Control Handbook,* 8th Ed., Blackwell Scientific Publications, Oxford, 1989.

In the following Examples, all percentages are by weight and all formulations are prepared in conventional ways. Compound numbers refer to compounds in Index Tables A–B.

Example A

| High Strength Concentrate | |
|---|---|
| Compound 19 | 98.5% |
| silica aerogel | 0.5% |
| synthetic amorphous fine silica | 1.0%. |

Example B

| Wettable Powder | |
|---|---|
| Compound 19 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example C

| Granule | |
|---|---|
| Compound 19 | 10.0% |
| attapulgite granules (low volatile matter, 0.71/0.30 mm; U.S.S. No. 25–50 sieves) | 90.0%. |

Example D

| Extruded Pellet | |
|---|---|
| Compound 19 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Test results indicate that the compounds of the present invention are highly active preemergent and postemergent herbicides or plant growth regulants. Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Some of the compounds are useful for the control of selected grass and broadleaf weeds with tolerance to important agronomic crops which include but are not limited to barley, cotton, wheat, rape, sugar beets, corn (maize), soybeans, rice, tomato, potato, and plantation crops including coffee, cocoa, oil palm, rubber, sugarcane, citrus, grapes, fruit trees, nut trees, banana, plantain, pineapple, hops, tea, forests such as eucalyptus and conifers, e.g., loblolly pine, and turf species, e.g., Kentucky bluegrass, St. Augustine grass, Kentucky rescue and Bermuda grass. Those skilled in the art will appreciate that not all compounds are equally effective against all weeds. Alternatively, the subject compounds are useful to modify plant growth.

A herbicidally effective amount of the compounds of this invention is determined by a number of factors. These factors include: formulation selected, method of application, amount and type of vegetation present, growing conditions, etc. In general, a herbicidally effective amount of compounds of this invention is 0.001 to 20 kg/ha with a preferred range of 0.004 to 1.0 kg/ha. One skilled in the art can easily determine the herbicidally effective amount necessary for the desired level of weed control.

Compounds of this invention can be used alone or in combination with other commercial herbicides, insecticides or fungicides. Compounds of this invention can also be used in combination with commercial herbicide safeners such as benoxacor, dichlormid and furilazole to increase safety to certain crops. A mixture of one or more of the following herbicides with a compound of this invention may be particularly useful for weed control: acetochlor, acifluorfen and its sodium salt, aclonifen, acrolein (2-propenal), alachlor, ametryn, amidosulfuron, amitrole, ammonium sulfamate, anilofos, asulam, atrazine, azimsulfuron, benazolin, benazolin-ethyl, benfluralin, benfuresate, bensulfuron-methyl, bensulide, bentazone, bifenox, bromacil, bromoxynil, bromoxynil octanoate, butachlor, butralin, burylate, chlomethoxyfen, chloramben, chlorbromuron, chloridazon, chlorimuron-ethyl, chlornitrofen, chlorotoluron, chlorpropham, chlorsulfuron, chlorthal-dimethyl, cinmethylin, cinosulfuron, clethodim, clomazone, clopyralid, clopyralid-olamine, cyanazine, cycloate, cyclosulfamuron, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, 2-[4,5-dihydro-4-methyl-4-(1-methylethyl)-5-oxo-1H-imidazol-2-yl]-5-methyl-3-pyridinecarboxylic acid (AC 263,222), difenzoquat metilsulfate, difiufenican, dimepiperate, dimethenamid, dimethylarsinic acid and its sodium salt, dinitramine, diphenamid, diquat dibromide, dithiopyr, diuron, DNOC, endothal, EPTC, esprocarb, ethalfluralin, ethametsulfuron-methyl, ethofumesate, ethyl α,2-dichloro-5-[4-(difluoromethyl)-4,5-dihydro-3-methyl-5-oxo-1H-1,2,4-triazol-1-yl]-4-fluorobenzenepropanoate (F8426), fenoxaprop-ethyl, fenoxaprop-P-ethyl, fenuron, fenuron-TCA, flamprop-methyl, flamprop-M-isopropyl, flamprop-M-methyl, flazasulfuron, fluazifop-butyl, fluazifop-P-butyl, fluchloralin, flumetsulam, flumicloracpentyl, flumioxazin, fluometuron, fluoroglycofen-ethyl, flupoxam, fluridone, flurochloridone, fluroxypyr, fomesafen, fosamine-ammonium, glufosinate, glufosinate-ammonium, glyphosate, glyphosate-isopropylammonium, glyphosate-sesquisodium, glyphosate-trimesium, halosulfuron-methyl, haloxyfop-etotyl, haloxyfop-methyl, hexazinone, imazamethabenz-methyl, imazamox (AC 299 263), imazapyr, imazaquin, imazaquin-ammonium, imazethapyr, imazethapyr-ammonium, imazosulfuron, ioxynil, ioxynil octanoate, ioxynil-sodium, isoproturon, isouron, isoxaben, isoxaflutole (RPA 201772), lactofen, lenacil, linuron, maleic hydrazide, MCPA and its dimethylammonium, potassium and sodium salts, MCPA-isoctyl, mecoprop, mecoprop-P, mefenacet, mefluidide, metam-sodium, methabenzthiazuron, methyl [[2-chloro-4-fluoro-5-[(tetrahydro-3-oxo-1H,3H-[1,3,4]thiadiazolo[3,4-α]pyridazin-1-ylidene)amino]phenyl]thioacetate (KIH 9201), methylarsonic acid and its calcium, monoammonium, monosodium and disodium salts, methyl [[[1-[5-[2-chloro-4-(trifluoromethyl)phenoxy]-2-nitrophenyl]-2-methoxyethylidene]amino]oxy]acetate (AKH-7088), methyl 5-[[[[(4,6-dimethyl-2-pyrimidinyl)amino]carbonyl]amino]sulfonyl]-1-(2-pyridinyl)-1H-pyrazole-4-carboxylate (NC-330), metobenzuron, metolachlor, metosulam, metoxuron, metribuzin, metsulfuron-methyl, molinate, monolinuron, napropamide, naptalam, neburon, nicosulfuron, norflurazon, oryzalin, oxadiazon, 3-oxetanyl 2-[[[[(4,6-dimethyl-2-pyrimidinyl)amino]carbonyl]amino]sulfonyl]benzoate (CGA 277476), oxyfluorfen, paraquat dichloride, pebulate, pendimethalin, perfluidone, phenmedipham, picloram, picloram-potassium, pretilachlor, primisulfuron-methyl, prometon, prometryn, propachlor, propanil, propaquizafop, propazine, propham, propyzamide, prosulfuron, pyrazolynate, pyrazosulfuron-ethyl, pyridate, pyrithiobac, pyrithiobac-sodium, quinclorac, quizalofop-ethyl, quizalofop-P-ethyl, quizalofop-P-tefuryl, rimsulfuron, sethoxydim, siduron, simazine, sulcotrione (ICIA0051), sulfentrazone, sulfometuron-methyl, TCA, TCA-sodium, tebuthiuron, terbacil, terbuthylazine, terbutryn, thenylchlor, thiafluamide (BAY 11390), thifensulfuron-methyl, thiobencarb, tralkoxydim, tri-allate, triasulfuron, tribenuron-methyl, triclopyr, triclopyr-butotyl, triclopyr-triethylammonium, tridiphane, trifluralin, triflusulfuron-methyl, and vernolate.

In certain instances, combinations with other herbicides having a similar spectrum of control but a different mode of action will be particularly advantageous for preventing the development of resistant weeds.

The following Tests demonstrate the control efficacy of the compounds of this invention against specific weeds. The weed control afforded by the compounds is not limited, however, to these species. See Index Tables A–B for compound descriptions.

INDEX TABLE A

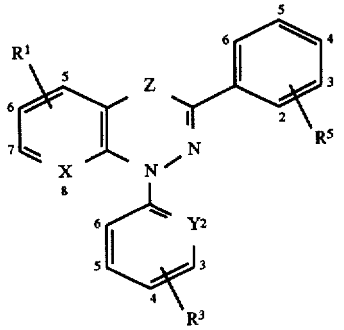

| Cmpd No. | X | Y | Z | $R^1$ | $R^3$ | $R^5$ | m.p (°C.) |
|---|---|---|---|---|---|---|---|
| 1 | CH | CH | C(=O) | H | $3-CF_3$ | 4-Cl | 167–171 |
| 2 | N | CH | C(=O) | H | $3-CF_3$ | 4-Cl | 178–180 |
| 3 | CH | CH | C(=O) | H | $3-CF_3$ | 4-F | 183–186 |
| 4 (Ex. 2) | N | CH | C(=O) | H | $3-CF_3$ | 4-F | 165–167 |
| 5 | CH | CH | C(=O) | H | $3-CF_3$ | $2-CH_3O$ | 104–107 |
| 6 | CH | CH | C(=O) | H | $3-CF_3$ | $4-CH_3$ | 177–179 |
| 7 | CH | CH | C(=O) | H | $3-CF_3$ | H | 164–172 |
| 8 | CH | CH | C(=O) | H | $3-CF_3$ | $3-CF_3$ | 188–191 |
| 9 | N | CH | C(=O) | H | $3-CF_3$ | $2-CH_3O$ | 148–152 |
| 10 | N | CH | C(=O) | H | $3-CF_3$ | $3-CF_3$ | 130–133 |
| 11 | N | CH | C(=O) | H | $3-CF_3$ | $4-CH_3$ | 199–202 |
| 12 | N | CH | C(=O) | H | $3-CF_3$ | H | 199–202 |
| 13 | N | CH | C(=O) | H | $3-CF_3$ | $4-CH_3O$ | 160–163 |
| 14 | CH | CH | C(=O) | H | $3-CF_3$ | 2,4-di-F | 129–131 |
| 15 | N | CH | C(=O) | H | $3-CF_3$ | 2,4-di-F | 139–141 |
| 16 | N | CH | O | H | $3-CF_3$ | 4-Cl | 75–78 |
| 17 | N | CH | S | H | $3-CF_3$ | H | oil* |
| 18 | N | CH | S(O) | H | $3-CF_3$ | H | 143–147 |
| 19 (Ex. 1) | N | N | O | H | $3-CF_3$ | 4-F | 67–72 |
| 20 | N | N | O | H | $3-CF_3$ | 4-Cl | oil* |
| 21 | N | CH | $S(O)_2$ | H | $3-CF_3$ | H | 148–151 |
| 22 | N | CH | C(=O) | $7-CH_3$ | $3-CF_3$ | 4-F | 164–166 |
| 23 (Ex. 3) | N | N | C(=O) | H | $3-CF_3$ | 4-F | 192–196 |
| 24 | N | N | O | H | $3-CF_3$ | $4-CF_3$ | oil* |
| 25 | N | N | O | H | $3-CF_3$ | $4-CF_3O$ | oil* |
| 26 | N | N | O | H | $3-CF_3$ | 3-F | 83–92 |
| 27 | N | N | O | H | $3-CF_3$ | 2-F | oil* |
| 28 | N | N | O | H | $3-CF_3$ | 2,4-di-F | oil* |
| 29 | N | N | O | H | $5-CF_3$ | $4-CF_3$ | oil* |
| 30 | N | N | O | H | $3-CF_3$ | 2-F, $5-CF_3$ | oil* |
| 31 | N | N | O | H | $3-CF_3$ | 4-Br | 106–120 |
| 32 | N | N | O | H | $3-CF_3$ | 4-I | 121–123 |
| 33 | N | N | O | 6-F | $3-CF_3$ | 4-I | 95–107 |
| 34 | N | CH | O | H | 2-F, $3-CF_3$ | 4-F | 87–94 |
| 35 | N | N | O | H | $3-CF_3$ | 4-CN | 98–104 |
| 36 | N | N | O | 6-F | $3-CF_3$ | $4-CF_3$ | 91–101 |
| 37 | N | N | O | 6-Cl | $3-CF_3$ | 3-F | 105–108 |
| 38 | N | N | O | 6-Br | $3-CF_3$ | 3-F | 105–108 |
| 39 | N | N | O | 6-I | $3-CF_3$ | 3-F | 128–131 |
| 40 | N | N | O | 6-I | $3-CF_3$ | 4-CN | 179–183 |
| 41 | N | N | O | 6-Br | $3-CF_3$ | 4-CN | 155–159 |
| 42 | N | N | O | 6-Cl | $3-CF_3$ | 2,4-di-F | 86–92 |
| 43 | N | N | O | 6-F | $3-CF_3$ | 2,4-di-F | 89–117 |
| 44 | N | N | O | 6-Br | $3-CF_3$ | 4-F | 105–108 |
| 45 | N | N | O | 6-Cl | $3-CF_3$ | 4-CN | 160–166 |
| 46 | N | N | O | 6-F | $3-CF_3$ | 4-CN | 148–154 |
| 47 | N | N | O | 6-F | $3-CF_3$ | 4-F | 107–110 |
| 48 | N | N | O | 6-Cl | $3-CF_3$ | 4-F | 97–158 |
| 49 | N | N | O | 6-I | $3-CF_3$ | 4-F | 125–128 |
| 50 | N | CH | O | 6-Cl | $2,3-O(CF_2)O$ | 4-F | 106–129 |
| 51 | N | N | O | 6-F | $3-CF_3$ | $4-SO_2CH_3$ | 155–175 |
| 52 | N | N | O | 6-F | $3-CF_3$ | 2-F | 81–90 |
| 53 | N | CH | O | H | $2,3-O(CF_2)O$ | 4-F | 135–138 |
| 54 | N | CH | O | H | 3-F | 4-F | 130–132 |
| 55 | N | CH | O | 6-F | 3-F | 4-F | 140–155 |
| 56 | N | CH | O | 6-Cl | 3-F | 4-F | 151–153 |
| 57 | N | CH | O | H | 3-Cl | 4-F | 120–125 |
| 58 | N | CH | O | 6-Cl | 3-Cl | 4-F | 145–149 |
| 59 | N | CH | O | 6-F | 3-Cl | 4-F | 139–141 |

-continued

INDEX TABLE A

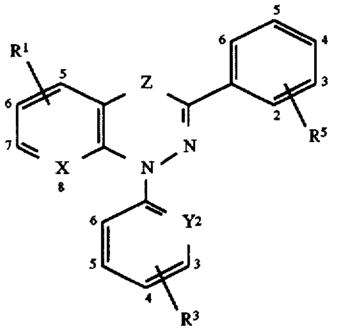

| Cmpd No. | X | Y | Z | $R^1$ | $R^3$ | $R^5$ | m.p (°C.) |
|---|---|---|---|---|---|---|---|
| 60 | N | N | O | H | 3-$CF_3$ | 3,5-di-F | 125–127 |
| 61 | N | N | O | 6-F | 3-$CF_3$ | 3,5-di-F | 148–150 |
| 62 | N | N | O | 6-Cl | 3-$CF_3$ | 3,5-di-F | 148–151 |
| 63 | N | N | O | H | 3,6-di-$CF_3$ | 4-F | 152–153 |
| 64 | N | N | O | 6-Cl | 3-$CF_3$ | 3,4-di-F | 119–121 |
| 65 | N | N | O | 6-F | 3-$CF_3$ | 3,4-di-F | 109–116 |
| 66 | N | N | C(=NOH) | H | 3-$CF_3$ | 4-F | 230–236 |
| 67 | N | N | O | 6-CN | 3-$CF_3$ | 4-F | 160–167 |
| 68 | N | N | O | 6-F | 3,6-di-$CF_3$ | 4-F | 184–188 |
| 69 | N | N | O | 6-CN | 3-$CF_3$ | 3,5-di-F | 162–166 |
| 70 | N | N | O | H | 3-$CF_3$ | 3,4-di-F | 95–97 |
| 71 | N | CH | O | 6-F | 3-$CF_3$ | 4-F | 113–115 |
| 72 | N | CH | O | 6-Cl | 3-$CF_3$ | 4-F | 101–104 |
| 73 | N | CH | O | 6-CN | 3-F | 4-F | 190–197 |
| 74 | N | N | O | 6-F | 4-$CF_3$, 6-Cl | 4-F | 100–110 |
| 75 | N | N | O | 6-Cl | 4-$CF_3$, 6-Cl | 4-F | 182–185 |
| 76 | N | N | O | H | 4-$CF_3$, 6-Cl | 4-F | 145–151 |
| 77 | N | CH | O | H | 3-$CF_3$ | 4-F | 65–67 |
| 78 | N | CH | O | 6-CN | 3-$CF_3$ | 4-F | 145–155 |
| 79 | N | CH | O | 6-$CH_3$ | 3-$CF_3$ | 4-F | 75–100 |
| 80 | N | N | O | H | 3-$CF_3$ | 2-F, 4-$CF_3$ | oil* |
| 81 | N | N | O | H | 3-$CF_3$ | 2,4,5-tri-F | 92–100 |
| 82 | N | N | O | 6-CN | 3-$CF_3$ | 2,4,5-tri-F | 142–149 |
| 83 | N | CH | O | 6-F | 3-Cl | 3,5-di-F | 170–173 |
| 84 | N | CH | O | 6-Cl | 3-Cl | 3,5-di-F | 190–192 |
| 85 | N | CH | O | H | 3-Cl | 3,5-di-F | 159–161 |
| 86 | N | CH | O | 6-F | 3-F | 3,5-di-F | 179–181 |
| 87 | N | CH | O | H | 3-F | 3,5-di-F | 159–161 |
| 88 | N | CH | O | 6-Cl | 3-F | 3,5-di-F | 186–189 |
| 89 | N | N | O | 6-F | 3-$CF_3$ | 2,4,5-tri-F | 97–100 |
| 90 | N | N | O | 6-F | 3-$CF_3$ | 2-F, 4-$CF_3$ | 108–119 |
| 91 | N | CH | O | 6-F | 3-Cl | 3,4-di-F | 128–130 |
| 92 | N | CH | O | H | 3-Cl | 3,4-di-F | 131–133 |
| 93 | N | CH | O | 6-Cl | 3-Cl | 3,4-di-F | 172–175 |
| 94 | N | CH | O | 6-F | 3-F | 3,4-di-F | 144–146 |
| 95 | N | CH | O | 6-Cl | 3-F | 3,4-di-F | 161–163 |
| 96 | N | CH | O | H | 3-F | 3,4-di-F | 158–160 |
| 97 | N | CH | O | 6-F | 3-$OCF_3$ | 4-F | 79–81 |
| 98 | N | CH | O | 6-Cl | 3-$OCF_3$ | 4-F | 60–62 |
| 99 | N | CH | O | H | 3-$OCF_3$ | 4-F | 81–83 |
| 100 | N | N | O | 6-F | 3-$CF_3$ | 2,4-di-$CF_3$ | 87–90 |
| 101 | N | N | O | H | 3-$CF_3$ | 2,4-di-$CF_3$ | 111–120 |
| 102 | N | N | O | 6-Cl | 3-$CF_3$ | 2,4-di-$CF_3$ | 127–134 |
| 103 | N | N | O | 6-F | 3-$CF_3$ | 3,5-di-$CF_3$ | 177–182 |
| 104 | N | N | O | 6-Cl | 3-$CF_3$ | 3,5-di-$CF_3$ | 173–175 |
| 105 | N | N | O | H | 3-$CF_3$ | 3,5-di-$CF_3$ | 167–169 |

*See Index Table B for $^1H$ NMR data.

INDEX TABLE B

| Cmpd No. | $^1H$ NMR Data ($CDCl_3$ solution unless indicated otherwise)[a] |
|---|---|
| 17 | δ 8.08(dd, 1H), 7.95(m, 3H), 7.83(d, 1H), 7.54(t, 1H), 7.40–7.52(m, 5H), 7.00(dd, 1H). |
| 20 | δ 7.80–8.00(m, 5H), 7.47(dd, 1H), 7.40(d, 2H), 7.10(dd, 1H), 6.88(dd, 1H). |
| 24 | δ 8.07(d, 2H), 7.94(m, 2H), 7.86(d, 1H), 7.69(d, 2H), 7.50(d, 1H), 7.12(d, 1H), 6.90(dd, 1H). |
| 25 | δ 7.80–8.05(m, 5H), 7.47(dd, 1H), 7.28(d, 2H), 7.11(dd, 1H), 6.89(dd, 1H). |
| 27 | δ 7.8–8.0(m, 4H), 7.47(m, 2H), 7.10–7.25(m, 3H), 6.91(m, 1H). |
| 28 | δ 7.8–7.95(m, 4H), 7.46(dd, 1H), 7.09(dd, 1H), 6.85–7.00(m, 3H). |
| 29 | δ 8.68(d, 1H), 8.08(d, 2H), 7.96(d, 1H), 7.94(dd, 1H), 7.71(d, 2H), 7.31(dd, 1H), 7.17(dd, 1H), 6.94(dd, 1H). |
| 30 | δ 7.85–8.05(m, 4H), 7.40–7.55(m, 3H), 7.12(m, 1H), 6.92(m, 1H). |
| 80 | δ 7.99(t, 1H), 7.86–7.92(m, 3H), 7.40–7.52(m, 3H), 7.10(dd, 1H), 6.91(dd, 1H). |

[a] $^1H$ NMR data are in ppm downfield from tetramethylsilane. Couplings are designated by (d)-doublet, (t)-triplet, (m)-multiplet, (dd)-doublet of doublets.

BIOLOGICAL EXAMPLES OF THE INVENTION

TEST A

Seeds of barley (*Hordeum vulgate*), barnyardgrass (*Echinochloa crus-galli*), bedstraw (*Galium aparine*), blackgrass (*Alopecurus myosuroides*), chickweed (*Stellaria media*), cocklebur (*Xanthium strumarium*), corn (*Zea mays*), cotton (*Gossypium hirsutum*), crabgrass (*Digitaria sanguinalis*), downy brome (*Bromus tectorum*), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasli*), wheat (*Triticum aestivum*), wild buckwheat (*Polygonum convolvulus*), wild oat (*Avena fatua*) and purple nutsedge (*Cyperus rotundus*) tubers were planted and treated preemergence with test chemicals formulated in a non-phytotoxic solvent mixture which includes a surfactant.

At the same time, these crop and weed species were also treated with postemergence applications of test chemicals formulated in the same manner. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table A, are based on a scale of 0 to 10 where 0 is no effect and 10 is complete control. A dash (–) response means no test result.

TABLE A

| | COMPOUND | | | | | | | | | | | | | | | | | | | |
|---|---|---|---|---|---|---|---|---|---|---|---|---|---|---|---|---|---|---|---|---|
| Rate 2000 g/ha | 1 | 2 | 3 | 4 | 5 | 6 | 7 | 8 | 9 | 10 | 11 | 12 | 13 | 15 | 16 | 17 | 18 | 19 | 22 | 24 |
| POSTEMERGENCE | | | | | | | | | | | | | | | | | | | | |
| Barley | 1 | 0 | 0 | 2 | 0 | 0 | 0 | 0 | 0 | 0 | 0 | 0 | 0 | 2 | 3 | 0 | 7 | 5 | 0 | 5 |
| Barnyardgrass | 2 | 2 | 2 | 2 | 0 | 1 | 1 | 0 | 0 | 1 | 1 | 2 | 1 | 3 | 7 | 2 | 2 | 9 | 2 | 9 |
| Bedstraw | 7 | 6 | 3 | 8 | 0 | 6 | 2 | 0 | 1 | 5 | 3 | 2 | 2 | 5 | 7 | 2 | 2 | 9 | 2 | 9 |
| Blackgrass | 2 | 1 | 0 | 2 | 1 | 1 | 0 | 0 | 0 | 1 | 1 | 1 | 0 | 2 | 7 | 0 | 1 | 5 | 1 | 4 |
| Chickweed | 1 | 2 | 1 | 2 | 0 | 1 | 0 | 0 | 1 | 2 | 3 | 2 | 0 | 7 | 7 | 1 | 2 | 9 | 2 | 9 |
| Cocklebur | 3 | 4 | 3 | 7 | 0 | 3 | 3 | 0 | 0 | 3 | 6 | 3 | 2 | 4 | 8 | 5 | 1 | 9 | 4 | 9 |
| Corn | 1 | 2 | 2 | 2 | 0 | 1 | 1 | 0 | 1 | 1 | 2 | 2 | 2 | 1 | 3 | 2 | 1 | 7 | 2 | 3 |
| Cotton | 4 | 9 | 2 | 8 | 0 | 6 | 0 | 0 | 0 | 5 | 8 | 5 | 0 | 5 | 10 | 3 | 3 | 10 | 7 | 10 |
| Crabgrass | 2 | 2 | 2 | 2 | 0 | 1 | 1 | 0 | 1 | 2 | 2 | 2 | 2 | 4 | 7 | 2 | 1 | 9 | 5 | 9 |
| Downy brome | 0 | 0 | 0 | 1 | 0 | 0 | 0 | 0 | 0 | 0 | 0 | 0 | 0 | 1 | 5 | 1 | 0 | 3 | 0 | 8 |
| Giant foxtail | 2 | 2 | 1 | 2 | 0 | 2 | 0 | 0 | 0 | 1 | 2 | 2 | 1 | 4 | 7 | 1 | 1 | 9 | 2 | 9 |
| Lambsquarter | 2 | 6 | 2 | 5 | 2 | 2 | 2 | 0 | 1 | 3 | 2 | 3 | 2 | 7 | 9 | 7 | 3 | 9 | 3 | 9 |
| Morningglory | 3 | 2 | 2 | 6 | 0 | 1 | 3 | 0 | 1 | 2 | 6 | 3 | 2 | 6 | 8 | 2 | 3 | 9 | 3 | 9 |
| Nutsedge | 1 | 1 | 0 | 0 | 0 | 0 | 0 | 0 | 0 | 0 | 0 | 0 | 0 | 2 | 0 | 0 | 0 | 2 | 4 | 1 |
| Rape | 2 | 4 | 2 | 7 | 0 | 3 | 5 | 0 | 9 | 5 | 3 | 4 | 0 | 6 | 10 | 5 | 7 | 9 | 2 | 10 |
| Rice | 0 | 1 | 1 | 2 | 0 | 1 | 0 | 0 | 0 | 1 | 2 | 2 | 1 | 0 | 4 | 0 | 0 | 3 | 1 | 5 |
| Sorghum | 0 | 1 | 1 | 2 | 0 | 1 | 0 | 0 | 1 | 1 | 1 | 2 | 0 | 2 | 2 | 2 | 0 | 9 | 1 | 7 |
| Soybean | 2 | 2 | 2 | 4 | 0 | 1 | 1 | 0 | 1 | 3 | 2 | 1 | 2 | 2 | 8 | 3 | 0 | 9 | 5 | 9 |
| Sugar beet | 3 | 6 | 4 | 6 | 0 | 3 | 2 | 0 | 2 | 4 | 8 | 7 | 2 | 7 | 10 | 3 | 2 | 8 | 7 | 10 |
| Velvetleaf | 2 | 2 | 2 | 7 | 0 | 1 | 2 | 0 | 0 | 2 | 6 | 2 | 2 | 2 | 9 | 3 | 2 | 9 | 4 | 9 |
| Wheat | 1 | 0 | 0 | 1 | 0 | 0 | 0 | 0 | 0 | 0 | 0 | 0 | 0 | 1 | 3 | 0 | 1 | 3 | 0 | 3 |
| Wild buckwheat | 3 | 1 | 1 | 4 | 1 | 2 | 1 | 0 | 1 | 3 | 3 | 2 | 1 | 6 | 5 | 3 | 2 | 7 | 3 | 8 |
| Wild oat | 0 | 0 | 0 | 1 | 0 | 0 | 0 | 0 | 0 | 1 | 0 | 0 | 0 | 2 | 5 | 0 | 0 | 5 | 0 | 8 |
| Rate 2000 g/ha | 1 | 2 | 3 | 4 | 5 | 6 | 7 | 8 | 9 | 10 | 11 | 12 | 13 | 15 | 16 | 17 | 18 | 19 | 22 | 24 |
| PREEMERGENCE | | | | | | | | | | | | | | | | | | | | |
| Barley | 0 | 0 | 0 | 0 | 0 | 0 | 0 | 0 | 0 | 1 | 0 | 0 | 0 | 2 | 2 | 0 | 0 | 5 | 0 | 7 |
| Barnyardgrass | 0 | 1 | 0 | 3 | 0 | 0 | 0 | 0 | 1 | 1 | 4 | 1 | 1 | 4 | 8 | 0 | 0 | 10 | 0 | 9 |
| Bedstraw | 4 | 9 | 6 | 9 | — | 0 | 0 | 2 | 1 | 5 | 9 | 8 | 5 | 4 | 7 | 0 | 0 | 8 | 2 | 10 |
| Blackgrass | 0 | 1 | 0 | 7 | 0 | 0 | 0 | 0 | 0 | 0 | 2 | 3 | 0 | 9 | 9 | 0 | 0 | 10 | 1 | 10 |
| Chickweed | 2 | 8 | 2 | 10 | 0 | 0 | 1 | 0 | 0 | 7 | 8 | 9 | 2 | 9 | 8 | 0 | 0 | 9 | 1 | 10 |
| Cocklebur | 0 | 0 | 0 | 4 | 0 | 0 | — | 0 | 0 | 0 | 0 | 0 | 0 | 0 | 2 | 0 | 0 | 1 | 0 | 7 |
| Corn | 0 | 1 | 0 | 1 | 0 | 0 | 0 | 0 | 0 | 0 | 0 | 0 | 0 | 2 | 1 | 0 | 0 | 3 | 0 | 3 |
| Cotton | 1 | 2 | 0 | 8 | 0 | 2 | 0 | 0 | 0 | 2 | 2 | 2 | 0 | 2 | 2 | 0 | 0 | 6 | 1 | 6 |
| Crabgrass | 4 | 9 | 5 | 9 | 0 | 6 | 6 | 0 | 8 | 9 | 9 | 9 | 4 | 10 | 10 | 0 | 1 | 10 | 5 | 10 |
| Downy brome | 2 | 1 | 0 | 3 | 0 | 0 | 0 | 0 | 0 | 1 | 1 | 1 | 0 | 1 | 8 | 0 | 0 | 10 | 0 | 10 |
| Giant foxtail | 4 | 7 | 7 | 9 | 0 | 3 | 4 | 0 | 2 | 8 | 9 | 9 | 7 | 10 | 9 | 0 | 1 | 10 | 3 | 10 |
| Lambsquarter | 6 | 9 | 0 | 10 | 0 | 2 | 7 | 0 | 7 | 4 | 10 | 9 | 10 | 9 | 9 | 0 | 0 | 10 | 8 | 10 |
| Morningglory | 0 | 3 | 1 | 10 | 0 | 0 | 0 | 0 | 0 | 2 | 3 | 2 | 0 | 2 | 3 | 0 | 0 | 9 | — | 9 |
| Nutsedge | — | — | 0 | 8 | — | 0 | — | 0 | — | — | — | — | 0 | 0 | 0 | 0 | 0 | 0 | 0 | 0 |
| Rape | 6 | 2 | 4 | 8 | 0 | 3 | 2 | 2 | 8 | 7 | 9 | 9 | 1 | 9 | 5 | 0 | 0 | 9 | 3 | 10 |
| Rice | 0 | 0 | 0 | 0 | 0 | 0 | 0 | 0 | 0 | 0 | 0 | 0 | 0 | 1 | 0 | 0 | 0 | 3 | 0 | 2 |
| Sorghum | 0 | 0 | 0 | 1 | 0 | 0 | 0 | 0 | 0 | 0 | 0 | 0 | 0 | 4 | 4 | 0 | 0 | 8 | 0 | 8 |

TABLE A-continued

| | COMPOUND | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| Soybean | 0 | 0 | 0 | 1 | 0 | 0 | 0 | 0 | 0 | 1 | 0 | 1 | 0 | 0 | 1 | 0 | 0 | 1 | 0 | 3 | | | | | | | | | |
| Sugar beet | 8 | 7 | 3 | 10 | 0 | 1 | 6 | 1 | 0 | 10 | 10 | 10 | 8 | 9 | 7 | 0 | 0 | 10 | 8 | 10 | | | | | | | | | |
| Velvetleaf | 0 | 3 | 2 | 8 | 0 | 2 | 0 | 0 | 0 | 9 | 5 | 3 | 2 | 3 | 4 | 0 | 0 | 10 | 2 | 8 | | | | | | | | | |
| Wheat | 0 | 0 | 0 | 0 | 0 | 0 | 0 | 0 | 0 | 0 | 0 | 0 | 0 | 1 | 2 | 0 | 0 | 8 | 0 | 8 | | | | | | | | | |
| Wild buckwheat | 0 | 1 | 0 | 3 | 0 | 0 | 1 | 0 | 0 | 4 | 3 | 2 | 0 | 3 | 3 | 0 | 0 | 6 | 1 | 8 | | | | | | | | | |
| Wild oat | 0 | 3 | 0 | 8 | 0 | 0 | 0 | 0 | 0 | 3 | 4 | 3 | 0 | 8 | 7 | 0 | 0 | 10 | 0 | 9 | | | | | | | | | |

| Rate 1000 g/ha | 14 | 20 | 23 | 25 | 26 | 27 | 28 | 29 | 30 | 31 | 32 | 33 | 34 | 35 | 36 | 38 | 39 | 40 | 41 | 42 | 44 | 45 | 46 | 47 | 48 | 49 | 50 | 53 | 54 |
|---|---|---|---|---|---|---|---|---|---|---|---|---|---|---|---|---|---|---|---|---|---|---|---|---|---|---|---|---|---|
| POSTEMERGENCE | | | | | | | | | | | | | | | | | | | | | | | | | | | | | |
| Barley | 0 | 4 | 3 | 2 | 3 | 2 | 3 | 0 | 3 | 4 | 3 | 4 | 4 | 5 | 7 | 2 | 2 | 1 | 3 | 4 | 3 | 3 | 3 | 4 | 4 | 2 | 3 | 2 | 3 |
| Barnyardgrass | 0 | 9 | 7 | 3 | 9 | 2 | 5 | 2 | 8 | 4 | 3 | 2 | 3 | 7 | 9 | 4 | 1 | 2 | 2 | 9 | 7 | 5 | 7 | 9 | 9 | 1 | 4 | 5 | 2 |
| Bedstraw | 0 | 8 | 6 | 7 | 9 | 7 | 9 | 3 | 8 | 7 | 8 | 9 | 6 | 9 | 9 | 8 | 4 | 2 | 4 | 7 | 8 | 9 | 9 | 9 | 7 | 6 | 8 | 9 | 4 |
| Blackgrass | 0 | 4 | 2 | 2 | 3 | 2 | 3 | 0 | 5 | 3 | 3 | 4 | 3 | 4 | 6 | 2 | 1 | 1 | 1 | 3 | 2 | 2 | 2 | 3 | 2 | 2 | 4 | 2 | 3 |
| Chickweed | 0 | 6 | 6 | 5 | 8 | 5 | 7 | 2 | 8 | 6 | 6 | 5 | 5 | 8 | 7 | 2 | 2 | 1 | 3 | 6 | 2 | 8 | 8 | 7 | 3 | 7 | 5 | 3 | 4 |
| Cocklebur | 0 | 7 | 7 | 8 | 6 | 5 | 7 | 3 | 7 | 7 | 8 | 8 | 8 | 8 | 9 | 6 | 4 | 5 | 7 | 7 | 6 | 5 | 7 | 7 | 6 | 4 | 6 | 8 | 2 |
| Corn | 0 | 2 | 2 | 2 | 4 | 2 | 2 | 2 | 4 | 4 | 5 | 1 | 2 | 4 | 3 | 2 | 3 | 2 | 1 | 4 | 1 | 4 | 5 | 5 | 3 | 1 | 3 | 3 | 1 |
| Cotton | 0 | 10 | 9 | 9 | 10 | 7 | 8 | 7 | 8 | 7 | 10 | 10 | 9 | 10 | 10 | 9 | 8 | 9 | 8 | 10 | 10 | 10 | 10 | 10 | 9 | 9 | 7 | 9 | 9 |
| Crabgrass | 0 | 6 | 8 | 3 | 9 | 8 | 9 | 2 | 8 | 8 | 6 | 2 | 5 | 7 | 8 | 4 | 3 | 3 | 4 | 8 | 3 | 3 | 5 | 7 | 5 | 2 | 4 | 4 | 2 |
| Downy brome | 0 | 3 | 2 | 2 | 3 | 3 | 3 | 0 | 4 | 2 | 1 | 2 | 2 | 3 | 3 | 1 | 1 | 1 | 1 | 2 | 2 | 1 | 2 | 3 | 2 | 1 | 3 | 1 | 3 |
| Giant foxtail | 0 | 8 | 9 | 5 | 9 | 6 | 9 | 2 | 9 | 9 | 7 | 4 | 5 | 9 | 8 | 3 | 3 | 3 | 3 | 6 | 3 | 4 | 5 | 7 | 3 | 3 | 4 | 3 | 1 |
| Lambsquarter | 0 | 9 | 7 | 8 | 9 | 9 | 9 | — | 9 | 8 | 8 | 7 | 8 | 10 | 8 | 7 | 3 | 4 | 7 | 7 | 7 | 9 | 9 | 8 | 6 | 5 | 8 | 6 | 7 |
| Morningglory | 0 | 8 | 6 | 3 | 8 | 3 | 8 | 1 | 8 | 9 | 7 | 2 | 7 | 9 | 8 | 4 | 4 | 4 | 5 | 5 | 3 | 5 | 4 | 8 | 6 | 3 | 8 | 6 | 2 |
| Nutsedge | 0 | 0 | 0 | 0 | 0 | — | 2 | 0 | — | 0 | 0 | 0 | 3 | 2 | 2 | 7 | 1 | — | 3 | 3 | 2 | 8 | 7 | 3 | 4 | 6 | 3 | 3 | 1 |
| Rape | 0 | 7 | 7 | 7 | 9 | 9 | 9 | 3 | 8 | 8 | 9 | 8 | 7 | 8 | 8 | 7 | 3 | 4 | 4 | 9 | 5 | 9 | 9 | 9 | 8 | 4 | 6 | 8 | 4 |
| Rice | 0 | 2 | 3 | 2 | 2 | 2 | 4 | 1 | 3 | 4 | 3 | 2 | 3 | 3 | 3 | 3 | 1 | 3 | 3 | 4 | 3 | 2 | 4 | 5 | 3 | 2 | 3 | 3 | 2 |
| Sorghum | 0 | 5 | 6 | 1 | 3 | 1 | 3 | 1 | 3 | 2 | 3 | 2 | 4 | 6 | 7 | 3 | 3 | 3 | 3 | 5 | 3 | 3 | 5 | 7 | 3 | 2 | 3 | 3 | 1 |
| Soybean | 0 | 8 | 8 | 7 | 6 | 5 | 6 | 3 | 7 | 6 | 4 | 6 | 3 | 8 | 8 | 6 | 6 | 4 | 5 | 5 | 7 | 7 | 5 | 8 | 8 | 4 | 8 | 7 | 4 |
| Sugar beet | 0 | 8 | 7 | 8 | 10 | 10 | 9 | 8 | 10 | 9 | 10 | 9 | 6 | 8 | 10 | 8 | 4 | 4 | 8 | 9 | 9 | 9 | 10 | 9 | 10 | 9 | 10 | 9 | 5 |
| Velvetleaf | 0 | 8 | 6 | 4 | 3 | 2 | 8 | 3 | 7 | 7 | 7 | 8 | 7 | 8 | 8 | 3 | 6 | 4 | 6 | 7 | 5 | 7 | 7 | 8 | 8 | 6 | 5 | 8 | 3 |
| Wheat | 0 | 3 | 2 | 2 | 2 | 2 | 3 | 0 | 2 | 2 | 1 | 2 | 1 | 3 | 2 | 2 | 2 | 2 | 2 | 3 | 1 | 2 | 2 | 3 | 3 | 1 | 2 | 1 | 4 |
| Wild buckwheat | 0 | 4 | 6 | 6 | 8 | 10 | 10 | 1 | 8 | 5 | 7 | 7 | 7 | 9 | 6 | 3 | 2 | 2 | 3 | 8 | 3 | 6 | 6 | 8 | 3 | 4 | 3 | 3 | 3 |
| Wild oat | 0 | 4 | 4 | 3 | 5 | 2 | 4 | 0 | 5 | 4 | 2 | 3 | 3 | 5 | 5 | 2 | 1 | 2 | 2 | 3 | 2 | 2 | 3 | 5 | 4 | 2 | 4 | 2 | 2 |

| Rate 1000 g/ha | 55 | 56 | 57 | 58 | 60 | 61 | 62 | 63 | 64 | 65 | 67 | 68 | 69 | 70 | 71 | 72 | 74 | 75 | 76 | 77 | 78 | 79 | 81 | 82 | 83 | 84 | 85 | 86 | 87 |
|---|---|---|---|---|---|---|---|---|---|---|---|---|---|---|---|---|---|---|---|---|---|---|---|---|---|---|---|---|---|
| POSTEMERGENCE | | | | | | | | | | | | | | | | | | | | | | | | | | | | | |
| Barley | 2 | 1 | 1 | 2 | 2 | 4 | 3 | 0 | 4 | 4 | 3 | 0 | 3 | 3 | 4 | 4 | 0 | 0 | 0 | 5 | 3 | 5 | 3 | 3 | 2 | 1 | 2 | 0 | 0 |
| Barnyardgrass | 5 | 4 | 3 | 2 | 2 | 5 | 4 | 1 | 5 | 8 | 6 | 0 | 4 | 8 | 10 | 6 | 0 | 0 | 0 | 6 | 3 | 5 | 2 | 7 | 2 | 1 | 2 | 3 | 1 |
| Bedstraw | 8 | 8 | 4 | 4 | — | — | — | — | — | — | — | 0 | — | 9 | 9 | 9 | 0 | 0 | 0 | 8 | 7 | 7 | 5 | 9 | 6 | 3 | 2 | 2 | 1 |
| Blackgrass | 5 | 3 | 2 | 1 | 5 | 7 | — | — | — | 4 | 3 | 0 | 4 | 6 | 9 | 4 | 0 | 0 | 0 | 5 | 3 | 5 | 3 | 3 | 1 | 2 | 0 | 0 | 0 |
| Chickweed | 7 | 3 | 2 | 3 | 6 | 7 | 6 | 0 | 5 | 7 | 7 | 0 | 5 | 9 | 9 | 6 | 0 | 0 | 0 | 6 | 5 | 8 | 4 | 6 | 3 | 2 | 1 | 1 | 0 |
| Cocklebur | 4 | 6 | 5 | 6 | 3 | 5 | 4 | 0 | 7 | 9 | 6 | 0 | 4 | 7 | 7 | 7 | 0 | 0 | 0 | 8 | 7 | 9 | 3 | 6 | 4 | 3 | 2 | 5 | 0 |
| Corn | 1 | 3 | 3 | 2 | 2 | 2 | 2 | 1 | 2 | 3 | 6 | 0 | 2 | 2 | 4 | 4 | 0 | 0 | 0 | 4 | 3 | 5 | 2 | 5 | 2 | 2 | 1 | 2 | 1 |
| Cotton | 10 | 7 | 3 | 5 | 5 | 9 | 9 | 3 | 9 | 10 | 8 | 0 | 7 | 9 | 10 | 10 | 0 | 0 | 0 | 6 | 8 | 10 | 6 | 4 | 9 | 4 | 1 | 2 | 0 |
| Crabgrass | 3 | 4 | 3 | 4 | 3 | 3 | 3 | 2 | 2 | 4 | 3 | 0 | 2 | 3 | 7 | 5 | 1 | 0 | 0 | 7 | 4 | 6 | 3 | 3 | 2 | 2 | 2 | 2 | 1 |
| Downy brome | 4 | 2 | 3 | 1 | 2 | 5 | 3 | 0 | 4 | 5 | 3 | 0 | 2 | 3 | 8 | 5 | 0 | 0 | 0 | 4 | 2 | 5 | 2 | 2 | 1 | 1 | 0 | 0 | 0 |
| Giant foxtail | 3 | 3 | 2 | 3 | 2 | 2 | 2 | 1 | 3 | 6 | 3 | 0 | 3 | 3 | 5 | 4 | 0 | 0 | 0 | 6 | 4 | 6 | 3 | 4 | 1 | 2 | 1 | 2 | 1 |

TABLE A-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Lambsquarter | 6 | 8 | 3 | 2 | 7 | 8 | 7 | 0 | 8 | 9 | 8 | 0 | 8 | 9 | 9 | 9 | 0 | 0 | 0 | 8 | 7 | 9 | 6 | 8 | 6 | 6 | 3 | 3 | 2 |
| Morningglory | 2 | 5 | 5 | 6 | 3 | 6 | 6 | 2 | 8 | 5 | 3 | 0 | 3 | 8 | 8 | 8 | 0 | 0 | 0 | 7 | 6 | 6 | 2 | 7 | 3 | 2 | 2 | 4 | 3 |
| Nutsedge | 0 | 3 | 2 | 2 | 1 | 0 | 1 | 0 | 1 | 0 | 3 | 0 | 2 | — | — | — | 0 | 0 | — | 4 | 3 | 3 | 1 | 2 | — | — | 0 | 0 | 0 |
| Rape | 5 | 6 | 6 | 7 | 6 | 8 | 7 | 0 | 6 | 9 | 9 | 0 | 6 | 9 | 10 | 9 | 0 | 0 | 0 | 8 | 8 | 9 | 4 | 7 | 7 | 5 | 4 | 3 | 1 |
| Rice | 2 | 3 | 4 | 2 | 2 | 2 | 3 | 0 | 3 | 4 | 3 | 0 | 3 | 2 | 4 | 4 | 0 | 0 | 0 | 4 | 3 | 3 | 2 | 3 | 1 | 1 | 0 | 2 | 0 |
| Sorghum | 2 | 2 | 2 | 1 | 2 | 2 | 2 | 0 | 2 | 5 | 5 | 0 | 1 | 2 | 4 | 3 | 0 | 0 | 0 | 3 | 2 | 4 | 2 | 5 | 2 | 1 | 1 | 1 | 0 |
| Soybean | 5 | 1 | 3 | 2 | 6 | 6 | 4 | 2 | 5 | 6 | 6 | 0 | 4 | 7 | 8 | 7 | 0 | 0 | 0 | 7 | 3 | 5 | 5 | 3 | 6 | 4 | 3 | 6 | 3 |
| Sugar beet | 8 | 8 | 9 | 8 | 7 | 8 | 9 | 0 | 9 | 9 | 10 | 0 | 9 | 9 | 10 | 9 | 0 | 0 | 0 | 9 | 8 | 8 | 7 | 9 | 8 | 8 | 4 | 6 | 4 |
| Velvetleaf | 4 | 6 | 5 | 5 | 2 | 5 | 6 | 1 | 6 | 8 | 7 | 0 | 3 | 6 | 9 | 9 | 0 | 0 | 0 | 7 | 7 | 8 | 2 | 8 | 3 | 2 | 1 | 2 | 0 |
| Wheat | 4 | 3 | 1 | 1 | 2 | 2 | 2 | 0 | 3 | 3 | 3 | 0 | 3 | 2 | 4 | 2 | 0 | 0 | 0 | 4 | 2 | 3 | 1 | 1 | 2 | 1 | 0 | 0 | 0 |
| Wild buckwheat | 4 | 2 | 2 | 3 | 5 | 8 | 6 | 2 | 6 | 9 | 5 | 0 | 7 | 7 | 7 | 7 | 0 | 0 | 0 | 7 | 5 | 7 | 4 | 8 | 2 | 4 | 2 | 2 | 1 |
| Wild oat | 3 | 2 | 1 | 2 | 3 | 4 | 4 | 0 | 5 | 5 | 4 | 0 | 3 | 3 | 7 | 5 | 0 | 0 | 0 | 5 | 3 | 5 | 3 | 3 | 2 | 2 | 0 | 0 | 0 |
| Rate 1000 g/ha | 88 | 89 | 90 | 91 | 92 | 93 | 94 | 95 | 96 | 97 | 98 | 99 | 100 | 101 | 102 | 103 | 104 | 105 | | | | | | | | | | | |
| POSTEMERGENCE | | | | | | | | | | | | | | | | | | | | | | | | | | | | | |
| Barley | 0 | 5 | 4 | 3 | 0 | 1 | 2 | 3 | 2 | 9 | 4 | 7 | 9 | 7 | 6 | 2 | 3 | 0 | | | | | | | | | | | |
| Barnyardgrass | 2 | 9 | 10 | 7 | 3 | 3 | 4 | 2 | 2 | 9 | 6 | 8 | 10 | 8 | 4 | 2 | 2 | 0 | | | | | | | | | | | |
| Bedstraw | 3 | 9 | 9 | — | 8 | 6 | 8 | 7 | 2 | 9 | 9 | 9 | 9 | 9 | 8 | 7 | 4 | 2 | | | | | | | | | | | |
| Blackgrass | 0 | 4 | 7 | 5 | 3 | 1 | 4 | 2 | 1 | 9 | 6 | 7 | 9 | 6 | 4 | 1 | 2 | 0 | | | | | | | | | | | |
| Chickweed | 1 | 9 | 8 | 6 | 3 | 4 | 4 | 3 | 3 | 10 | 7 | 9 | 9 | 8 | 7 | 4 | 3 | 0 | | | | | | | | | | | |
| Cocklebur | 3 | 9 | 9 | 8 | 7 | 6 | 7 | 8 | 4 | 9 | 9 | 9 | 10 | 9 | 9 | 2 | 3 | 0 | | | | | | | | | | | |
| Corn | 2 | 4 | 4 | 2 | 2 | 3 | 2 | 2 | 2 | 4 | 4 | 4 | 3 | 3 | 3 | 1 | 2 | 0 | | | | | | | | | | | |
| Cotton | 3 | 10 | 9 | 10 | 4 | 4 | 8 | 9 | 4 | 9 | 10 | 9 | 10 | 10 | 10 | 5 | 4 | 0 | | | | | | | | | | | |
| Crabgrass | 2 | 9 | 9 | 4 | 4 | 3 | 4 | 2 | 2 | 9 | 8 | 9 | 10 | 9 | 6 | 2 | 2 | 0 | | | | | | | | | | | |
| Downy brome | 0 | 3 | 4 | 3 | 1 | 2 | 2 | 1 | 0 | 9 | 5 | 6 | 9 | 6 | 4 | 1 | 1 | 0 | | | | | | | | | | | |
| Giant foxtail | 2 | 8 | 8 | 4 | 3 | 3 | 2 | 1 | 1 | 9 | 6 | 7 | 9 | 7 | 5 | 1 | 1 | 0 | | | | | | | | | | | |
| Lambsquarter | 3 | 9 | 9 | 8 | 8 | 7 | 7 | 8 | 4 | 9 | 9 | 9 | 9 | 9 | 8 | 7 | 5 | 4 | | | | | | | | | | | |
| Morningglory | 3 | 9 | 9 | 6 | 7 | 4 | 7 | 4 | 4 | 9 | 9 | 9 | 10 | 10 | 10 | 3 | 2 | 1 | | | | | | | | | | | |
| Nutsedge | 0 | 2 | 3 | 2 | 1 | 0 | 1 | 1 | 0 | 2 | 1 | 2 | 4 | 1 | 2 | — | 0 | 0 | | | | | | | | | | | |
| Rape | 3 | 10 | 9 | 8 | 6 | 6 | 4 | 7 | 2 | 9 | 8 | 9 | 10 | 10 | 8 | 5 | 5 | 0 | | | | | | | | | | | |
| Rice | 1 | 3 | 4 | 3 | 2 | 3 | 1 | 2 | 1 | 6 | 3 | 6 | 5 | 3 | 2 | 1 | 1 | 0 | | | | | | | | | | | |
| Sorghum | 1 | 8 | 6 | 5 | 3 | 3 | 2 | 2 | 1 | 5 | 5 | 4 | 8 | 4 | 3 | 1 | 1 | 0 | | | | | | | | | | | |
| Soybean | 3 | 8 | 9 | 8 | 3 | 5 | 7 | 6 | 3 | 8 | 8 | 7 | 9 | 8 | 8 | 4 | 4 | 1 | | | | | | | | | | | |
| Sugar beet | 4 | 9 | 10 | 9 | 7 | 6 | 9 | 9 | 4 | 10 | 9 | 9 | 10 | 10 | 9 | 5 | 5 | 2 | | | | | | | | | | | |
| Velvetleaf | 4 | 9 | 10 | 9 | 6 | 5 | 5 | 3 | 3 | 9 | 9 | 8 | 10 | 9 | 9 | 2 | 2 | 0 | | | | | | | | | | | |
| Wheat | 0 | 2 | 2 | 3 | 1 | 1 | 1 | 2 | 1 | 5 | 2 | 3 | 5 | 4 | 3 | 1 | 0 | 0 | | | | | | | | | | | |
| Wild buckwheat | 3 | 8 | 7 | 6 | 5 | 6 | 3 | 2 | 2 | 7 | 7 | 7 | 9 | 7 | 6 | 3 | 4 | 2 | | | | | | | | | | | |
| Wild oat | 1 | 7 | 6 | 3 | 2 | 2 | 3 | 2 | 1 | 9 | 5 | 4 | 9 | 7 | 4 | 1 | 1 | 0 | | | | | | | | | | | |
| Rate 1000 g/ha | 14 | 20 | 23 | 25 | 26 | 27 | 28 | 29 | 30 | 31 | 32 | 33 | 34 | 35 | 36 | 38 | 39 | 40 | 41 | 42 | 44 | 45 | 46 | 47 | 48 | 49 | 50 | 53 | 54 |
| PREEMERGENCE | | | | | | | | | | | | | | | | | | | | | | | | | | | | | |
| Barley | 0 | 4 | 1 | 1 | 2 | 0 | 1 | 0 | 3 | 2 | 2 | 3 | 0 | 2 | 5 | 2 | 1 | 1 | 1 | 4 | 3 | 3 | 3 | 8 | 4 | 2 | 4 | 2 | 0 |
| Barnyardgrass | 4 | 9 | 9 | 5 | 7 | 2 | 8 | 0 | 9 | 7 | 7 | 8 | 0 | 9 | 10 | 8 | 0 | 3 | 6 | 9 | 9 | 9 | 9 | 10 | 9 | 3 | 8 | 6 | 3 |
| Bedstraw | 0 | 8 | 8 | 5 | — | 2 | 3 | 0 | 5 | 6 | 4 | 4 | 0 | 9 | 10 | 3 | 4 | 1 | 2 | 9 | — | 0 | — | — | — | — | — | 3 | — |
| Blackgrass | 0 | 10 | 9 | 7 | 8 | 1 | 7 | 0 | 10 | 6 | 5 | 5 | 0 | 7 | 10 | 9 | 4 | 2 | 6 | 10 | 9 | 10 | 10 | 10 | 10 | 10 | 10 | 9 | 4 |
| Chickweed | 0 | 10 | 9 | — | — | 3 | 9 | 0 | 7 | 9 | 6 | 10 | 0 | 8 | 10 | 9 | 8 | 9 | 10 | 10 | — | 9 | 9 | 9 | 9 | — | — | 10 | 8 |

TABLE A-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Cocklebur | 0 | 1 | 2 | 0 | 0 | 0 | 0 | 0 | 2 | 2 | 0 | 2 | 0 | 2 | 8 | 0 | 0 | 0 | 6 | 6 | 5 | 3 | 7 | 1 | 1 | 1 | 1 | 5 | 0 |
| Corn | 0 | 1 | 4 | 1 | 1 | 0 | 1 | 0 | 2 | 2 | 2 | 1 | 0 | 2 | 3 | 2 | 0 | 0 | 1 | 3 | 2 | 2 | 5 | 5 | 3 | 0 | 2 | 1 | 0 |
| Cotton | 0 | — | 2 | 2 | 2 | 3 | 2 | 0 | 4 | 7 | 4 | 3 | 0 | 6 | 9 | 7 | 0 | 3 | 8 | 8 | 3 | — | 9 | 7 | 10 | 1 | 3 | 7 | 2 |
| Crabgrass | 4 | 10 | 10 | 10 | 10 | 7 | 10 | 3 | 10 | 9 | 8 | 10 | 3 | 10 | 10 | 9 | 9 | 9 | 10 | 10 | 10 | 10 | 10 | 10 | 10 | 10 | 10 | 10 | 9 |
| Downy brome | 0 | 9 | 2 | 4 | 9 | 0 | 4 | 0 | 5 | 5 | 3 | 8 | 0 | 3 | 10 | 9 | 2 | 2 | 4 | 10 | 7 | 10 | — | 10 | — | — | 10 | 10 | 0 |
| Giant foxtail | 0 | 10 | 10 | 10 | 10 | 9 | 10 | 0 | 10 | 9 | 9 | 10 | 5 | 10 | 10 | 10 | 9 | 8 | 9 | 10 | 10 | 10 | 10 | 10 | 10 | 10 | 10 | 9 | 9 |
| Lambsquarter | 0 | 10 | 10 | — | — | 3 | 10 | 0 | 9 | 9 | 8 | 9 | 0 | 10 | 9 | 10 | 2 | 8 | 10 | 10 | — | — | 10 | — | 10 | — | — | 10 | 4 |
| Morningglory | 0 | 5 | 8 | 2 | 3 | 2 | 3 | 1 | 3 | 8 | 7 | 4 | 0 | 9 | 8 | 4 | 1 | 3 | 9 | 6 | 3 | — | 8 | 4 | 8 | 4 | 4 | 7 | 2 |
| Nutsedge | — | 0 | 0 | 0 | 0 | 0 | 0 | — | — | — | — | 0 | 0 | 0 | 1 | 0 | 0 | 0 | 7 | 1 | 1 | 1 | 1 | 2 | 2 | 0 | 0 | 0 | 0 |
| Rape | 0 | 8 | 10 | 9 | 9 | 2 | 5 | 0 | 5 | 7 | 4 | 3 | 0 | 4 | 8 | 7 | 3 | 3 | 9 | 9 | 8 | 9 | 10 | 9 | 8 | — | 8 | 3 | 7 |
| Rice | 3 | 1 | 0 | 0 | 1 | 0 | 1 | 0 | 1 | 1 | 1 | 0 | 0 | 0 | 2 | 0 | 0 | 0 | 0 | 0 | 2 | 2 | 3 | 3 | 2 | 1 | 3 | 1 | 0 |
| Sorghum | 0 | 5 | 6 | 2 | 2 | 0 | 3 | 0 | 5 | 0 | 1 | 3 | 0 | 8 | 6 | 1 | 0 | 0 | 1 | 6 | 4 | 4 | 6 | 8 | 7 | 1 | 4 | 3 | 0 |
| Soybean | 2 | 1 | 3 | 0 | 1 | 0 | 1 | 0 | 0 | 2 | 1 | 0 | 0 | 3 | 6 | 1 | 0 | 1 | 2 | 3 | 3 | 3 | 3 | 2 | 4 | 1 | 1 | 0 | 0 |
| Sugar beet | 0 | 9 | 10 | — | 10 | 1 | 10 | 0 | 10 | 10 | 10 | 9 | 2 | 10 | 10 | 9 | 9 | 8 | 10 | 9 | 10 | 10 | 10 | 9 | 9 | — | 10 | 8 | 2 |
| Velvetleaf | 3 | 2 | 9 | 2 | 4 | 2 | 8 | 1 | 9 | 7 | 6 | 3 | 0 | 6 | 9 | 7 | 2 | 6 | 8 | 8 | 2 | 7 | 7 | 7 | 6 | 2 | 7 | 7 | 3 |
| Wheat | 0 | 3 | 0 | 0 | 1 | 0 | 1 | 0 | 2 | 2 | 2 | 2 | 0 | 3 | 4 | 2 | 0 | 1 | 2 | 3 | 2 | 2 | 4 | 9 | 4 | 4 | 2 | 2 | 0 |
| Wild buckwheat | 0 | 5 | 7 | — | 3 | 0 | 4 | 0 | 5 | 2 | 2 | 3 | 0 | 4 | 4 | 2 | 1 | 2 | 2 | 3 | — | 0 | 7 | — | 4 | — | 6 | 1 | 4 |
| Wild oat | 0 | 8 | 3 | 5 | 8 | 5 | 9 | 0 | 9 | 7 | 5 | 7 | 1 | 9 | 9 | 8 | 5 | 3 | 5 | 9 | 9 | 9 | 9 | 10 | 10 | 9 | 9 | 9 | 4 |
| Rate 1000 g/ha | 55 | 56 | 57 | 58 | 60 | 61 | 62 | 63 | 64 | 65 | 67 | 68 | 69 | 70 | 71 | 72 | 74 | 75 | 76 | 77 | 78 | 79 | 81 | 82 | 83 | 84 | 85 | 86 | 87 |
| PREEMERGENCE | | | | | | | | | | | | | | | | | | | | | | | | | | | | | |
| Barley | 6 | 3 | 0 | 2 | 2 | 5 | 5 | 0 | 5 | 6 | 2 | 0 | 3 | 4 | 8 | 6 | 0 | 0 | 0 | 0 | 2 | 3 | 0 | 4 | 0 | 0 | 0 | 0 | 0 |
| Barnyardgrass | 10 | 7 | 3 | 4 | 9 | 9 | 7 | 0 | 9 | 10 | 9 | 0 | 8 | 9 | 9 | 9 | 0 | 0 | 0 | 6 | 2 | 7 | 7 | 8 | 3 | 0 | 0 | 2 | 0 |
| Bedstraw | 10 | 10 | 9 | 10 | 3 | 3 | 10 | 0 | 9 | 10 | 10 | — | 10 | 10 | 8 | 7 | 0 | 0 | — | 5 | 8 | 3 | 4 | 10 | 2 | — | 0 | 2 | 0 |
| Blackgrass | 10 | 9 | 2 | 8 | 5 | 10 | 10 | 0 | 10 | 10 | 10 | 0 | 10 | 8 | 10 | 9 | 0 | 0 | 0 | 9 | 6 | 9 | 8 | 10 | 6 | 2 | 0 | 3 | 0 |
| Chickweed | 9 | 9 | 7 | 9 | 2 | 7 | 6 | 0 | 5 | 8 | 10 | 0 | 10 | 9 | 10 | 10 | 0 | 0 | 0 | 5 | 9 | 7 | 1 | 6 | 2 | 1 | 0 | 2 | 0 |
| Cocklebur | 2 | 4 | 0 | 1 | 0 | 0 | 2 | 0 | 1 | 9 | 1 | 0 | 2 | 2 | 3 | 1 | 0 | 0 | 0 | 0 | 0 | 1 | — | 1 | 0 | 0 | 0 | 0 | 0 |
| Corn | 1 | 2 | 0 | 1 | 0 | 2 | 1 | 0 | 1 | 2 | 1 | 0 | 1 | 1 | 3 | 1 | 0 | 0 | 0 | 0 | 0 | 0 | 1 | 4 | 0 | 0 | 0 | 0 | 0 |
| Cotton | 4 | 3 | 0 | 1 | 0 | 2 | 0 | 0 | 2 | 1 | 2 | 0 | 3 | 4 | 5 | 10 | 0 | 0 | 0 | 0 | 5 | 4 | 0 | 5 | 3 | 0 | 0 | 0 | 0 |
| Crabgrass | 10 | 10 | 9 | 10 | 10 | 10 | 10 | 0 | 10 | 10 | 10 | 0 | 10 | 10 | 10 | 9 | 0 | 0 | 0 | 9 | 9 | 9 | 10 | 10 | 9 | 2 | 1 | 6 | 1 |
| Downy brome | 10 | 10 | 0 | 8 | 2 | 10 | 10 | 0 | 10 | 10 | 10 | 0 | 10 | 10 | 10 | 10 | 0 | 0 | 0 | 6 | 5 | 8 | 3 | 6 | 1 | 0 | 0 | 1 | 0 |
| Giant foxtail | 10 | 10 | 9 | 9 | 9 | 10 | 9 | 0 | 10 | 10 | 10 | 0 | 9 | 9 | 10 | 9 | 0 | 0 | 0 | 7 | 9 | 9 | 8 | 10 | 7 | 2 | 1 | 8 | 0 |
| Lambsquarter | 10 | 9 | 0 | 9 | 10 | 10 | 10 | 0 | 9 | 10 | 10 | 0 | 10 | 10 | 9 | 9 | 0 | 0 | 0 | 8 | 9 | 6 | 7 | 10 | 4 | 1 | 0 | 1 | 0 |
| Morningglory | 3 | 5 | 1 | 2 | 2 | 3 | 4 | 0 | 3 | 5 | 4 | 0 | 4 | 3 | 8 | 4 | 0 | 0 | 0 | 3 | 9 | 5 | 1 | 8 | 3 | 0 | 0 | 0 | 0 |
| Nutsedge | — | 0 | 0 | 0 | 0 | 0 | 0 | 0 | 0 | 1 | — | 0 | 0 | — | — | — | — | — | — | — | — | — | 0 | — | 0 | — | 0 | 0 | 0 |
| Rape | 7 | 9 | 2 | 8 | 3 | 9 | 7 | 0 | 4 | 9 | 9 | 0 | 9 | 9 | 9 | 5 | 0 | 0 | 0 | 2 | 7 | 3 | 3 | 9 | 3 | 1 | 0 | 1 | 0 |
| Rice | 2 | 2 | 0 | 0 | 0 | 2 | 1 | 0 | 2 | 3 | 2 | 0 | 1 | 1 | 2 | 3 | 0 | 0 | 0 | 1 | 1 | 1 | 1 | 2 | 0 | 0 | 0 | 0 | 0 |
| Sorghum | 3 | 2 | 0 | 1 | 0 | 2 | 2 | 0 | 6 | 6 | 8 | 0 | 5 | 6 | 4 | 2 | 0 | 0 | 0 | 2 | 1 | 1 | 1 | 4 | 0 | 0 | 0 | 0 | 0 |
| Soybean | 2 | 1 | 0 | 0 | 0 | 0 | 0 | 0 | 1 | 0 | 0 | 0 | 1 | 1 | 1 | 2 | 0 | 0 | 0 | 0 | 0 | 1 | 1 | 1 | 0 | 0 | 0 | 0 | 0 |
| Sugar beet | 9 | 10 | 8 | 10 | 7 | 9 | 7 | 0 | 9 | 10 | 10 | 0 | 9 | 10 | 10 | 9 | 0 | 0 | 0 | 5 | 10 | 4 | 9 | 10 | 4 | 4 | 0 | 3 | 4 |
| Velvetleaf | 4 | 6 | 4 | 6 | 5 | 7 | 6 | 0 | 8 | 8 | 7 | 0 | 5 | 6 | 7 | 5 | 0 | 0 | 0 | 3 | 6 | 4 | 1 | 10 | 2 | 0 | 0 | 0 | 0 |
| Wheat | 5 | 2 | 0 | 1 | 0 | 4 | 3 | 0 | 4 | 4 | 3 | 0 | 5 | 5 | 8 | 6 | 0 | 0 | 0 | 1 | 3 | 3 | 0 | 4 | 0 | 0 | 0 | 0 | 0 |
| Wild buckwheat | 5 | 6 | 1 | 3 | 4 | 2 | 4 | 0 | 7 | 7 | 8 | 0 | 7 | 3 | 4 | 3 | 0 | 0 | 0 | 4 | 5 | 1 | 3 | 9 | 0 | 0 | 0 | 2 | 0 |
| Wild oat | 10 | 10 | 4 | 8 | 8 | 10 | 10 | 0 | 10 | 10 | 8 | 0 | 9 | 9 | 10 | 9 | 0 | 0 | 0 | 9 | 7 | 8 | 4 | 8 | 4 | 2 | 1 | 3 | 0 |

TABLE A-continued

| | COMPOUND | | | | | | | | | | | | | | | | | | | | | |
|---|---|---|---|---|---|---|---|---|---|---|---|---|---|---|---|---|---|---|---|---|---|---|
| Rate 1000 g/ha | 88 | 89 | 90 | 91 | 92 | 93 | 94 | 95 | 96 | 97 | 98 | 99 | 100 | 101 | 102 | 103 | 104 | 105 | | | | |
| PREEMERGENCE | | | | | | | | | | | | | | | | | | | | | | |
| Barley | 0 | 7 | 7 | 4 | 0 | 1 | 2 | 2 | 0 | 6 | 5 | 5 | 8 | 7 | 4 | 1 | 1 | 0 | | | | |
| Barnyardgrass | 1 | 9 | 10 | 9 | 4 | 7 | 9 | 8 | 1 | 9 | 8 | 9 | 10 | 9 | 4 | 0 | 0 | 0 | | | | |
| Bedstraw | 3 | 10 | 10 | 8 | 3 | 5 | 8 | — | 3 | 7 | 8 | 8 | 9 | 9 | 9 | 4 | 6 | 3 | | | | |
| Blackgrass | 4 | 10 | 10 | 9 | 5 | 6 | 10 | 9 | 0 | 10 | 10 | 10 | 10 | 10 | 7 | 1 | 2 | 0 | | | | |
| Chickweed | 2 | 9 | 9 | 9 | 7 | 7 | 8 | 9 | 2 | 9 | 8 | 9 | 9 | 10 | 10 | 7 | 6 | 0 | | | | |
| Cocklebur | 0 | 3 | 3 | 2 | 3 | — | 1 | 1 | 0 | 1 | 2 | 1 | 2 | 2 | 0 | 0 | 0 | 0 | | | | |
| Corn | 0 | 6 | 3 | 3 | 0 | 0 | 1 | 0 | 0 | 2 | 0 | 0 | 3 | 2 | 0 | 0 | 0 | 0 | | | | |
| Cotton | 0 | 6 | 7 | 3 | 0 | 4 | 3 | 3 | 1 | 6 | — | 3 | 10 | 8 | 3 | 0 | 0 | 0 | | | | |
| Crabgrass | 6 | 10 | 10 | 10 | 9 | 9 | 10 | 10 | 3 | 10 | 10 | 10 | 10 | 10 | 9 | 3 | 2 | 0 | | | | |
| Downy brome | 2 | 10 | 10 | 9 | 2 | 4 | 7 | 8 | 0 | 10 | 10 | 10 | 10 | 10 | 6 | 3 | 1 | 0 | | | | |
| Giant foxtail | 6 | 10 | 10 | 10 | 9 | 9 | 9 | 9 | 3 | 10 | 9 | 10 | 10 | 9 | 9 | 3 | 3 | 0 | | | | |
| Lambsquarter | 1 | 9 | 9 | 10 | 4 | 3 | 9 | 9 | 0 | 9 | 9 | 9 | 10 | 10 | 9 | 8 | 7 | 1 | | | | |
| Morningglory | 1 | 9 | 4 | 3 | 2 | 2 | 10 | 6 | 2 | 4 | 6 | 8 | 10 | 8 | 8 | 2 | 1 | 0 | | | | |
| Nutsedge | 0 | — | 2 | 0 | 0 | 0 | 0 | 0 | 0 | 0 | — | 0 | 0 | 0 | — | 0 | 0 | 0 | | | | |
| Rape | 2 | 9 | 10 | 9 | 7 | 6 | 6 | 6 | 0 | 6 | 2 | 3 | 10 | 9 | 9 | 7 | 4 | 0 | | | | |
| Rice | 0 | 3 | 3 | 2 | 0 | 0 | 1 | 1 | 0 | 5 | 3 | 3 | 2 | 3 | 1 | 0 | 0 | 0 | | | | |
| Sorghum | 0 | 8 | 8 | 8 | 2 | 2 | 1 | 1 | 0 | 7 | 3 | 6 | 6 | 4 | 2 | 0 | 0 | 0 | | | | |
| Soybean | 0 | 5 | 1 | 4 | 0 | 0 | 1 | 0 | 0 | 5 | 0 | 0 | 5 | 4 | 1 | 0 | 0 | 0 | | | | |
| Sugar beet | 3 | 9 | 10 | 9 | 6 | 7 | 9 | 7 | 0 | 10 | 9 | 7 | 10 | 10 | 9 | 7 | 7 | 4 | | | | |
| Velvetleaf | 1 | 7 | 6 | 3 | 1 | 3 | 4 | 6 | 1 | 7 | 5 | 4 | 9 | 8 | 7 | 5 | 3 | 0 | | | | |
| Wheat | 0 | 6 | 7 | 4 | 0 | 1 | 2 | 2 | 0 | 7 | 4 | 4 | 8 | 7 | 3 | 0 | 0 | 0 | | | | |
| Wild buckwheat | 1 | 7 | 10 | 5 | 2 | 3 | 3 | 4 | 0 | 6 | 6 | 6 | 9 | 7 | 3 | 0 | 1 | 1 | | | | |
| Wild oat | 1 | 10 | 10 | 9 | 3 | 5 | 7 | 7 | 0 | 10 | 9 | 9 | 9 | 9 | 8 | 4 | 3 | 0 | | | | |
| Rate 400 g/ha | 1 | 2 | 3 | 4 | 5 | 6 | 7 | 8 | 9 | 10 | 11 | 12 | 13 | 15 | 16 | 17 | 18 | 19 | 22 | 24 | 52 | 59 | 73 |
| POSTEMERGENCE | | | | | | | | | | | | | | | | | | | | | | |
| Barley | 0 | 0 | 0 | 0 | 0 | 0 | 0 | 0 | 0 | 0 | 0 | 0 | 0 | 1 | 3 | 0 | 0 | 4 | 0 | 3 | 3 | 3 | 3 |
| Barnyardgrass | 1 | 2 | 1 | 2 | 0 | 1 | 1 | 0 | 0 | 1 | 1 | 1 | 1 | 1 | 4 | 1 | 1 | 9 | 1 | 8 | 4 | 3 | 3 |
| Bedstraw | 3 | 5 | 2 | 7 | 0 | 3 | 1 | 0 | 0 | 4 | 4 | 2 | 1 | 4 | 6 | — | 2 | 8 | 1 | 9 | 7 | 9 | — |
| Blackgrass | 0 | 1 | 0 | 1 | 0 | 0 | 0 | 0 | 0 | 1 | 1 | 1 | 0 | 1 | 5 | — | 0 | 2 | 0 | 4 | 3 | 4 | 3 |
| Chickweed | 1 | 2 | 0 | 2 | 0 | 0 | 0 | 0 | 0 | 2 | 2 | 1 | 0 | 1 | 7 | — | 0 | 7 | 1 | 6 | 6 | 9 | 4 |
| Cocklebur | 2 | 5 | 2 | 5 | 0 | 3 | 1 | 0 | 0 | 2 | 6 | 3 | 2 | 2 | 6 | 2 | 2 | 9 | 3 | 6 | 8 | 5 | 6 |
| Corn | 1 | 2 | 1 | 2 | 0 | 2 | 1 | 0 | 1 | 1 | 2 | 2 | 2 | 1 | 2 | 1 | 1 | 3 | 2 | 1 | 2 | 2 | 3 |
| Cotton | 3 | 8 | 0 | 7 | 0 | 0 | 0 | 0 | 0 | 4 | 7 | 6 | 4 | 2 | 8 | 3 | 3 | 10 | 4 | 10 | 10 | 8 | 10 |
| Crabgrass | 2 | 2 | 1 | 2 | 0 | 1 | 1 | 0 | 1 | 1 | 2 | 2 | 2 | 2 | 4 | 1 | 1 | 9 | 2 | 9 | 2 | 2 | 3 |
| Downy brome | 0 | 0 | 0 | 0 | 0 | 0 | 0 | 0 | 0 | 0 | 0 | 0 | 0 | 1 | 3 | — | 0 | 1 | 0 | 3 | 2 | 2 | 2 |
| Giant foxtail | 2 | 2 | 1 | 2 | 0 | 1 | 0 | 0 | 0 | 1 | 1 | 2 | 1 | 2 | 5 | 1 | 1 | 9 | 1 | 9 | 3 | 2 | 3 |
| Lambsquarter | 2 | 2 | 1 | 3 | 0 | 1 | 2 | 0 | 1 | 2 | 2 | 2 | 1 | 6 | 7 | — | 2 | 9 | 2 | 9 | 8 | 9 | 8 |
| Morningglory | 2 | 2 | 2 | 3 | 0 | 1 | 2 | 0 | 1 | 1 | 2 | 2 | 1 | 2 | 3 | 2 | 3 | 9 | 3 | 5 | 8 | 3 | 4 |
| Nutsedge | 0 | 0 | 0 | 0 | 0 | 0 | 0 | 0 | 0 | — | 0 | 0 | 0 | 0 | 0 | 0 | 0 | 1 | 0 | 0 | 2 | 1 | 3 |
| Rape | 2 | 2 | 1 | 7 | 0 | 1 | 2 | 0 | 6 | 2 | 3 | 1 | 1 | 4 | 8 | 3 | 3 | 7 | 2 | 9 | 7 | 7 | 7 |
| Rice | 0 | 1 | 1 | 1 | 0 | 1 | 0 | 0 | 0 | 0 | 1 | 1 | 1 | 0 | 2 | 0 | 0 | 3 | 1 | 2 | 2 | 3 | 2 |
| Sorghum | 0 | 1 | 0 | 1 | 0 | 0 | 0 | 0 | 1 | 1 | 1 | 1 | 1 | 1 | 2 | 0 | 0 | 4 | 1 | 3 | — | 2 | 3 |
| Soybean | 1 | 1 | 2 | 1 | 0 | 0 | 0 | 0 | 1 | 2 | 0 | 0 | 2 | 2 | 7 | 3 | 0 | 9 | 3 | 8 | 4 | 6 | 6 |

TABLE A-continued

| | COMPOUND | | | | | | | | | | | | | | | | | | | | | | |
|---|---|---|---|---|---|---|---|---|---|---|---|---|---|---|---|---|---|---|---|---|---|---|---|
| Sugar beet | 3 | — | 4 | 8 | 0 | 2 | 3 | 0 | 1 | 4 | 6 | 6 | 5 | 4 | 9 | 3 | 3 | 8 | 6 | 10 | 8 | 7 | 7 |
| Velvetleaf | 1 | 2 | 1 | 4 | 0 | 1 | 1 | 0 | 0 | 2 | 4 | 1 | 0 | 2 | 8 | 2 | 1 | 9 | 2 | 7 | 3 | 8 | 4 |
| Wheat | 0 | 0 | 0 | 1 | 0 | 0 | 0 | 0 | 0 | 0 | 0 | 0 | 0 | 2 | 3 | 0 | 0 | 3 | 0 | 2 | 3 | 2 | 2 |
| Wild buckwheat | 1 | 1 | 1 | 2 | 0 | 1 | 1 | 0 | 1 | 3 | 2 | 2 | 1 | 3 | 5 | — | 2 | 8 | 2 | 7 | 7 | 6 | 3 |
| Wild oat | 0 | 0 | 0 | 1 | 0 | 0 | 0 | 0 | 0 | 1 | 0 | 0 | 0 | 1 | 4 | 0 | 0 | 3 | 0 | 5 | 3 | 4 | 3 |
| Rate 400 g/ha | 1 | 2 | 3 | 4 | 5 | 6 | 7 | 8 | 9 | 10 | 11 | 12 | 13 | 15 | 16 | 17 | 18 | 19 | 22 | 24 | 52 | 59 | 73 |
| PREEMERGENCE | | | | | | | | | | | | | | | | | | | | | | | |
| Barley | 0 | 0 | 0 | 0 | 0 | 0 | 0 | 0 | 0 | 0 | 0 | 0 | 0 | 0 | 1 | 0 | 0 | 3 | 0 | 3 | 0 | 3 | 1 |
| Barnyardgrass | 0 | 1 | 0 | 0 | 0 | 0 | 0 | 0 | 0 | 0 | 0 | 0 | 0 | 2 | 3 | 0 | 0 | 10 | 0 | 9 | 8 | 7 | 7 |
| Bedstraw | 1 | 5 | — | 9 | — | 0 | 0 | 0 | 0 | 2 | 2 | 7 | 0 | 1 | 3 | 0 | 0 | 8 | 0 | 7 | 7 | 9 | 7 |
| Blackgrass | 0 | 0 | 0 | 1 | 0 | 0 | 0 | 0 | 0 | 0 | 0 | 0 | 0 | 0 | 4 | 0 | 0 | 8 | 0 | 9 | 6 | 9 | 7 |
| Chickweed | 0 | 6 | 0 | 8 | 0 | 0 | 0 | 0 | 0 | 3 | 3 | 1 | 0 | 7 | 7 | 0 | 0 | 9 | 1 | 9 | 7 | 10 | 8 |
| Cocklebur | 0 | 0 | 0 | 0 | 0 | 0 | 0 | 0 | 0 | 0 | 0 | 0 | 0 | 0 | 1 | 0 | 0 | 0 | 0 | 1 | 0 | 0 | 4 |
| Corn | 0 | 0 | 0 | 0 | 0 | 0 | 0 | 0 | 0 | 0 | 0 | 0 | 0 | 2 | 0 | 0 | 0 | 1 | 0 | 1 | 1 | 1 | 0 |
| Cotton | 0 | 2 | 0 | 0 | 0 | 0 | 0 | 0 | 0 | 2 | 2 | 0 | 0 | 0 | 2 | 0 | 0 | 3 | 1 | 3 | 2 | 4 | 4 |
| Crabgrass | 1 | 8 | 3 | 9 | 0 | 1 | 1 | 0 | 1 | 3 | 8 | 9 | 1 | 8 | 7 | 0 | 0 | 10 | 2 | 10 | 9 | 9 | 9 |
| Downy brome | 0 | 0 | 0 | 2 | 0 | 0 | 0 | 0 | 0 | 0 | 0 | 0 | 0 | 1 | 1 | 0 | 0 | 6 | 0 | 8 | 5 | 5 | 6 |
| Giant foxtail | 1 | 6 | 3 | 9 | 0 | 1 | 1 | 0 | 0 | 2 | 9 | 8 | 2 | 6 | 8 | 0 | 0 | 10 | 2 | 10 | 9 | 9 | 7 |
| Lambsquarter | 0 | 9 | 0 | 9 | 0 | 0 | 0 | 0 | 0 | 4 | 7 | 6 | 0 | 5 | 6 | 0 | 0 | 9 | 6 | 9 | 9 | 7 | 8 |
| Morningglory | 0 | 2 | 0 | 1 | 0 | 0 | 0 | 0 | 0 | 0 | 2 | 1 | 0 | 2 | 1 | 0 | 0 | 5 | 0 | 8 | 6 | 2 | 6 |
| Nutsedge | 0 | 0 | — | — | 0 | — | 0 | — | — | 0 | — | 0 | 0 | 0 | 0 | 0 | 0 | 0 | 0 | 0 | 0 | 0 | 0 |
| Rape | 4 | 1 | 1 | 8 | 0 | 1 | 0 | 0 | 2 | 5 | 4 | 3 | 1 | 1 | 3 | 0 | 0 | 5 | 1 | 10 | 4 | 6 | 3 |
| Rice | 0 | 0 | 0 | 0 | 0 | 0 | 0 | 0 | 0 | 0 | 0 | 0 | 0 | 0 | 0 | 0 | 0 | 1 | 0 | 1 | 1 | 2 | 0 |
| Sorghum | 0 | 0 | 0 | 0 | 0 | 0 | 0 | 0 | 0 | 0 | 0 | 0 | 0 | 0 | 0 | 0 | 0 | 6 | 0 | 3 | 1 | 2 | 1 |
| Soybean | 0 | 0 | 0 | 0 | 0 | 0 | 0 | 0 | 0 | 0 | 0 | 0 | 0 | 0 | 0 | 0 | 0 | 0 | 0 | 2 | 0 | 0 | 1 |
| Sugar beet | 1 | 7 | 1 | 10 | 0 | 0 | 0 | 0 | 0 | 9 | 8 | 6 | 0 | 5 | 7 | 0 | 0 | 9 | 7 | 10 | 7 | 7 | 6 |
| Velvetleaf | 0 | 2 | 0 | 3 | 0 | 0 | 0 | 0 | 0 | 1 | 3 | 3 | 0 | 0 | 2 | 0 | 0 | 3 | 1 | 4 | 4 | 7 | 3 |
| Wheat | 0 | 0 | 0 | 0 | 0 | 0 | 0 | 0 | 0 | 0 | 0 | 0 | 0 | 0 | 0 | 0 | 0 | 3 | 0 | 4 | 2 | 2 | 1 |
| Wild buckwheat | 0 | 1 | 0 | 1 | 0 | 0 | 0 | 0 | 0 | 0 | 1 | 1 | 0 | 0 | 1 | 0 | 0 | 4 | 0 | 5 | 1 | 3 | 2 |
| Wild oat | 0 | 0 | 0 | 2 | 0 | 0 | 0 | 0 | 0 | 0 | 1 | 0 | 0 | 2 | 4 | 0 | 0 | 9 | 0 | 9 | 7 | 8 | 8 |

| Rate 200 g/ha | 14 | 20 | 23 | 25 | 26 | 27 | 28 | 29 | 30 | 31 | 32 | 33 | 34 | 35 | 36 | 38 | 39 | 40 | 41 | 42 | 44 | 45 | 46 | 47 | 48 | 49 | 50 | 53 | 54 |
|---|---|---|---|---|---|---|---|---|---|---|---|---|---|---|---|---|---|---|---|---|---|---|---|---|---|---|---|---|---|
| POSTEMERGENCE | | | | | | | | | | | | | | | | | | | | | | | | | | | | | |
| Barley | 0 | 3 | 3 | 1 | 3 | 0 | 1 | 0 | 2 | 2 | 2 | 3 | 2 | 3 | 7 | 1 | 1 | 1 | 1 | 3 | 3 | 1 | 2 | 4 | 2 | 2 | 2 | 2 | 2 |
| Barnyardgrass | 0 | 6 | 3 | 2 | 4 | 2 | 2 | 2 | 3 | 4 | 3 | 2 | 2 | 3 | 7 | 3 | 1 | 2 | 2 | 4 | 3 | 3 | 4 | 9 | 3 | 1 | 3 | 4 | 1 |
| Bedstraw | 0 | 8 | 5 | 7 | 7 | 6 | 4 | 2 | 7 | 7 | 7 | 8 | 4 | 9 | 7 | 8 | 3 | 2 | 4 | 8 | 7 | 8 | 5 | 7 | 7 | 6 | 7 | 8 | 4 |
| Blackgrass | 0 | 2 | 2 | 2 | 3 | 0 | 2 | 0 | 3 | 2 | 2 | 3 | 1 | 3 | 3 | 1 | 1 | 1 | 1 | 2 | 2 | 1 | 2 | 2 | 2 | 1 | 1 | 2 | 3 |
| Chickweed | 0 | 5 | 5 | 4 | 7 | 5 | 5 | 2 | 5 | 5 | 3 | 5 | 3 | 6 | 7 | 2 | 2 | 1 | 3 | 6 | 2 | 6 | 5 | 6 | 3 | 6 | 4 | — | 4 |
| Cocklebur | 0 | 7 | 6 | 6 | 6 | 4 | 6 | 2 | 6 | 7 | 8 | 5 | 4 | 8 | 9 | 5 | 4 | 4 | 6 | 7 | 2 | 5 | 6 | 6 | 6 | 5 | 6 | 8 | 2 |
| Corn | 0 | 1 | 2 | 1 | 1 | 2 | 1 | 2 | 2 | 4 | 3 | 1 | 1 | 1 | 2 | 2 | 1 | 1 | 2 | 3 | 1 | 2 | 2 | 3 | 2 | 1 | 3 | 2 | 1 |
| Cotton | 0 | 10 | 9 | 10 | 9 | 5 | 7 | 4 | — | 7 | 8 | 7 | 8 | 10 | 10 | 6 | 6 | 8 | 8 | 8 | 8 | 10 | 8 | 10 | 7 | 9 | 9 | 8 | 9 |
| Crabgrass | 0 | 4 | 3 | 2 | 6 | 2 | 3 | 1 | 6 | 5 | 5 | 2 | 2 | 4 | 7 | 3 | 3 | 3 | 4 | 4 | 3 | 2 | 3 | 4 | 4 | 2 | 4 | 3 | 2 |
| Downy brome | 0 | 2 | 1 | 2 | 2 | 2 | 3 | 0 | 2 | 1 | 1 | 2 | 1 | 2 | 2 | 1 | 1 | 1 | 1 | 1 | 1 | 1 | 1 | 2 | 1 | 2 | 1 | 1 | 2 |
| Giant foxtail | 0 | 5 | 7 | 3 | 7 | 2 | 3 | 1 | 3 | 6 | 5 | 2 | 2 | 6 | 5 | 3 | 3 | 3 | 3 | 4 | 3 | 2 | 3 | 4 | 3 | 2 | 3 | 3 | 1 |
| Lambsquarter | 0 | 7 | 6 | 6 | 6 | 8 | 9 | — | 9 | 7 | 8 | 6 | 7 | 9 | 7 | 4 | 3 | 3 | 5 | 7 | 5 | 8 | 7 | 6 | 6 | 5 | 8 | 6 | 6 |

TABLE A-continued

| COMPOUND | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Morningglory | 0 | 8 | 4 | 3 | 8 | 2 | 8 | 1 | 7 | 7 | 6 | 1 | 3 | 8 | 8 | 3 | 3 | 3 | 4 | 5 | 3 | 4 | 4 | 7 | 6 | 2 | 8 | 6 | 1 |
| Nutsedge | — | 0 | 0 | 0 | — | — | 1 | 0 | — | 0 | 0 | 0 | 0 | 1 | 2 | 6 | 0 | 0 | 0 | 2 | 1 | 1 | 3 | 3 | 3 | 1 | 3 | 2 | 0 |
| Rape | 0 | 7 | 4 | 6 | 9 | 4 | 8 | 2 | 8 | 8 | 8 | 7 | 6 | 7 | 8 | 7 | 3 | 1 | 6 | 8 | 5 | 9 | 9 | 9 | 6 | 4 | 5 | 6 | 4 |
| Rice | 0 | 2 | 1 | 2 | 2 | 2 | 2 | 0 | 3 | 4 | 3 | 2 | 3 | 3 | 2 | 1 | 0 | 0 | 1 | 3 | 2 | 2 | 3 | 4 | 3 | 1 | 3 | 2 | 1 |
| Sorghum | 0 | 2 | 2 | 1 | 2 | 1 | 1 | 0 | 1 | 2 | 2 | 2 | 3 | 5 | 4 | 3 | 2 | 2 | 2 | 3 | 2 | 2 | 2 | 3 | 2 | 2 | 3 | 3 | 1 |
| Soybean | 0 | 8 | 8 | 3 | 6 | 5 | 6 | 2 | 6 | 4 | 4 | 5 | 2 | 8 | 8 | 6 | 3 | 4 | 3 | 7 | 6 | 6 | 5 | 7 | 6 | 3 | 5 | 5 | 4 |
| Sugar beet | 0 | 8 | 5 | 7 | 9 | 8 | 9 | 2 | 10 | 9 | 8 | 8 | 3 | 8 | 9 | 7 | 3 | 3 | 8 | 9 | 8 | 9 | 9 | 9 | 8 | 7 | 8 | 8 | 5 |
| Velvetleaf | 0 | 8 | 4 | 3 | — | 1 | 2 | 1 | 5 | 6 | 6 | 2 | 6 | 7 | 7 | 3 | 3 | 4 | 4 | 4 | 2 | 5 | 7 | 7 | 4 | 3 | 6 | 8 | 1 |
| Wheat | 0 | 2 | 3 | 2 | 2 | 0 | 1 | 0 | 3 | 1 | 1 | 2 | 0 | 2 | 2 | 1 | 1 | 1 | 1 | 2 | 1 | 2 | 1 | 2 | 1 | 1 | 1 | 1 | 2 |
| Wild buckwheat | 0 | 4 | 4 | 2 | 7 | 3 | 9 | 1 | 7 | 5 | 7 | 6 | 7 | 7 | 5 | 2 | 1 | 2 | 2 | 6 | 2 | 4 | 6 | 6 | 2 | 3 | 3 | 2 | 3 |
| Wild oat | 0 | 3 | 2 | 1 | 3 | 1 | 2 | 0 | 3 | 2 | 2 | 3 | 1 | 4 | 4 | 1 | 1 | 2 | 2 | 2 | 2 | 2 | 2 | 3 | 2 | 2 | 2 | 2 | 2 |
| Rate 200 g/ha | 55 | 56 | 57 | 58 | 60 | 61 | 62 | 63 | 64 | 65 | 66 | 67 | 68 | 69 | 70 | 71 | 72 | 74 | 75 | 76 | 77 | 78 | 79 | 81 | 82 | 83 | 84 | 85 | 86 |
| POSTEMERGENCE | | | | | | | | | | | | | | | | | | | | | | | | | | | | | |
| Barley | 2 | 1 | 1 | 1 | 2 | 3 | 2 | 0 | 2 | 3 | 1 | 2 | 0 | 3 | 3 | 3 | 3 | 0 | 0 | 0 | 3 | 3 | 4 | 0 | 3 | 2 | 1 | 0 | 0 |
| Barnyardgrass | 3 | 3 | 2 | 3 | 2 | 3 | 3 | 1 | 3 | 5 | 1 | 3 | 0 | 3 | 3 | 9 | 5 | 0 | 0 | 0 | 5 | 3 | 4 | 2 | 3 | 1 | 1 | 1 | 2 |
| Bedstraw | 8 | 5 | 2 | — | — | — | — | 0 | — | — | — | 7 | 0 | — | — | — | 9 | 0 | 0 | 0 | 7 | 7 | 6 | 3 | 8 | 6 | 3 | 1 | 2 |
| Blackgrass | 4 | 2 | 1 | 1 | — | 5 | — | — | — | 2 | — | 2 | 0 | 1 | 3 | 7 | 4 | 0 | 0 | 0 | 4 | 1 | 4 | 2 | 2 | 1 | 0 | 0 | 0 |
| Chickweed | 7 | 3 | 2 | 2 | 4 | 5 | 4 | 0 | 4 | 6 | 3 | 4 | 0 | 5 | 5 | 8 | 6 | 0 | 0 | 0 | 5 | 5 | 5 | 4 | 4 | 2 | 2 | 0 | 1 |
| Cocklebur | 3 | 6 | 5 | 4 | 3 | 3 | 4 | 1 | 3 | 6 | 2 | 3 | 0 | 4 | 5 | 8 | 6 | 0 | 0 | 0 | 8 | 7 | 8 | 2 | 4 | 4 | 2 | 2 | 4 |
| Corn | 1 | 3 | 3 | 2 | 1 | 1 | 1 | 1 | 1 | 1 | 2 | 2 | 0 | 2 | 2 | 4 | 4 | 0 | 0 | 0 | 3 | 2 | 3 | 2 | 2 | 2 | 2 | 1 | 2 |
| Cotton | 9 | 9 | 1 | 3 | 3 | 8 | 8 | 0 | 9 | 6 | 4 | 8 | 0 | — | 5 | 10 | 10 | 0 | 0 | 0 | 4 | 7 | 7 | 3 | 3 | 3 | 2 | 1 | 2 |
| Crabgrass | 2 | 3 | 3 | 3 | 2 | 3 | 2 | 2 | 2 | 3 | 3 | 2 | 0 | 2 | 2 | 6 | 4 | 0 | 0 | 0 | 4 | 4 | 4 | 2 | 2 | 2 | 2 | 2 | 2 |
| Downy brome | 3 | 2 | 2 | 1 | 0 | 1 | 2 | 0 | 2 | 3 | 0 | 2 | 0 | 0 | 2 | 5 | 3 | 0 | 0 | 0 | 3 | 1 | 3 | 1 | 1 | 1 | 0 | 0 | 0 |
| Giant foxtail | 3 | 3 | 3 | 3 | 2 | 2 | 2 | 2 | 3 | 3 | 2 | 2 | 0 | 2 | 2 | 5 | 4 | 0 | 0 | 0 | 4 | 3 | 4 | 2 | 3 | 1 | 1 | 1 | 2 |
| Lambsquarter | 6 | 7 | 3 | 2 | 5 | 8 | 7 | 0 | 7 | 8 | 3 | 7 | 0 | 6 | 8 | 9 | 9 | 0 | 0 | 0 | 8 | 6 | 9 | 6 | 7 | 5 | 5 | 2 | 2 |
| Morningglory | 1 | 5 | 1 | 2 | 2 | 6 | 4 | 2 | 6 | 5 | 2 | 2 | 0 | 1 | 7 | 6 | 4 | 0 | 0 | 0 | 8 | 4 | 7 | 2 | 4 | 2 | 2 | 2 | 3 |
| Nutsedge | 0 | 2 | 0 | 2 | 0 | 0 | 0 | 0 | 0 | — | 0 | — | 0 | 0 | 0 | 8 | 4 | — | 0 | 0 | 3 | 3 | — | 0 | 2 | 0 | — | 0 | 0 |
| Rape | 5 | 6 | 2 | 7 | 6 | 6 | 7 | 0 | 6 | 7 | 7 | 9 | 0 | 6 | 7 | 9 | 9 | 0 | 0 | 0 | 8 | 7 | 6 | 2 | 7 | 6 | 4 | 3 | 2 |
| Rice | 1 | 3 | 3 | 3 | 2 | 2 | 2 | 0 | 3 | 3 | 3 | 2 | 0 | 2 | 2 | 4 | 3 | 0 | 0 | 0 | 4 | 2 | 3 | 1 | 2 | 1 | 1 | 0 | 2 |
| Sorghum | 1 | 2 | 1 | 2 | 1 | 2 | 2 | 0 | 2 | 2 | 1 | 2 | 0 | 1 | 2 | 4 | 3 | 0 | 0 | 0 | 3 | 2 | 2 | 2 | 2 | 1 | 2 | 0 | 1 |
| Soybean | 5 | 1 | 2 | 1 | 5 | 6 | 5 | 1 | 4 | 6 | 4 | 6 | 0 | 2 | 6 | 7 | 5 | 0 | 0 | 0 | 4 | 3 | 4 | 2 | 3 | 6 | 4 | 2 | 5 |
| Sugar beet | 7 | 7 | 9 | 8 | 7 | 8 | 6 | 0 | 7 | 9 | 4 | 10 | 0 | 9 | 9 | 9 | 9 | 0 | 0 | 0 | 8 | 7 | 7 | 6 | 9 | 8 | 8 | 3 | 6 |
| Velvetleaf | 2 | 5 | 3 | 6 | 2 | 5 | 3 | 1 | 6 | 4 | 1 | 3 | 0 | 3 | 6 | 9 | 7 | 0 | 0 | 0 | 6 | 7 | 8 | 1 | 6 | 1 | 2 | 1 | 2 |
| Wheat | 2 | 1 | 0 | 0 | 2 | 2 | 1 | 0 | 2 | 2 | 2 | 1 | 0 | 2 | 3 | 2 | 2 | 0 | 0 | 0 | 2 | 2 | 3 | 0 | 0 | 1 | 1 | 0 | 0 |
| Wild buckwheat | 4 | 2 | 2 | 3 | 5 | 7 | 5 | 2 | 5 | 6 | 4 | 2 | 0 | 5 | 7 | 7 | 4 | 0 | 0 | 0 | 3 | 5 | 3 | 2 | 6 | 2 | 4 | 2 | 2 |
| Wild oat | 3 | 2 | 1 | 1 | 3 | 2 | 3 | 0 | 2 | 3 | 3 | 3 | 0 | 2 | 3 | 5 | 5 | 0 | 0 | 0 | 4 | 3 | 4 | 1 | 3 | 2 | 1 | 0 | 0 |
| Rate 200 g/ha | 87 | 88 | 89 | 90 | 91 | 92 | 93 | 94 | 95 | 96 | 97 | 98 | 99 | 100 | 101 | 102 | 103 | 104 | 105 | | | | | | | | | | |
| POSTEMERGENCE | | | | | | | | | | | | | | | | | | | | | | | | | | | | | |
| Barley | 0 | 0 | 4 | 4 | 2 | 0 | 1 | 2 | 2 | 1 | 7 | 4 | 4 | 7 | 6 | 4 | 2 | 2 | 0 | | | | | | | | | | |
| Barnyardgrass | 1 | 2 | 6 | 9 | 5 | 2 | 2 | 3 | 2 | 2 | 8 | 4 | 6 | 8 | 6 | 3 | 2 | 2 | 0 | | | | | | | | | | |
| Bedstraw | 1 | 2 | 8 | 7 | 7 | 6 | 6 | 8 | 5 | 2 | 9 | 9 | 8 | 9 | 8 | 7 | 6 | 3 | 0 | | | | | | | | | | |
| Blackgrass | 0 | 0 | 4 | 7 | 5 | 1 | 2 | 2 | 2 | 0 | 9 | 4 | 2 | 7 | 4 | 2 | 1 | 0 | 0 | | | | | | | | | | |
| Chickweed | 0 | 0 | 6 | 8 | 4 | 3 | 4 | 2 | 2 | 1 | 7 | 7 | 7 | 8 | 7 | 5 | 3 | 2 | 0 | | | | | | | | | | |
| Cocklebur | 0 | 3 | 6 | 8 | 8 | 7 | 7 | 7 | 6 | 4 | 9 | 8 | 9 | 10 | 9 | 9 | 2 | 3 | 0 | | | | | | | | | | |

TABLE A-continued

| | COMPOUND | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| Corn | 0 | 1 | 3 | 3 | 2 | 2 | 3 | 2 | 2 | 2 | 3 | 4 | 3 | — | 2 | 2 | 1 | 2 | 0 | | | | | | | | | | |
| Cotton | 0 | 3 | 10 | 10 | 9 | 4 | 4 | 6 | 10 | 4 | 9 | 9 | 9 | 10 | 10 | 9 | 2 | 4 | 0 | | | | | | | | | | |
| Crabgrass | 1 | 2 | 3 | 6 | 3 | 4 | 4 | 3 | 2 | 2 | 9 | 5 | 6 | 8 | 7 | 4 | 2 | 1 | 0 | | | | | | | | | | |
| Downy brome | 0 | 0 | 3 | 4 | 3 | 1 | 1 | 2 | 1 | 1 | 6 | 3 | 3 | 6 | 5 | 3 | 1 | 1 | 0 | | | | | | | | | | |
| Giant foxtail | 1 | 1 | 4 | 6 | 3 | 3 | 3 | 2 | 1 | 1 | 7 | 3 | 3 | 8 | 4 | 3 | 1 | 1 | 0 | | | | | | | | | | |
| Lambsquarter | 2 | 2 | 9 | 8 | 8 | 6 | 6 | 7 | 3 | 3 | 9 | 8 | 9 | 9 | 8 | 7 | 6 | 5 | 3 | | | | | | | | | | |
| Morningglory | 2 | 2 | 9 | 8 | 6 | 6 | 4 | 6 | 5 | 2 | 9 | 7 | 9 | 9 | 10 | 9 | 3 | 2 | 1 | | | | | | | | | | |
| Nutsedge | 0 | 0 | 2 | — | 2 | 0 | 0 | 0 | 0 | 0 | 0 | 0 | 1 | 2 | 1 | 1 | 0 | 0 | 0 | | | | | | | | | | |
| Rape | 0 | 3 | 9 | 9 | 7 | 6 | 6 | — | 8 | 2 | 8 | 8 | 6 | 10 | 8 | 7 | 4 | 4 | 0 | | | | | | | | | | |
| Rice | 0 | 0 | 3 | 3 | 3 | 2 | 3 | 1 | 1 | 1 | 4 | 2 | 4 | 3 | 2 | 1 | 1 | 1 | 0 | | | | | | | | | | |
| Sorghum | 0 | 1 | 4 | 4 | 3 | 3 | 3 | 2 | 2 | 1 | 4 | 3 | 3 | 8 | 3 | 2 | 0 | 1 | 0 | | | | | | | | | | |
| Soybean | 2 | 3 | 8 | 8 | 6 | 3 | 5 | 5 | 6 | 3 | 8 | 7 | 6 | 9 | 7 | 7 | 4 | 3 | 0 | | | | | | | | | | |
| Sugar beet | 0 | 4 | 9 | 9 | 9 | 6 | 6 | 8 | 9 | 3 | 9 | 9 | 8 | 10 | 10 | 8 | 4 | 5 | 0 | | | | | | | | | | |
| Velvetleaf | 0 | 3 | 8 | 9 | 8 | 5 | 4 | 4 | 2 | 2 | 9 | 9 | 7 | 10 | 9 | 9 | 1 | 1 | 0 | | | | | | | | | | |
| Wheat | 0 | 0 | 2 | 2 | 1 | 1 | 1 | 0 | 1 | 0 | 2 | 2 | 2 | 4 | 3 | 2 | 1 | 0 | 0 | | | | | | | | | | |
| Wild buckwheat | 1 | 2 | 6 | 4 | 5 | 4 | 4 | 2 | 2 | 1 | 5 | 7 | 7 | 8 | 7 | 6 | 3 | 3 | 0 | | | | | | | | | | |
| Wild oat | 0 | 1 | 5 | 4 | 3 | 2 | 2 | 2 | 2 | 1 | 5 | 4 | 4 | 6 | 5 | 3 | 0 | 1 | 0 | | | | | | | | | | |
| Rate 200 g/ha | 14 | 20 | 23 | 25 | 26 | 27 | 28 | 29 | 30 | 31 | 32 | 33 | 34 | 35 | 36 | 38 | 39 | 40 | 41 | 42 | 44 | 45 | 46 | 47 | 48 | 49 | 50 | 53 | 54 |
| PREEMERGENCE | | | | | | | | | | | | | | | | | | | | | | | | | | | | | |
| Barley | 0 | 2 | 0 | 0 | 1 | 0 | 0 | 0 | 0 | 0 | 1 | 0 | 0 | 0 | 3 | 0 | 0 | 0 | 0 | 1 | 0 | 2 | 2 | 2 | 2 | 1 | 2 | 1 | 0 |
| Barnyardgrass | 0 | 6 | 7 | 0 | 2 | 0 | 2 | 0 | 2 | 0 | 0 | 0 | 0 | 8 | 9 | 4 | 0 | 0 | 4 | 4 | 2 | 4 | 6 | 7 | 3 | 2 | 2 | 2 | 0 |
| Bedstraw | 0 | 2 | 6 | 2 | 4 | 0 | 1 | 0 | 3 | 2 | 2 | 1 | 0 | 3 | 9 | 1 | 0 | 1 | 1 | 4 | 6 | — | — | 8 | 3 | 4 | 4 | 2 | — |
| Blackgrass | 0 | 6 | 4 | 1 | 4 | 0 | 3 | 0 | 5 | 2 | 2 | 1 | 0 | 3 | 10 | 3 | 0 | 0 | 1 | 3 | 7 | 4 | 3 | 9 | 9 | 2 | 8 | 2 | 1 |
| Chickweed | 0 | 7 | 8 | — | — | 0 | 3 | 0 | 4 | 1 | 1 | 1 | 0 | 7 | 8 | 7 | 1 | 4 | 5 | 4 | — | — | — | 9 | 9 | — | — | 4 | 7 |
| Cocklebur | 0 | 0 | 0 | 0 | 0 | 0 | 0 | 0 | 1 | 0 | 0 | 0 | 0 | 0 | — | 0 | 0 | 0 | 3 | 2 | 1 | 0 | 0 | 0 | — | 0 | 0 | 0 | 0 |
| Corn | 0 | 0 | 3 | 0 | 0 | 0 | 0 | 0 | 0 | 0 | 0 | 0 | 0 | 1 | 1 | 0 | 0 | 0 | 0 | 1 | 1 | 0 | 2 | 2 | 0 | 0 | 1 | 0 | 0 |
| Cotton | 0 | 3 | 0 | — | 0 | 0 | 0 | 0 | 0 | 0 | 3 | 1 | 0 | 0 | 5 | 0 | 0 | 0 | 0 | 3 | 0 | 3 | 4 | 0 | 0 | 0 | 3 | 2 | 0 |
| Crabgrass | 0 | 9 | 9 | 4 | 10 | 4 | 9 | 0 | 9 | 5 | 4 | 8 | 1 | 9 | 10 | 8 | 2 | 4 | 8 | 9 | 9 | 10 | 9 | 10 | 9 | 8 | 10 | 4 | 2 |
| Downy brome | 0 | 3 | 1 | 0 | 5 | 0 | 0 | 0 | 2 | 2 | 1 | 2 | 0 | 1 | 10 | 3 | 1 | 0 | 2 | 3 | 7 | 9 | 4 | 9 | 10 | — | 7 | 5 | 0 |
| Giant foxtail | 0 | 9 | 10 | 3 | 10 | 3 | 8 | 0 | 9 | 4 | 3 | 9 | 0 | 10 | 10 | 7 | 2 | 4 | 8 | 9 | 8 | 10 | 9 | 10 | 9 | 9 | 9 | 3 | 2 |
| Lambsquarter | 0 | 6 | 10 | — | — | 0 | 6 | 0 | 3 | 2 | 2 | 6 | 0 | 9 | 9 | 1 | 0 | 0 | 3 | 8 | 6 | — | — | — | 9 | — | — | 9 | 0 |
| Morningglory | 0 | 2 | 4 | 1 | 1 | 0 | 1 | 0 | 2 | 3 | 3 | 1 | 0 | 7 | 7 | 1 | 0 | 2 | 7 | 2 | 2 | 3 | 3 | 3 | 2 | 0 | 1 | 2 | 1 |
| Nutsedge | — | 0 | 0 | 0 | 0 | — | — | 0 | — | 0 | 0 | 0 | 0 | 0 | 0 | 0 | 0 | 0 | 3 | 0 | 1 | 0 | 0 | — | 0 | 0 | 0 | 0 | 0 |
| Rape | 0 | 2 | 8 | 7 | — | 0 | 1 | 0 | 3 | 2 | 2 | 2 | 0 | 3 | 7 | 2 | 0 | 1 | 3 | 2 | 3 | 4 | 5 | 6 | 3 | — | — | 2 | 0 |
| Rice | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 1 | 0 | 0 | 0 | 0 | 0 |
| Sorghum | 0 | 1 | 1 | 0 | 0 | 0 | 0 | 0 | 0 | 0 | 0 | 0 | 0 | 2 | 4 | 0 | 0 | 0 | 1 | 0 | 2 | 1 | 2 | 4 | 1 | 0 | 1 | 1 | 0 |
| Soybean | 0 | 0 | 1 | 0 | 0 | 0 | 0 | 0 | 0 | 1 | 0 | 0 | 0 | 0 | 1 | 0 | 0 | 0 | 0 | 1 | 0 | 1 | 1 | 1 | 0 | 0 | 0 | 0 | 0 |
| Sugar beet | 0 | 8 | 9 | — | 4 | 0 | 3 | 0 | 9 | 3 | 6 | 5 | 0 | 9 | 10 | 1 | 0 | 1 | 2 | 8 | 10 | 10 | 10 | 7 | 8 | 4 | 9 | 3 | 0 |
| Velvetleaf | 0 | 2 | 2 | 0 | 1 | 0 | 2 | 0 | 5 | 1 | 1 | 1 | 0 | 3 | 8 | 2 | 0 | 2 | 3 | 7 | 0 | 1 | 2 | 4 | 1 | 0 | 1 | 1 | 1 |
| Wheat | 0 | 0 | 0 | 0 | 0 | 0 | 1 | 0 | 0 | 1 | 0 | 0 | 0 | 1 | 2 | 0 | 0 | 0 | 0 | 0 | 0 | 1 | 2 | 2 | 2 | 0 | 1 | 0 | 0 |
| Wild buckwheat | 0 | 2 | 5 | — | — | 0 | 0 | 0 | 3 | 1 | 0 | 0 | 0 | 12 | 0 | 0 | 0 | 1 | 1 | — | — | 2 | 7 | — | — | 2 | — | 0 | |
| Wild oat | 0 | 5 | 3 | 2 | 4 | 0 | 3 | 0 | 4 | 4 | 2 | 4 | 0 | 4 | 9 | 3 | 1 | 2 | 4 | 7 | 8 | 8 | 8 | 9 | 8 | 4 | 8 | 7 | 0 |

TABLE A-continued

| Rate 200 g/ha | 55 | 56 | 57 | 58 | 60 | 61 | 62 | 63 | 64 | 65 | 66 | 67 | 68 | 69 | 70 | 71 | 72 | 74 | 75 | 76 | 77 | 78 | 79 | 81 | 82 | 83 | 84 | 85 | 86 |
|---|---|---|---|---|---|---|---|---|---|---|---|---|---|---|---|---|---|---|---|---|---|---|---|---|---|---|---|---|---|
| | COMPOUND | | | | | | | | | | | | | | | | | | | | | | | | | | | | |
| PREEMERGENCE | | | | | | | | | | | | | | | | | | | | | | | | | | | | | |
| Barley | 0 | 1 | 0 | 0 | 0 | 3 | 3 | 0 | 2 | 4 | 0 | 1 | 0 | 2 | 1 | 5 | 4 | 0 | 0 | 0 | 0 | 1 | 0 | 0 | 0 | 0 | 0 | 0 | 0 |
| Barnyardgrass | 5 | 2 | 0 | 2 | 0 | 3 | 2 | 0 | 3 | 5 | 3 | 4 | 0 | 2 | 3 | 8 | 7 | 0 | 0 | 0 | 0 | 1 | 2 | 0 | 7 | 0 | 0 | 0 | 1 |
| Bedstraw | 1 | 10 | 0 | 10 | 1 | 1 | 1 | 0 | 2 | 2 | 3 | 8 | 0 | 7 | 2 | 4 | — | 0 | — | — | 0 | 3 | 0 | 0 | 6 | 0 | 0 | 0 | 0 |
| Blackgrass | 7 | 6 | 0 | 2 | 0 | 6 | 5 | 0 | 6 | 7 | 1 | 5 | 0 | 5 | 4 | 9 | 4 | 0 | 0 | 0 | 3 | 4 | 1 | 1 | 5 | 1 | 0 | 0 | 0 |
| Chickweed | 7 | 6 | 2 | 3 | 0 | 2 | 3 | 0 | 1 | 3 | 1 | 7 | 0 | 9 | 3 | 8 | 8 | 0 | 0 | 0 | 0 | 7 | 0 | 0 | 2 | 1 | 0 | 0 | 0 |
| Cocklebur | — | 1 | 0 | 0 | — | 0 | 0 | 0 | 0 | 9 | 0 | 0 | 0 | 1 | 0 | 1 | 0 | 0 | 0 | 0 | 0 | 0 | 0 | 0 | 0 | 0 | 0 | 0 | 0 |
| Corn | 1 | 1 | 0 | 1 | 0 | 1 | 1 | 0 | 0 | 1 | 0 | 0 | 0 | 0 | 0 | 1 | 0 | 0 | 0 | 0 | 0 | 0 | 0 | 0 | 0 | 0 | 0 | 0 | 0 |
| Cotton | 3 | 0 | 0 | 1 | 0 | 1 | 0 | 0 | 0 | 0 | 0 | 1 | 0 | 2 | 0 | 2 | 1 | 0 | 0 | 0 | 0 | 0 | 0 | 0 | 1 | 0 | 0 | 0 | 0 |
| Crabgrass | 10 | 9 | 1 | 9 | 3 | 10 | 9 | 0 | 9 | 9 | 4 | 9 | 0 | 7 | 10 | 10 | 9 | 0 | 0 | 0 | 3 | 2 | 5 | 3 | 8 | 3 | 1 | 0 | 6 |
| Downy brome | 4 | 2 | 0 | 1 | 0 | 4 | 3 | 0 | 3 | 7 | 0 | 4 | 0 | 7 | 3 | 10 | 7 | 0 | 0 | 0 | 0 | 4 | 1 | 0 | 2 | 0 | 0 | 0 | 0 |
| Giant foxtail | 9 | 9 | 2 | 8 | 1 | 8 | 8 | 0 | 9 | 9 | 4 | 6 | 0 | 6 | 8 | 9 | 9 | 0 | 0 | 0 | 3 | 3 | 4 | 1 | 7 | 1 | 2 | 0 | 4 |
| Lambsquarter | 2 | 10 | 1 | 9 | 0 | 10 | 6 | 0 | 8 | 10 | 9 | 10 | 0 | 8 | 7 | 8 | 9 | 0 | 0 | 0 | 2 | 3 | 6 | 2 | 10 | 0 | 1 | 0 | 0 |
| Morningglory | 2 | 2 | 1 | 2 | 2 | 2 | 1 | 0 | 1 | 4 | 2 | 4 | 0 | 4 | — | 2 | 2 | 0 | 0 | 0 | 0 | 1 | 0 | 1 | 1 | 1 | 0 | 0 | — |
| Nutsedge | 0 | — | 0 | 0 | 6 | — | — | 0 | — | 0 | 0 | 0 | — | 0 | 0 | — | — | — | — | — | — | — | — | — | 0 | 0 | 0 | 0 | 0 |
| Rape | 2 | 4 | 0 | 2 | 1 | 4 | 3 | 0 | 2 | 3 | 4 | 3 | 0 | 3 | 2 | 3 | 3 | 0 | 0 | 0 | 0 | 2 | 1 | 0 | 6 | 0 | 0 | 0 | 0 |
| Rice | 0 | 1 | 0 | 0 | 0 | 2 | 0 | 0 | 1 | 2 | 1 | 0 | 0 | 0 | 0 | 1 | 1 | 0 | 0 | 0 | 0 | 0 | 0 | 0 | 0 | 0 | 0 | 0 | 0 |
| Sorghum | 1 | 0 | 0 | 0 | 0 | 0 | 0 | 0 | 0 | 0 | 0 | 3 | 0 | 1 | 0 | 4 | 1 | 0 | 0 | 0 | 0 | 0 | 0 | 0 | 1 | 0 | 0 | 0 | 0 |
| Soybean | 0 | 1 | 0 | 0 | 0 | 0 | 0 | 0 | 0 | 0 | 0 | 0 | 0 | 0 | 0 | 1 | 0 | 0 | 0 | 0 | 0 | 0 | 0 | 0 | 0 | 0 | 0 | 0 | 0 |
| Sugar beet | 5 | 8 | 0 | 7 | 0 | 8 | 5 | 0 | 8 | 9 | 6 | 8 | 0 | 9 | 8 | 8 | 6 | 0 | 0 | 0 | 1 | 2 | 1 | 3 | 9 | 0 | 2 | 0 | 0 |
| Velvetleaf | 1 | 2 | 0 | 2 | 0 | 2 | 3 | 0 | 3 | 3 | 2 | 3 | 0 | 2 | 1 | 5 | 2 | 0 | 0 | 0 | 2 | 4 | 3 | 0 | 2 | 0 | 0 | 0 | 0 |
| Wheat | 0 | 1 | 0 | 0 | 0 | 2 | 2 | 0 | 2 | 3 | 0 | 2 | 0 | 2 | 2 | 5 | 2 | 0 | 0 | 0 | 0 | 1 | 0 | 0 | 1 | 0 | 0 | 0 | 0 |
| Wild buckwheat | 1 | 1 | 0 | 2 | 0 | 1 | 1 | 0 | 1 | 2 | 2 | 2 | 0 | 1 | 0 | 2 | 2 | 0 | 0 | 0 | 0 | 0 | 0 | 0 | 4 | 0 | 0 | 0 | 0 |
| Wild oat | 9 | 7 | 0 | 4 | 4 | 10 | 8 | 0 | 7 | 9 | 3 | 7 | 0 | 7 | 8 | 9 | 8 | 0 | 0 | 0 | 6 | 4 | 4 | 0 | 5 | 2 | 0 | 0 | 0 |

| Rate 200 g/ha | 87 | 88 | 89 | 90 | 91 | 92 | 93 | 94 | 95 | 96 | 97 | 98 | 99 | 100 | 101 | 102 | 103 | 104 | 105 |
|---|---|---|---|---|---|---|---|---|---|---|---|---|---|---|---|---|---|---|---|
| PREEMERGENCE | | | | | | | | | | | | | | | | | | | |
| Barley | 0 | 0 | 2 | 3 | 1 | 0 | 1 | 0 | 1 | 0 | 3 | 0 | 1 | 5 | 4 | 3 | 0 | 0 | 0 |
| Barnyardgrass | 0 | 0 | 8 | 9 | 9 | 0 | 7 | 3 | 2 | 0 | 9 | 4 | 3 | 6 | 3 | 1 | 0 | 0 | 0 |
| Bedstraw | 0 | 1 | 3 | 10 | 1 | 0 | 4 | 0 | 1 | 0 | 6 | 5 | 2 | 8 | 6 | 4 | 3 | 3 | 1 |
| Blackgrass | 0 | 0 | 9 | 9 | 9 | 3 | 6 | 5 | 6 | 0 | 10 | 6 | 8 | 9 | 4 | 1 | 0 | 0 | 0 |
| Chickweed | 0 | 2 | 9 | 9 | 7 | 5 | 5 | 3 | 2 | 1 | 8 | 6 | 5 | 9 | 9 | 9 | 6 | 6 | 0 |
| Cocklebur | 0 | 0 | 1 | 1 | — | 0 | 4 | 1 | 1 | 0 | 0 | 0 | 1 | 1 | 0 | 0 | 0 | 0 | 0 |
| Corn | 0 | 0 | 0 | 0 | 0 | 0 | 0 | 0 | 0 | 0 | 0 | 0 | 0 | 0 | 1 | 0 | 0 | 0 | 0 |
| Cotton | 0 | 0 | 2 | 4 | 3 | 0 | 3 | 0 | 0 | 0 | 2 | 2 | 3 | 5 | 0 | 1 | 0 | 0 | 0 |
| Crabgrass | 0 | 3 | 10 | 10 | 9 | 4 | 9 | 8 | 6 | 1 | 9 | 9 | 9 | 10 | 10 | 9 | 1 | 1 | 0 |
| Downy brome | 0 | 0 | 7 | 8 | 3 | 0 | 3 | 2 | 2 | 0 | 9 | 7 | 3 | 6 | 7 | 5 | 1 | 0 | 0 |
| Giant foxtail | 0 | 6 | 10 | 9 | 9 | 4 | 9 | 9 | 8 | 1 | 9 | 8 | 8 | 9 | 9 | 9 | 2 | 2 | 0 |
| Lambsquarter | 0 | 1 | 9 | 9 | 4 | 2 | 4 | 2 | 1 | 0 | 9 | 7 | 4 | 9 | 9 | 8 | 3 | 2 | 1 |
| Morningglory | 0 | 0 | 5 | 3 | 3 | 1 | 2 | 3 | 4 | 1 | 2 | 4 | 3 | 10 | 3 | 4 | 2 | 1 | 0 |
| Nutsedge | 0 | 0 | 0 | 0 | 0 | 0 | 0 | 0 | 0 | 0 | 0 | — | — | 0 | 0 | 0 | — | 0 | 0 |
| Rape | 0 | 0 | 8 | 3 | 2 | 2 | 6 | 2 | 2 | 0 | 4 | 0 | 1 | 8 | 7 | 7 | 2 | 1 | 0 |
| Rice | 0 | 0 | 2 | 1 | 1 | 0 | 0 | 1 | 0 | 0 | 0 | 0 | 0 | 1 | 1 | 0 | 0 | 0 | 0 |
| Sorghum | 0 | 0 | 6 | 8 | 6 | 0 | 1 | 0 | 0 | 0 | 2 | 2 | 0 | 4 | 2 | 2 | 0 | 0 | 0 |
| Soybean | 0 | 0 | 2 | 1 | 0 | 0 | 0 | 0 | 0 | 0 | 0 | 0 | 0 | 2 | 1 | 0 | 0 | 0 | 0 |

TABLE A-continued

| | COMPOUND | | | | | | | | | | | | | | | | | | |
|---|---|---|---|---|---|---|---|---|---|---|---|---|---|---|---|---|---|---|---|
| Sugar beet | 0 | 0 | 8 | 9 | 3 | 1 | 5 | 5 | 1 | 0 | 4 | 7 | 1 | 9 | 9 | 8 | 3 | 6 | 0 |
| Velvetleaf | 0 | 0 | 7 | 6 | 3 | 1 | 2 | 1 | 2 | 0 | 2 | 3 | 2 | 8 | 2 | 7 | 2 | 0 | 0 |
| Wheat | 0 | 0 | 3 | 3 | 1 | 0 | 1 | 0 | 0 | 0 | 3 | 0 | 0 | 6 | 4 | 2 | 0 | 0 | 0 |
| Wild buckwheat | 0 | 1 | 3 | 4 | 2 | 1 | 2 | 1 | 1 | 0 | 5 | 1 | 0 | 5 | 3 | 1 | 0 | 0 | 0 |
| Wild oat | 0 | 2 | 9 | 9 | 7 | 1 | 4 | 5 | 3 | 0 | 9 | 5 | 6 | 9 | 9 | 7 | 2 | 0 | 0 |

| Rate 100 g/ha | 52 | 59 | 73 | Rate 100 g/ha | 52 | 59 | 73 | Rate 50 g/ha | 66 | Rate 50 g/ha | 66 |
|---|---|---|---|---|---|---|---|---|---|---|---|
| POSTEMERGENCE | | | | PREEMERGENCE | | | | POSTEMERGENCE | | PREEMERGENCE | |
| Barley | 3 | 2 | 3 | Barley | 0 | 0 | 1 | Barley | 1 | Barley | 0 |
| Barnyardgrass | 3 | 2 | 3 | Barnyardgrass | 2 | 2 | 4 | Barnyardgrass | 1 | Barnyardgrass | 0 |
| Bedstraw | 7 | 8 | 7 | Bedstraw | 0 | 2 | 0 | Bedstraw | — | Bedstraw | 0 |
| Blackgrass | 2 | 2 | 2 | Blackgrass | 1 | 3 | 5 | Blackgrass | — | Blackgrass | 1 |
| Chickweed | 6 | 8 | 4 | Chickweed | 5 | 4 | 4 | Chickweed | 3 | Chickweed | 0 |
| Cocklebur | 5 | 5 | 3 | Cocklebur | 0 | 0 | 2 | Cocklebur | 2 | Cocklebur | 0 |
| Corn | 2 | 2 | 2 | Corn | 0 | 0 | 0 | Corn | 2 | Corn | 0 |
| Cotton | 8 | 6 | 9 | Cotton | 0 | 2 | 1 | Cotton | 2 | Cotton | 0 |
| Crabgrass | 2 | 2 | 3 | Crabgrass | 8 | 7 | 8 | Crabgrass | 2 | Crabgrass | 1 |
| Downy brome | 1 | 2 | 2 | Downy brome | 2 | 1 | 4 | Downy brome | 0 | Downy brome | 0 |
| Giant foxtail | 2 | 2 | 2 | Giant foxtail | 4 | 8 | 5 | Giant foxtail | 2 | Giant foxtail | 2 |
| Lambsquarter | 8 | 8 | 7 | Lambsquarter | 0 | 7 | 3 | Lambsquarter | 3 | Lambsquarter | 2 |
| Morningglory | 1 | 3 | 3 | Morningglory | 2 | 2 | 5 | Morningglory | 2 | Morningglory | 1 |
| Nutsedge | 1 | 0 | — | Nutsedge | 0 | 0 | — | Nutsedge | — | Nutsedge | 0 |
| Rape | 6 | 5 | 7 | Rape | 0 | 2 | 2 | Rape | 3 | Rape | 0 |
| Rice | 2 | 3 | 3 | Rice | 0 | 0 | 0 | Rice | 2 | Rice | 0 |
| Sorghum | — | 2 | 3 | Sorghum | 0 | 0 | 0 | Sorghum | 1 | Sorghum | 0 |
| Soybean | 4 | 5 | 1 | Soybean | 0 | 0 | 0 | Soybean | 2 | Soybean | 0 |
| Sugar beet | 7 | 7 | 7 | Sugar beet | 1 | 3 | 1 | Sugar beet | 3 | Sugar beet | 0 |
| Velvetleaf | 3 | 8 | 4 | Velvetleaf | 2 | 5 | 3 | Velvetleaf | 1 | Velvetleaf | 0 |
| Wheat | 2 | 2 | 2 | Wheat | 0 | 0 | 0 | Wheat | 2 | Wheat | 0 |
| Wild buckwheat | 4 | 5 | 3 | Wild buckwheat | 0 | 0 | 1 | Wild buckwheat | 3 | Wild buckwheat | 0 |
| Wild oat | 3 | 4 | 2 | Wild oat | 4 | 5 | 6 | Wild oat | 3 | Wild oat | 2 |

TEST B

The compounds evaluated in this test were formulated in a non-phytoxic solvent mixture which includes a surfactant and applied to the soil surface before plant seedlings emerged (preemergence application), to water that covered the soil surface (flood application), and to plants that were in the one-to-four leaf stage (postemergence application). A sandy loam soil was used for the preemergence and postemergence tests, while a silt loam soil was used in the flood test. Water depth was approximately 2.5 cm for the flood test and was maintained at this level for the duration of the test.

Plant species in the preemergence and postemergence tests consisted of barnyardgrass (*Echinochloa crus-galli*), barley (*Hordeum vulgate*), bedstraw (*Galium aparine*), blackgrass (*Alopecurus myosuroides*), chickweed (*Stellaria media*), cocklebur (*Xanthium strumarium*), corn (*Zea mays*), cotton (*Gossypium hitsuture*), crabgrass (*Digitaria sanguinalis*), downy brome (*Bromus tectorum*), giant foxtail (*Setaria faberii*), johnsongrass (*Sorghum halpense*), lambsquarters (*Chenopodium album*), morningglory (*Ipomoea hederacea*), pigweed (*Amaranthus retroflexus*), rape (*Brassica napus*), ryegrass (*Lolium multiflorum*), soybean (*Glycine max*), speedwell (*Veronica persica*), sugar beet (*Beta vulgaris*), velvetleaf (*Abutilon theophrasti*), wheat (*Triticum aestivum*), wild buckwheat (*Polygonum convolvulus*), and wild oat (*Avena fatua*). All plant species were planted one day before application of the compound for the proemergence portion of this test. Plantings of these species were adjusted to produce plants of appropriate size for the postemergence portion of the test. Plant species in the flood test consisted of rice (*Oryza sativa*), umbrella sedge (*Cyperus difformis*), duck salad (*Heteranthera limosa*), barnyardgrass (*Echinochloa crus-galli*) and Late watergrass (*Echinocloa oryzicola*) grown to the 2 leaf stage for testing.

All plant species were grown using normal greenhouse practices. Visual evaluations of injury expressed on treated plants, when compared to untreated controls, were recorded approximately fourteen to twenty one days after application of the test compound. Plant response this ratings, summarized in Table B, were recorded on a 0 to 100 scale where 0 is no effect and 100 is complete control. A dash (–) response means no test result.

TABLE B

COMPOUND

| Rate 2000 g/ha | 52 | Rate 1000 g/ha | 47 | 48 | 52 |
|---|---|---|---|---|---|
| POSTEMERGENCE | | POSTEMERGENCE | | | |
| Barley Igri | — | Barley Igri | — | — | — |
| Barnyard 2 | 40 | Barnyard 2 | 75 | 70 | 35 |
| Barnyardgrass | — | Barnyardgrass | — | — | — |
| Bedstraw | — | Bedstraw | — | — | — |
| Blackgrass | — | Blackgrass | — | — | — |
| Chickweed | — | Chickweed | — | — | — |
| Cocklebur | — | Cocklebur | — | — | — |
| Corn | — | Corn | — | — | — |
| Cotton | — | Cotton | — | — | — |
| Crabgrass | — | Crabgrass | — | — | — |
| Downy Brome | — | Downy Brome | — | — | — |
| Duck salad | 65 | Duck salad | 35 | 65 | 25 |
| Giant foxtail | — | Giant foxtail | — | — | — |
| Italn. Rygrass | — | Italn. Rygrass | — | — | — |
| Johnsongrass | — | Johnsongrass | — | — | — |
| Lambsquarter | — | Lambsquarter | — | — | — |
| Morningglory | — | Morningglory | — | — | — |
| Rape | — | Rape | — | — | — |
| Redroot Pigweed | — | Redroot Pigweed | — | — | — |
| Rice Japonica | 40 | Rice Japonica | 25 | 15 | 35 |
| Soybean | — | Soybean | — | — | — |
| Speedwell | — | Speedwell | — | — | — |
| Sugar beet | — | Sugar beet | — | — | — |
| Umbrella sedge | 85 | Umbrella sedge | 80 | 80 | 85 |
| Velvetleaf | — | Velvetleaf | — | — | — |
| Watergrass 2 | — | Watergrass 2 | — | — | — |
| Wheat | — | Wheat | — | — | — |
| Wild buckwheat | — | Wild buckwheat | — | — | — |
| Wild oat | — | Wild oat | — | — | — |

| Rate 500 g/ha | 19 | 20 | 24 | 47 | 48 | 52 | 56 | 61 |
|---|---|---|---|---|---|---|---|---|
| POSTEMERGENCE | | | | | | | | |
| Barley Igri | 50 | — | 35 | — | — | — | 35 | 30 |
| Barnyard 2 | 95 | 85 | 80 | 65 | 15 | 15 | 30 | 40 |
| Barnyardgrass | 90 | — | 90 | — | — | — | 30 | 40 |
| Bedstraw | 90 | — | 95 | — | — | — | — | 90 |
| Blackgrass | 50 | — | 85 | — | — | — | 60 | 35 |
| Chickweed | 90 | — | 95 | — | — | — | — | 95 |
| Cocklebur | 90 | — | 85 | — | — | — | 75 | 35 |
| Corn | 50 | — | 35 | — | — | — | 20 | 25 |
| Cotton | 80 | — | 100 | — | — | — | 60 | 40 |
| Crabgrass | 90 | — | 80 | — | — | — | 35 | 20 |
| Downy Brome | 40 | — | 60 | — | — | — | 30 | 45 |

TABLE B-continued

| | COMPOUND | | | | | | | |
|---|---|---|---|---|---|---|---|---|
| Duck salad | 40 | 40 | 30 | 40 | 5 | 20 | 60 | 0 |
| Giant foxtail | 90 | — | 70 | — | — | — | 35 | 25 |
| Italn. Rygrass | 90 | — | 90 | — | — | — | 35 | 50 |
| Johnsongrass | 90 | — | — | — | — | — | 30 | 55 |
| Lambsquarter | 90 | — | 100 | — | — | — | 75 | 95 |
| Morningglory | 90 | — | 90 | — | — | — | 40 | 90 |
| Rape | 95 | — | 100 | — | — | — | 45 | 60 |
| Redroot Pigweed | 90 | — | 90 | — | — | — | 70 | 60 |
| Rice Japonica | 85 | — | 70 | 35 | 10 | 5 | 20 | 20 |
| Soybean | 85 | — | 80 | — | — | — | 50 | 35 |
| Speedwell | 100 | — | 100 | — | — | — | 100 | 100 |
| Sugar beet | 95 | — | 100 | — | — | — | — | 95 |
| Umbrella sedge | 90 | — | 40 | 85 | 80 | 65 | 60 | 60 |
| Velvetleaf | 90 | — | 75 | — | — | — | 60 | 55 |
| Watergrass 2 | 100 | 90 | 85 | — | — | — | — | — |
| Wheat | 20 | — | 35 | — | — | — | 25 | 25 |
| Wild buckwheat | 95 | — | 95 | — | — | — | 70 | 85 |
| Wild oat | 70 | — | 90 | — | — | — | 50 | 60 |

| Rate 500 g/ha | 19 | 24 | 56 | 61 |
|---|---|---|---|---|
| PREEMERGENCE | | | | |
| Barley Igri | 0 | 30 | 0 | 0 |
| Barnyardgrass | 95 | 100 | 75 | 85 |
| Bedstraw | 100 | 90 | 60 | 95 |
| Blackgrass | 100 | 100 | 80 | 100 |
| Chickweed | 100 | 90 | 80 | 100 |
| Cocklebur | 20 | 25 | 0 | 25 |
| Corn | 25 | 30 | 10 | 9 |
| Cotton | 30 | 60 | 0 | 25 |
| Crabgrass | 100 | 100 | 100 | 100 |
| Downy Brome | 50 | 80 | 70 | 20 |
| Giant foxtail | 100 | 100 | 100 | 100 |
| Italn. Rygrass | 100 | 100 | 70 | 95 |
| Johnsongrass | 90 | 95 | 90 | 70 |
| Lambsquarter | 100 | 90 | 80 | 100 |
| Morningglory | 90 | 90 | 30 | 70 |
| Rape | 95 | 90 | 70 | 65 |
| Redroot Pigweed | 100 | — | 100 | 100 |
| Soybean | 30 | 50 | 0 | 20 |
| Speedwell | 100 | 95 | 100 | 100 |
| Sugar beet | 100 | 95 | — | 100 |
| Velvetleaf | 65 | 70 | 40 | 70 |
| Wheat | 20 | 20 | 10 | 20 |
| Wild buckwheat | 90 | 75 | 40 | 85 |
| Wild oat | 90 | 80 | 70 | 95 |

| Rate 250 g/ha | 19 | 20 | 24 | 26 | 35 | 36 | 47 | 48 | 52 | 53 | 56 | 61 | 71 | 90 | 91 |
|---|---|---|---|---|---|---|---|---|---|---|---|---|---|---|---|
| POSTEMERGENCE | | | | | | | | | | | | | | | |
| Barley Igri | 40 | 45 | 30 | 30 | 0 | 20 | 40 | — | — | 20 | 35 | 30 | 40 | 40 | 20 |
| Barnyard 2 | 95 | 75 | 80 | 85 | 60 | 30 | 75 | 20 | 5 | 30 | 20 | 40 | 60 | 65 | 35 |
| Barnyardgrass | 80 | 70 | 60 | 40 | 30 | 40 | 85 | — | — | 25 | 25 | 40 | 80 | 60 | 35 |
| Bedstraw | 90 | 75 | 95 | 90 | 90 | 90 | 90 | — | — | 85 | 80 | 90 | 90 | 80 | 70 |
| Blackgrass | 40 | 45 | 70 | 30 | 20 | 35 | 70 | — | — | 0 | 40 | — | 50 | 50 | 40 |
| Chickweed | 90 | 50 | 90 | 50 | — | — | — | — | — | — | — | — | 90 | 90 | 65 |
| Cocklebur | 90 | 85 | 80 | 80 | 55 | 80 | 70 | — | — | 70 | 70 | 35 | 80 | 80 | 80 |
| Corn | 40 | 40 | 35 | 30 | 15 | 25 | 35 | — | — | 15 | 15 | 20 | 35 | 30 | 30 |
| Cotton | 70 | 95 | 100 | 90 | 60 | 60 | 80 | — | — | 70 | 40 | 40 | 90 | 90 | 80 |
| Crabgrass | 80 | 45 | 60 | 50 | 20 | 20 | 35 | — | — | 25 | 30 | 20 | 60 | 50 | 40 |
| Downy Brome | 30 | 20 | 45 | 10 | 0 | 35 | 50 | — | — | 30 | 15 | 20 | 70 | 50 | 35 |
| Duck salad | 30 | 35 | 25 | 10 | 10 | 30 | 85 | 20 | 10 | 20 | 40 | 0 | 60 | 10 | 20 |
| Giant foxtail | 80 | 40 | 70 | 50 | 20 | 25 | 30 | — | — | 30 | 30 | 15 | 35 | 70 | 50 |
| Italn Rygrass | 80 | 80 | 85 | 50 | 0 | 30 | 50 | — | — | 20 | 25 | 40 | 70 | 60 | 40 |
| Johnsongrass | 70 | 70 | — | 80 | 40 | 35 | 40 | — | — | 25 | 20 | 55 | 60 | 60 | 40 |
| Lambsquarter | 90 | 95 | 100 | 90 | 85 | 70 | 90 | — | — | 60 | 60 | 90 | 90 | 90 | 80 |
| Morningglory | 80 | 70 | 90 | 80 | 70 | 80 | 80 | — | — | 50 | 40 | 90 | 90 | 90 | 70 |
| Rape | 90 | 95 | 100 | 90 | 90 | 90 | 80 | — | — | 40 | 35 | 50 | 90 | 100 | 100 |
| Redrt Pigweed | 90 | 70 | 90 | 90 | 90 | 80 | 90 | — | — | 80 | 70 | 60 | 90 | 90 | 90 |
| Rice Japonica | 70 | 50 | 70 | 55 | 20 | 20 | 0 | 15 | 0 | 20 | 10 | 20 | 40 | 30 | 20 |
| Soybean | 85 | 80 | 70 | 50 | 60 | 60 | 70 | — | — | 70 | 40 | 35 | 70 | 70 | 60 |
| Speedwell | 100 | 100 | 100 | 95 | 90 | 100 | 100 | — | — | 90 | 100 | 100 | 100 | 100 | 100 |
| Sugar beet | 90 | 95 | 100 | 90 | — | — | — | — | — | — | — | 95 | 90 | 90 | 70 |
| Umbrella sedge | 90 | 35 | 30 | 40 | 90 | 30 | 85 | 25 | 20 | 40 | 30 | 40 | 60 | 65 | 60 |
| Velvetleaf | 80 | 40 | 75 | 80 | 70 | 70 | 70 | — | — | 70 | 50 | 55 | 65 | 80 | 50 |

TABLE B-continued

COMPOUND

| | | | | | | | | | | | | | | | |
|---|---|---|---|---|---|---|---|---|---|---|---|---|---|---|---|
| Watergrass 2 | 100 | 95 | 85 | 65 | — | — | — | — | — | — | — | — | — | — | — |
| Wheat | 10 | 35 | 30 | 10 | 10 | 35 | 45 | — | — | 0 | 20 | 25 | 40 | 35 | 30 |
| Wild buckwheat | 90 | 85 | 90 | 90 | 60 | 70 | 80 | — | — | 80 | 70 | 80 | 70 | 100 | 60 |
| Wild oat | 60 | 70 | 80 | 35 | 0 | 30 | 60 | — | — | 30 | 30 | 45 | 60 | 60 | 40 |

| Rate 250 g/ha | 19 | 20 | 24 | 26 | 35 | 36 | 47 | 53 | 56 | 61 | 71 | 90 | 91 |
|---|---|---|---|---|---|---|---|---|---|---|---|---|---|
| PREEMERGENCE | | | | | | | | | | | | | |
| Barley Igri | 0 | 0 | 20 | 0 | 20 | 30 | 30 | 20 | 0 | 0 | 15 | 0 | 0 |
| Barnyardgrass | 90 | 85 | 90 | 60 | 95 | 80 | 95 | 40 | 30 | 75 | 95 | 50 | 30 |
| Bedstraw | 30 | 100 | 90 | 40 | 50 | 60 | 100 | 40 | 30 | 90 | 60 | 75 | 30 |
| Blackgrass | 70 | 65 | 80 | 0 | 30 | 90 | 55 | 60 | 60 | 95 | 80 | 70 | 60 |
| Chickweed | 95 | 65 | 75 | 40 | 80 | 80 | 85 | 70 | 80 | 95 | 70 | 100 | 80 |
| Cocklebur | — | 20 | 15 | 20 | 50 | 70 | 20 | 40 | 0 | — | 20 | 20 | 0 |
| Corn | 10 | 0 | 20 | 0 | 0 | 10 | 50 | 0 | 0 | 0 | 30 | 10 | 0 |
| Cotton | 30 | 25 | 40 | 30 | 0 | 0 | 50 | 0 | 0 | 0 | 20 | 40 | 20 |
| Crabgrass | 100 | 100 | 100 | 100 | 100 | 100 | 100 | 100 | 90 | 100 | 100 | 100 | 85 |
| Downy Brome | 20 | 35 | 30 | 0 | 0 | 40 | 30 | 10 | 30 | 20 | 10 | 30 | 30 |
| Giant foxtail | 95 | 100 | 100 | 100 | 100 | 100 | 100 | 80 | 90 | 95 | 100 | 100 | 95 |
| Italn. Rygrass | 90 | 85 | 90 | 65 | 20 | 30 | 60 | 30 | 70 | 80 | 75 | 40 | 30 |
| Johnsongrass | 85 | 90 | 95 | 40 | 70 | 70 | 90 | 40 | 70 | 70 | 40 | 70 | 50 |
| Lambsquarter | 100 | 100 | 90 | 95 | 95 | 100 | 95 | 60 | 80 | 95 | 60 | 100 | 40 |
| Morningglory | 75 | 75 | 70 | 70 | 30 | 30 | 50 | 60 | 20 | 60 | 85 | 70 | 40 |
| Rape | 70 | 80 | 65 | 0 | 50 | 70 | 60 | 50 | 60 | 30 | 30 | 40 | 30 |
| Redroot Pigweed | 100 | 100 | — | 90 | 100 | 100 | 90 | 90 | 90 | 100 | 100 | 100 | 80 |
| Soybean | 20 | 0 | 30 | 0 | 20 | 10 | 0 | 20 | 0 | 10 | 0 | 10 | 20 |
| Speedwell | 95 | 100 | 95 | 95 | 90 | 100 | 100 | 70 | 90 | 100 | 70 | 100 | 100 |
| Sugar beet | 95 | 95 | 90 | 65 | — | — | — | — | — | 95 | 60 | 100 | 70 |
| Velvetleaf | 55 | 95 | 70 | 50 | 80 | 60 | 90 | 40 | 30 | 60 | 100 | 70 | 70 |
| Wheat | 0 | 0 | 15 | 0 | 0 | 20 | 30 | 0 | 0 | 20 | 10 | 0 | 0 |
| Wild buckwheat | 80 | 70 | 50 | 45 | 40 | 70 | 30 | 30 | 20 | 65 | 20 | 90 | 20 |
| Wild oat | 85 | 65 | 70 | 35 | 30 | 70 | 60 | 40 | 50 | 80 | 90 | 50 | 40 |

| Rate 125 g/ha | 19 | 20 | 24 | 26 | 35 | 36 | 47 | 48 | 53 | 56 | 61 | 71 | 90 | 91 |
|---|---|---|---|---|---|---|---|---|---|---|---|---|---|---|
| POSTEMERGENCE | | | | | | | | | | | | | | |
| Barley Igri | 30 | 40 | 25 | 20 | 0 | 15 | 40 | — | 20 | 25 | 25 | 35 | 30 | 20 |
| Barnyard 2 | 95 | 70 | 70 | 70 | 40 | 20 | 65 | 15 | 20 | 20 | 20 | 40 | 50 | 25 |
| Barnyardgrass | 50 | 60 | 50 | 30 | 25 | 35 | 50 | — | 20 | 20 | 25 | 50 | 40 | 30 |
| Bedstraw | 90 | — | 90 | 90 | 90 | 80 | 90 | — | — | 65 | 85 | 80 | 80 | — |
| Blackgrass | 30 | 40 | 65 | 25 | 20 | 25 | 40 | — | 0 | 30 | 20 | 40 | 30 | 30 |
| Chickweed | 80 | 50 | 70 | 40 | — | — | — | — | — | — | 90 | 90 | 90 | 65 |
| Cocklebur | 80 | 85 | 80 | 70 | 45 | 60 | 50 | — | 70 | 65 | 30 | 80 | 80 | 80 |
| Corn | 30 | 40 | 25 | 20 | 10 | 15 | 25 | — | 15 | 10 | 20 | 25 | 30 | 25 |
| Cotton | 50 | 90 | 100 | 80 | 50 | 60 | 80 | — | 50 | 30 | 35 | 90 | 90 | 70 |
| Crabgrass | 80 | 35 | 40 | 50 | 15 | 15 | 35 | — | 15 | 30 | 20 | 50 | 40 | 40 |
| Downy Brome | 20 | 10 | 45 | 10 | 0 | 25 | 30 | — | 20 | 10 | 10 | 40 | 40 | 30 |
| Duck salad | 30 | 35 | 15 | 10 | 10 | 10 | 15 | 5 | 10 | 20 | 0 | 50 | 0 | 10 |
| Giant foxtail | 80 | 40 | 50 | 40 | 15 | 20 | 30 | — | 20 | 30 | 15 | 25 | 50 | 40 |
| Italn. Rygrass | 50 | 60 | 60 | 30 | 0 | 20 | 40 | — | 10 | 20 | 25 | 60 | 40 | 35 |
| Johnsongrass | 50 | 40 | — | 70 | 25 | 25 | 40 | — | 15 | 20 | 40 | 50 | 60 | 40 |
| Lambsquarter | 90 | 95 | 90 | 80 | 80 | 70 | 90 | — | 60 | 60 | 90 | 90 | 80 | 80 |
| Morningglory | 80 | 50 | 90 | 70 | 60 | 50 | 70 | — | 40 | 35 | 90 | 80 | 90 | 40 |
| Rape | 90 | 95 | 95 | 80 | 80 | 80 | 70 | — | 40 | 35 | 50 | 80 | 100 | 90 |
| Redroot Pigweed | 90 | 70 | 90 | 90 | 80 | 80 | 90 | — | 70 | 70 | 45 | 80 | 90 | 90 |
| Rice Japonica | 50 | 50 | 65 | 40 | 0 | 15 | 20 | 15 | 10 | 0 | 10 | 40 | 25 | 10 |
| Soybean | 80 | 80 | 70 | 50 | 50 | 50 | 60 | — | 60 | 30 | 30 | 60 | 60 | 55 |
| Speedwell | 100 | 100 | 100 | — | 90 | 100 | 95 | — | 90 | 90 | 95 | 95 | 100 | 100 |
| Sugar beet | 80 | 95 | 100 | 80 | — | — | — | — | — | — | 95 | 80 | 80 | 70 |
| Umbrella sedge | 90 | 35 | 30 | 35 | 75 | 20 | 70 | 55 | 40 | 30 | 30 | 40 | 45 | 50 |
| Velvetleaf | 70 | 35 | 70 | 80 | 70 | 70 | 60 | — | 50 | 40 | 45 | 50 | 80 | 50 |
| Watergrass 2 | 85 | 90 | 70 | 35 | — | — | — | — | — | — | — | — | — | — |
| Wheat | 0 | 35 | 20 | 10 | 0 | 25 | 35 | — | 0 | 15 | 25 | 30 | 30 | 20 |
| Wild buckwheat | 80 | 85 | 90 | 90 | 60 | 70 | 70 | — | 70 | 50 | 60 | 60 | 70 | 60 |
| Wild oat | 50 | 70 | 75 | 35 | 0 | 20 | 40 | — | 20 | 25 | 25 | 40 | 40 | 40 |

| Rate 125 g/ha | 19 | 20 | 24 | 26 | 35 | 36 | 47 | 53 | 56 | 61 | 71 | 90 | 91 |
|---|---|---|---|---|---|---|---|---|---|---|---|---|---|
| PREEMERGENCE | | | | | | | | | | | | | |
| Barley Igri | 0 | 0 | 20 | 0 | 0 | 20 | 20 | 10 | 0 | 0 | 0 | 0 | 0 |
| Barnyardgrass | 50 | 60 | 70 | 30 | 90 | 80 | 95 | 20 | 10 | 35 | 35 | 40 | 10 |
| Bedstraw | 30 | 60 | — | 25 | 10 | 60 | 70 | 30 | 30 | 80 | 10 | 50 | 20 |
| Blackgrass | 35 | 25 | 70 | 0 | 10 | 60 | 35 | 30 | 40 | 80 | 35 | 50 | 40 |
| Chickweed | 30 | 0 | 75 | 0 | 40 | 70 | 35 | 60 | 20 | 70 | 10 | 100 | 70 |

TABLE B-continued

| | COMPOUND | | | | | | | | | | | | |
|---|---|---|---|---|---|---|---|---|---|---|---|---|---|
| Cocklebur | 10 | 0 | 10 | 0 | 10 | 30 | 10 | 40 | 0 | 15 | 0 | 20 | 0 |
| Corn | 0 | 0 | 10 | 0 | 0 | 0 | 10 | 0 | 0 | 0 | 0 | 5 | 0 |
| Cotton | 20 | 10 | 30 | 20 | 0 | 0 | 20 | 0 | 0 | 0 | 0 | 20 | 10 |
| Crabgrass | 100 | 100 | 100 | 100 | 95 | 100 | 100 | 70 | 80 | 95 | 100 | 95 | 85 |
| Downy Brome | 20 | 0 | — | 0 | 0 | 30 | 20 | 0 | 0 | 20 | 0 | 20 | 30 |
| Giant foxtail | 90 | 95 | 100 | 100 | 95 | 100 | 100 | 80 | 80 | 95 | 90 | 100 | 90 |
| Italn. Rygrass | 70 | 30 | 60 | 35 | 15 | 15 | 30 | 15 | 50 | 20 | 30 | 30 | 10 |
| Johnsongrass | 40 | 90 | 80 | 20 | 50 | 60 | 80 | 20 | 30 | 40 | 30 | 60 | 40 |
| Lambsquarter | 100 | 100 | 90 | 90 | 95 | 90 | 90 | 30 | 30 | 85 | 50 | 100 | 30 |
| Morningglory | 65 | 70 | 70 | 30 | 20 | 20 | 40 | 30 | 10 | 30 | 80 | 70 | 40 |
| Rape | 70 | 25 | 60 | 0 | 30 | 50 | 40 | 40 | 50 | 0 | 20 | 30 | 20 |
| Redroot Pigweed | 100 | 90 | — | 90 | 90 | 90 | 80 | 70 | 60 | 95 | 65 | 100 | 60 |
| Soybean | 10 | 0 | 20 | 0 | 10 | 0 | 0 | 10 | 0 | 0 | 0 | 0 | 10 |
| Speedwell | 90 | 95 | 95 | — | 60 | 100 | 100 | 70 | 90 | 95 | — | 100 | 90 |
| Sugar beet | 90 | 80 | 90 | 60 | — | — | — | — | — | 90 | 30 | 100 | 40 |
| Velvetleaf | 45 | 65 | 50 | 0 | 65 | 30 | 90 | 30 | 20 | 30 | 100 | 40 | 20 |
| Wheat | 0 | 0 | 15 | 0 | 0 | 10 | 20 | 0 | 0 | 20 | 0 | 0 | 0 |
| Wild buckwheat | 35 | 0 | 40 | 10 | 20 | 50 | 20 | 30 | 0 | 0 | 20 | 40 | 0 |
| Wild oat | 50 | 25 | 60 | 0 | 10 | 50 | 30 | 30 | 30 | 65 | 30 | 50 | 40 |

| Rate 62 g/ha | 19 | 20 | 24 | 26 | 35 | 36 | 47 | 53 | 56 | 61 | 71 | 90 | 91 |
|---|---|---|---|---|---|---|---|---|---|---|---|---|---|
| POSTEMERGENCE | | | | | | | | | | | | | |
| Barley Igri | 25 | 40 | 25 | 10 | 0 | 15 | 35 | 15 | 25 | 20 | 30 | 30 | 10 |
| Barnyard 2 | 85 | 45 | 70 | 65 | 20 | 20 | 50 | 20 | 20 | 20 | 30 | 30 | 15 |
| Barnyardgrass | 40 | 40 | 30 | 30 | 15 | 25 | 40 | 15 | 15 | 10 | 35 | 40 | 30 |
| Bedstraw | 80 | 70 | 90 | 90 | 90 | 80 | 90 | 85 | 65 | 65 | 80 | 80 | — |
| Blackgrass | 20 | 40 | 45 | 25 | 20 | 25 | 30 | 0 | 20 | 0 | 30 | 20 | 20 |
| Chickweed | 70 | 40 | 70 | 35 | — | — | — | — | — | 80 | 90 | 60 | — |
| Cocklebur | 70 | 80 | 80 | 70 | 35 | 60 | 40 | 60 | 60 | 30 | 60 | 70 | 70 |
| Corn | 20 | 35 | 20 | 20 | 10 | 10 | 15 | 10 | 10 | 20 | 20 | 25 | 20 |
| Cotton | 50 | 80 | 100 | 80 | 50 | 50 | 80 | 50 | 30 | 35 | 80 | 80 | 70 |
| Crabgrass | 40 | 30 | 30 | 40 | 10 | 10 | 25 | 10 | 25 | 10 | 40 | 30 | 30 |
| Downy Brome | 10 | 0 | 25 | 0 | 0 | 20 | 0 | 10 | 0 | 10 | 40 | 30 | 25 |
| Duck salad | 25 | 20 | 10 | 10 | 0 | 10 | 40 | 0 | 20 | 0 | 50 | 0 | 0 |
| Giant foxtail | 40 | 20 | 30 | 35 | 10 | 15 | 25 | 15 | 25 | 10 | 20 | 40 | 40 |
| Italn. Rygrass | 40 | 30 | 30 | 30 | 0 | 10 | 40 | 0 | 15 | 10 | 35 | 40 | 25 |
| Johnsongrass | 40 | 40 | — | 60 | 10 | 20 | 30 | 10 | 15 | 35 | 30 | 50 | 40 |
| Lambsquarter | 90 | 85 | 90 | 70 | 70 | 60 | 80 | 60 | 50 | 75 | 90 | 70 | 80 |
| Morningglory | 60 | 40 | 80 | 70 | 60 | 50 | 60 | 40 | 35 | 70 | 80 | 80 | 40 |
| Rape | 80 | 95 | 95 | 80 | 80 | 60 | 60 | 20 | 35 | 50 | 80 | 100 | 90 |
| Redroot Pigweed | 80 | 50 | 90 | 90 | 80 | 80 | 90 | 65 | 40 | 15 | 80 | 90 | 90 |
| Rice Japonica | 40 | 40 | 40 | 25 | 0 | 10 | 20 | 0 | 0 | 10 | 30 | 20 | 0 |
| Soybean | 80 | 70 | 70 | 50 | 50 | 40 | 50 | 50 | 20 | 30 | 60 | 60 | 55 |
| Speedwell | 100 | 95 | 100 | 95 | — | 80 | 95 | 80 | 80 | 90 | 95 | 100 | 100 |
| Sugar beet | 80 | 90 | 100 | 80 | — | — | — | — | — | 90 | 80 | 80 | — |
| Umbrella sedge | 70 | 20 | 15 | 25 | 40 | 10 | 70 | 20 | 20 | 30 | 20 | 40 | 40 |
| Velvetleaf | 50 | 30 | 70 | 70 | 60 | 60 | 60 | 35 | 35 | 40 | 50 | 70 | 40 |
| Watergrass | 2 | 85 | 90 | 70 | 30 | — | — | — | — | — | — | — | — |
| Wheat | 0 | 30 | 10 | 10 | 0 | 20 | 30 | 0 | 15 | 25 | 25 | 20 | 20 |
| Wild buckwheat | 80 | 75 | 90 | 80 | 40 | 40 | 60 | 40 | 40 | 35 | 50 | 40 | — |
| Wild oat | 45 | 60 | 65 | 30 | 0 | 15 | 40 | 20 | 25 | 26 | 30 | 40 | 30 |

| Rate 62 g/ha | 19 | 20 | 24 | 26 | 35 | 36 | 47 | 53 | 56 | 61 | 71 | 90 | 91 |
|---|---|---|---|---|---|---|---|---|---|---|---|---|---|
| PREEMERGENCE | | | | | | | | | | | | | |
| Barley Igri | 0 | 0 | 10 | 0 | 0 | 0 | 0 | 0 | 0 | 0 | 0 | 0 | 0 |
| Barnyardgrass | 30 | 0 | 40 | 20 | 80 | 50 | 90 | 20 | 0 | 0 | 20 | 30 | 0 |
| Bedstraw | 0 | 30 | 50 | 0 | 0 | 20 | 20 | 20 | 0 | 25 | 0 | 30 | 0 |
| Blackgrass | 10 | 10 | 40 | 0 | 0 | 30 | 30 | 10 | 10 | 80 | 10 | 30 | 30 |
| Chickweed | 10 | 0 | 60 | 0 | 20 | 40 | 20 | 30 | 0 | 10 | 0 | 100 | 20 |
| Cocklebur | — | 0 | 0 | 0 | 10 | 0 | 0 | 20 | 0 | 10 | 0 | 10 | 0 |
| Corn | 0 | 0 | 0 | 0 | 0 | 0 | 0 | 0 | 0 | 0 | 0 | 0 | 0 |
| Cotton | 20 | 10 | 20 | 10 | 0 | 0 | 0 | 0 | 0 | 0 | 0 | 10 | 0 |
| Crabgrass | 100 | 100 | 90 | 80 | 95 | 90 | 80 | 50 | 40 | 70 | 95 | 80 | 75 |
| Downy Brome | 10 | 0 | 30 | 0 | 0 | 20 | 10 | 0 | 0 | 10 | 0 | 15 | 20 |
| Giant foxtail | 60 | 80 | 100 | 100 | 90 | 95 | 100 | 50 | 35 | 90 | 80 | 95 | 80 |
| Italn. Rygrass | 30 | 10 | 35 | 30 | 10 | 10 | 20 | 10 | 20 | 0 | 0 | 20 | 0 |
| Johnsongrass | 30 | 70 | 80 | — | 30 | 50 | 60 | 10 | 30 | 10 | 20 | 10 | 30 |
| Lambsquarter | 90 | 65 | 90 | 90 | 95 | 90 | 75 | 30 | 10 | 65 | 30 | 100 | 30 |
| Morningglory | 30 | 70 | 30 | 10 | 20 | 20 | 30 | 0 | 0 | 20 | 50 | 70 | 20 |
| Rape | 10 | 0 | 50 | 0 | 20 | 30 | 30 | 20 | 30 | 0 | 0 | 30 | 10 |
| Redroot Pigweed | 80 | 30 | — | 70 | 90 | 85 | 70 | 40 | 30 | 90 | 30 | 90 | 40 |
| Soybean | 0 | 0 | 10 | 0 | 0 | 0 | 0 | 0 | 0 | 0 | 0 | 0 | 0 |
| Speedwell | 90 | 60 | 95 | 20 | — | 90 | 90 | 70 | 20 | 60 | 60 | 95 | 90 |

TABLE B-continued

| | COMPOUND | | | | | | | | | | | | |
|---|---|---|---|---|---|---|---|---|---|---|---|---|---|
| Sugar beet | 35 | 40 | 60 | 20 | — | — | — | — | — | 85 | 10 | 90 | 30 |
| Velvetleaf | 30 | 10 | 30 | 0 | 50 | 10 | 80 | 10 | 10 | 20 | 30 | 40 | 0 |
| Wheat | 0 | 0 | 0 | 0 | 0 | 0 | 0 | 0 | 0 | 20 | 0 | 0 | 0 |
| Wild buckwheat | 10 | 0 | 30 | 10 | 10 | 20 | 10 | 10 | 0 | 0 | 0 | 30 | 0 |
| Wild oat | 40 | 0 | 60 | 0 | 0 | 20 | 20 | 20 | 0 | 30 | 30 | 40 | 20 |
| Rate 31 g/ha | 20 | 26 | 35 | 36 | 47 | 53 | 71 | 90 | 91 | | | | |
| POSTEMERGENCE | | | | | | | | | | | | | |
| Barley Igri | 40 | 10 | 0 | 10 | 30 | 10 | 25 | 20 | 10 | | | | |
| Barnyard 2 | 40 | 45 | 10 | 10 | 30 | 10 | 25 | 20 | 10 | | | | |
| Barnyardgrass | 30 | 30 | 10 | 15 | 25 | 15 | 20 | 30 | 25 | | | | |
| Bedstraw | 70 | 70 | 30 | 80 | 90 | 70 | 80 | 70 | 60 | | | | |
| Blackgrass | 40 | 20 | 10 | 20 | — | 0 | 20 | 10 | 10 | | | | |
| Chickweed | 30 | — | — | — | — | — | 70 | 60 | — | | | | |
| Cocklebur | 70 | 70 | 30 | 60 | 40 | 60 | 60 | 70 | 70 | | | | |
| Corn | 30 | 15 | 10 | 10 | 15 | 10 | 15 | 20 | 20 | | | | |
| Cotton | 80 | 70 | 30 | 40 | 60 | 30 | 70 | 70 | 60 | | | | |
| Crabgrass | 25 | — | 10 | 10 | 20 | 10 | 30 | 20 | 30 | | | | |
| Downy Brome | 0 | 0 | 0 | 10 | 0 | 0 | 30 | 10 | 15 | | | | |
| Duck salad | 0 | 0 | 0 | 0 | 20 | 0 | 40 | 0 | 0 | | | | |
| Giant foxtail | 20 | 35 | 10 | 10 | 25 | 15 | 10 | 40 | 40 | | | | |
| Italn. Rygrass | 25 | 20 | 0 | 0 | 30 | 0 | 20 | 20 | 20 | | | | |
| Johnsongrass | 35 | 50 | 0 | 10 | 25 | 10 | 20 | 40 | 25 | | | | |
| Lambsquarter | 85 | 60 | 60 | 60 | 65 | 40 | 70 | 70 | 70 | | | | |
| Morningglory | 40 | — | 50 | 50 | 50 | 35 | 80 | 80 | — | | | | |
| Rape | 90 | 70 | 70 | 40 | 60 | 0 | 75 | 100 | 80 | | | | |
| Redroot Pigweed | 50 | 90 | 80 | 80 | 90 | 65 | 80 | 90 | 80 | | | | |
| Rice Japonica | 40 | 15 | 0 | 10 | 10 | 0 | 30 | 10 | 0 | | | | |
| Soybean | 70 | 40 | 40 | 40 | 40 | 40 | 60 | 50 | 50 | | | | |
| Speedwell | 90 | — | 50 | 80 | 95 | 60 | 95 | 100 | 95 | | | | |
| Sugar beet | 90 | 80 | — | — | — | — | 80 | 70 | 60 | | | | |
| Umbrella sedge | 0 | 0 | 50 | 0 | 40 | 20 | 10 | 40 | 30 | | | | |
| Velvetleaf | 25 | 70 | 50 | 50 | 50 | 35 | 40 | 70 | 40 | | | | |
| Watergrass 2 | 60 | 10 | — | — | — | — | — | — | — | | | | |
| Wheat | 25 | 10 | 0 | 20 | 30 | 0 | 20 | 10 | 15 | | | | |
| Wild buckwheat | 70 | 70 | 20 | 20 | 40 | 40 | 50 | — | 50 | | | | |
| Wild oat | 50 | 25 | 0 | 10 | 40 | 10 | 30 | 35 | 20 | | | | |
| Rate 31 g/ha | 20 | 26 | 35 | 36 | 47 | 53 | 71 | 90 | 91 | | | | |
| PREEMERGENCE | | | | | | | | | | | | | |
| Barley Igri | 0 | 0 | 0 | 0 | 0 | 0 | 0 | 0 | 0 | | | | |
| Barnyardgrass | 0 | 10 | 20 | 20 | 75 | 0 | 10 | 10 | 0 | | | | |
| Bedstraw | 10 | 0 | 0 | 0 | 10 | 0 | 0 | — | 0 | | | | |
| Blackgrass | 0 | 0 | 0 | 10 | 15 | 0 | 015 | 20 | | | | | |
| Chickweed | 0 | 0 | 10 | 20 | — | 0 | 040 | — | | | | | |
| Cocklebur | 0 | 0 | — | 0 | 0 | 0 | 0 | 0 | 0 | | | | |
| Corn | 0 | 0 | 0 | 0 | 0 | 0 | 0 | 0 | 0 | | | | |
| Cotton | 0 | 10 | 0 | 0 | 0 | 0 | 0 | 0 | 0 | | | | |
| Crabgrass | 90 | 50 | 85 | 60 | 50 | 30 | 40 | 60 | 10 | | | | |
| Downy Brome | 0 | 0 | 0 | 10 | 0 | 0 | 0 | 0 | — | | | | |
| Giant foxtail | 80 | 90 | 65 | 95 | 95 | 40 | 30 | 65 | 30 | | | | |
| Italn. Rygrass | 0 | 20 | 0 | 0 | 0 | 0 | 0 | 10 | 0 | | | | |
| Johnsongrass | 0 | — | 0 | 50 | 50 | 0 | 10 | 0 | 10 | | | | |
| Lambsquarter | 65 | 90 | 80 | 50 | 75 | 10 | 0 | 40 | 0 | | | | |
| Morningglory | 30 | 10 | 0 | 10 | 20 | 0 | 50 | 50 | 0 | | | | |
| Rape | 0 | 0 | 10 | 20 | 20 | 20 | 0 | 20 | — | | | | |
| Redroot Pigweed | 10 | 30 | 60 | 85 | 50 | 20 | 0 | 90 | 20 | | | | |
| Soybean | 0 | 0 | 0 | 0 | 0 | 0 | 0 | 0 | 0 | | | | |
| Speedwell | 10 | 20 | — | 90 | 35 | 20 | 60 | 90 | 80 | | | | |
| Sugar beet | 0 | 0 | — | — | — | — | 0 | 70 | 20 | | | | |
| Velvetleaf | 10 | 0 | 10 | 10 | 50 | 0 | 0 | 40 | 0 | | | | |
| Wheat | 0 | 0 | 0 | 0 | 0 | 0 | 0 | 0 | 0 | | | | |
| Wild buckwheat | 0 | 0 | 0 | 0 | 0 | 10 | 0 | 10 | 0 | | | | |
| Wild oat | 0 | 0 | 0 | 10 | 10 | 10 | 20 | 30 | 10 | | | | |

TEST C

Plastic pots were partially filled with silt loam soil. The soil was then saturated with water. Rice (*Oryza salita*) seed or seedlings at the 2.0 to 3.5 leaf stage; seeds, tubers or plant parts selected from arrowhead (*Sagittaria rigida*), barnyardgrass (*Echinochloa crus-galli*), common arrowhead (*Sagittaria spp.*), common waterplantain (*Alisma plantago-aquatica*), ducksalad (*Heteranthera limosa*), early watergrass (*Echinochloa oryzoides*), gooseweed (*Sphenoclea zeylanica*), junglerice (*Echinochloa colonum*), late watergrass (*Echinochloa oryzicola*), monochoria (*Monochoria vaginalis*), pondweed species (*Potamogeton spp.*), redstem (*Aremania species*), rice flatsedge (*Cyperus iria*), ricefield bulrush (*Scirpus mucronatus*), small flower flatsedge (*Cyperus difformis*), tighthead sprangletop (*Leptochloa fasicularis*), water-clover (*Marsilea quadrifolia*) and waterchestnut (*Eleocharis dulcis*), were planted into this soil. Plantings and waterings of these crops and weed species were adjusted to produce plants of appropriate size for the test. At the two leaf stage, water levels were raised to 3 cm above the soil surface and maintained at this level throughout the test. Chemical treatments were formulated in a non-phytotoxic solvent mixture which includes a surfactant and applied directly to the paddy water, by pipette, or to the plant foliage, by an air-pressure assisted, calibrated belt-conveyer spray system.

Treated plants and controls were maintained in a greenhouse for approximately 21 days, after which all species were compared to controls and visually evaluated. Plant response ratings, summarized in Table C, are reported on a 0 to 100 scale where 0 is no effect and 100 is complete control. A dash (–) response means no test result.

TABLE C

COMPOUND
Paddy with silt loam soil

| Rate 500 g/ha | 20 | Rate 375 g/ha | 19 | 20 |
|---|---|---|---|---|
| barnyardgrass | — | barnyardgrass | 85 | — |
| ducksalad | 60 | ducksalad | 95 | 35 |
| early watergras | — | early watergras | 40 | — |
| late watergrass | — | late watergrass | 60 | — |
| redstem | 95 | redstem | 95 | 95 |
| rice flatsedge | 100 | rice flatsedge | 95 | 95 |
| smallflower fla | 95 | smallflower fla | 95 | 95 |
| tighthead spran | 100 | tighthead spran | 100 | 35 |
| 2 LF direct see | 50 | 2 LF direct see | 55 | 45 |
| 2 LF transp. in | 50 | 2 LF transp. in | 45 | 45 |

| Rate 250 g/ha | 19 | 20 | Rate 125 g/ha | 19 | 20 |
|---|---|---|---|---|---|
| barnyardgrass | 80 | — | barnyardgrass | 60 | — |
| ducksalad | 95 | 35 | ducksalad | 80 | 30 |
| early watergras | 40 | — | early watergras | 30 | — |
| late watergrass | 65 | — | late watergrass | 70 | — |
| redstem | 95 | 100 | redstem | 100 | 90 |
| rice flatsedge | 90 | 90 | rice flatsedge | 90 | 0 |
| smallflower fla | 100 | 95 | smallflower fla | 90 | 85 |
| tighthead spran | 100 | 40 | tighthead spran | 95 | 0 |
| 2 LF direct see | 55 | 45 | 2 LF direct see | 50 | 35 |
| | | | 2 LF transp. in | 40 | 35 |

| Rate 64 g/ha | 19 | 20 | Rate 32 g/ha | 19 |
|---|---|---|---|---|
| barnyardgrass | 15 | — | barnyardgrass | 10 |
| ducksalad | 85 | 0 | ducksalad | 60 |
| early watergras | 10 | — | early watergras | 10 |
| late watergrass | 0 | — | late watergrass | 10 |
| redstem | 90 | 80 | redstem | 40 |
| rice flatsedge | 95 | 55 | rice flatsedge | 85 |
| smallflower fla | 85 | 20 | smallflower fla | 30 |
| tighthead spran | 60 | 0 | tighthead spran | 60 |
| 2 LF direct see | 40 | 15 | 2 LF direct see | 35 |
| 2 LF transp. in | 35 | 15 | 2 LF transp. in | 25 |

TEST D

Compounds evaluated in this test were formulated in a non-phytotoxic solvent mixture and applied to the surface of the water which was contained in each pot. Individual containers of barnyardgrass (*Echinochloa oryzicola*), small flower umbrella sedge (*Cyperus difformus*), common falsepimpernel (*Lindernia procurebens*), monochoria (*Monochoria vaginalis*) and bulrush (*Scirpus juncoides*) were seeded and allowed to grow until the 1.5 to 2.5 leaf stage of development. A Sultama clay loam soil was used for this propagation. Japonica rice (*Oryza sativa*) was transplanted at 0 and 2 cm depth five days before application of the test compound to the water surface. An early and late stage of each weed species was treated, the stage of development being related to the concurrent planting of Scirpus juncoides which was then treated at the 1.5 (early) and the 2.5 (late) leaf stage.

Treated plants and untreated controls were maintained under greenhouse conditions for twenty to thirty days at which time treated plants were compared to untreated controls and visually evaluated. Plant response ratings, summarized in Table D, are based upon a 0 to 100 scale where 0 is no effect and 100 is complete control. A dash response (–) indicated that no test result was recorded.

TABLE D

| | COMPOUND | | COMPOUND | | |
|---|---|---|---|---|---|
| Rate 1000 g/ha | 35 | Rate 500 g/ha | 24 | 26 | 35 |
| Flood Saita soil | | Flood Saita soil | | | |
| barnyard early | 55 | barnyard early | 55 | 60 | 50 |
| barnyard late | 50 | barnyard late | 45 | 40 | 40 |
| *C. difformis* ea | 100 | *C. difformis* ea | 90 | 100 | 100 |
| *C. difformis* la | 100 | *C. difformis* la | 60 | 75 | 100 |
| Japoni rice 0 cm | 60 | Japoni rice 0 cm | 75 | 30 | 35 |
| Japoni rice 2 cm | 0 | Japoni rice 2 cm | 30 | 25 | 0 |
| *L. procumben* ea | 70 | *L. procumben* ea | 100 | 40 | 75 |
| *L. procumben* la | — | *L. procumben* la | 100 | 40 | 65 |
| *M. vaginalis* ea | 35 | *M. vaginalis* ea | 90 | 60 | 30 |
| *M. vaginalis* la | 40 | *M. vaginalis* la | 70 | 45 | 40 |
| *S. juncoides* 1. | 70 | *S. juncoides* 1. | 70 | 55 | 60 |
| *S. juncoides* 2. | 60 | *S. juncoides* 2. | 55 | 40 | 40 |

TABLE D

COMPOUND
Flood Saita soil

| Rate 250 g/ha | 19 | 20 | 24 | 26 | 35 | Rate 125 g/ha | 19 | 20 | 24 | 26 | 35 |
|---|---|---|---|---|---|---|---|---|---|---|---|
| barnyard early | 95 | 50 | 45 | 45 | 45 | barnyard early | 80 | 30 | 40 | 30 | 20 |
| barnyard late | 50 | 35 | 45 | 40 | 30 | barnyard late | 30 | 35 | 20 | 10 | 30 |

TABLE D-continued

| COMPOUND Flood Saita soil | | | | | | | | | | | |
|---|---|---|---|---|---|---|---|---|---|---|---|
| *C. difformis* ea | 80 | 80 | 85 | 80 | 100 | *C. difformis* ea | 70 | 85 | 95 | 65 | 90 |
| *C. difformis* la | 85 | 100 | 60 | 50 | 100 | *C. difformis* la | 75 | 100 | 65 | 35 | 100 |
| Japoni rice 0 cm | — | 80 | 70 | 30 | 45 | Japoni rice 0 cm | 80 | 80 | 55 | 5 | 40 |
| Japoni rice 2 cm | — | 25 | 25 | 20 | 0 | Japoni rice 2 cm | 25 | 5 | 20 | 15 | 5 |
| *L. procumben* ea | 100 | 80 | 100 | 70 | 65 | *L. procumben* ea | 100 | 90 | 100 | 0 | 40 |
| *L. procumben* la | 60 | 100 | 100 | 50 | 60 | *L. procumben* la | 65 | 70 | 95 | 30 | 20 |
| *M. vaginalis* ea | 100 | 80 | 85 | 80 | 40 | *M. vaginalis* ea | 100 | 70 | 95 | 60 | 20 |
| *M. vaginaiis* la | 50 | 55 | 65 | 60 | 20 | *M. vaginalis* la | 50 | 50 | 30 | 30 | 10 |
| *S. juncoides* 1. | 80 | 50 | 70 | 30 | 55 | *S. juncoides* 1. | 65 | 50 | 55 | 30 | 40 |
| *S. juncoides* 2. | 60 | 40 | 65 | 35 | 30 | *S. juncoides* 2. | 40 | 50 | 20 | 30 | 10 |
| Rate 64 g/ha | 19 | 20 | 24 | 26 | | Rate 32 g/ha | 19 | 20 | | | |
| barnyard early | 60 | 40 | 50 | 20 | | barnyard early | 50 | 30 | | | |
| barnyard late | 10 | 30 | 20 | 0 | | barnyard late | 10 | 10 | | | |
| *C. difformis* ea | 60 | 80 | — | 30 | | *C. difformis* ea | 60 | 80 | | | |
| *C. difformis* la | 65 | 75 | 50 | 30 | | *C. difformis* la | 40 | 0 | | | |
| Japoni rice 0 cm | 85 | 70 | 25 | 5 | | Japoni rice 0 cm | 70 | 50 | | | |
| Japoni rice 2 cm | 20 | 5 | 0 | 10 | | Japoni rice 2 cm | 10 | 5 | | | |
| *L. procumben* ea | 50 | 50 | 100 | — | | *L. procumben* ea | 50 | 30 | | | |
| *L. procumben* la | 20 | 65 | 100 | — | | *L. procumben* la | 20 | 0 | | | |
| *M. vaginalis* ea | 50 | 65 | 95 | 20 | | *M. vaginalis* ea | 50 | 80 | | | |
| *M. vaginalis* la | 30 | 55 | 40 | 30 | | *M. vaginalis* la | 30 | 10 | | | |
| *S. juncoides* 1. | 60 | 50 | 40 | 30 | | *S. juncoides* 1. | 60 | 40 | | | |
| *S. juncoides* 2. | 40 | 30 | 30 | 0 | | *S. juncoides* 2. | 0 | 10 | | | |

What is claimed is:

1. A compound selected from Formula I, N-oxides or agriculturally-suitable salts thereof,

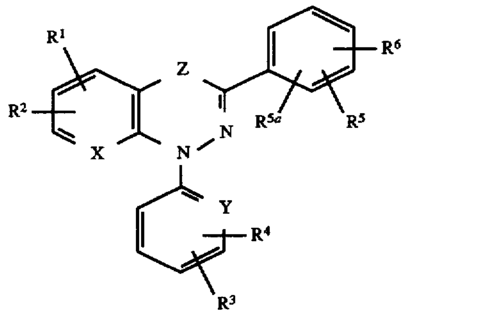

I wherein:

X and Y are independently N or CH;

Z is O;

$R^1$ and $R^2$ are independently H, halogen, cyano, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ haloalkylthio, $C_1$–$C_4$ alkylsulfinyl, or $C_1$–$C_4$ alkylsulfonyl;

$R^3$ is halogen, cyano, $SF_5$, $C_1$–$C_4$ haloalkyl, $C_1$–$C_4$ haloalkoxy, $C_1$–$C_4$ alkylthio, $C_1$–$C_4$ haloalkylthio, $C_1$–$C_4$ alkylsulfinyl, or $C_1$–$C_4$ alkylsulfonyl;

$R^4$ is H, halogen, cyano, $SF_5$, $C_1$–$C_4$ haloalkyl, $C_1$–$C_4$ haloalkoxy, $C_1$–$C_4$ alkylthio, $C_1$–$C_4$ haloalkylthio, $C_1$–$C_4$ alkylsulfinyl, or $C_1$–$C_4$ alkylsulfonyl; or when $R^3$ and $R^4$ are attached to adjacent atoms, $R^3$ and $R^4$ can be taken together as $—OCH_2O—$ or $—OCH_2CH_2O—$; each $CH_2$ group of said taken together $R^3$ and $R^4$ optionally substituted with 1–2 fluorine atoms;

$R^5$ is H, halogen, cyano, $SF_5$, $C_1$–$C_4$ alkyl, $C_1$–$C_4$ haloalkyl, $C_1$–$C_4$ alkoxy, $C_1$–$C_4$ haloalkoxy, $C_3$–$C_4$ alkenyloxy, $C_3$–$C_4$ haloalkenyloxy, $C_3$–$C_4$ alkynyloxy, $C_3$–$C_4$ haloalkynyloxy, $C_1$–$C_4$ alkylthio, $C_1$–$C_4$ haloalkylthio, $C_1$–$C_4$ alkylsulfinyl, or $C_1$–$C_4$ alkylsulfonyl;

$R^{5a}$ is H or halogen; and $R^6$ is halogen, cyano, $SF_5$, $C_1$–$C_4$ alkyl, $C_1$–$C_4$ haloalkyl, $C_1$–$C_4$ alkoxy, $C_1$–$C_4$ haloalkoxy, $C_3$–$C_4$ alkenyloxy, $C_3$–$C_4$ haloalkenyloxy, $C_3$–$C_4$ alkynyloxy, $C_3$–$C_4$ haloalkynyloxy, $C_1$–$C_4$ alkylthio, $C_1$–$C_4$ haloalkylthio, $C_1$–$C_4$ alkylsulfinyl, or $C_1$–$C_4$ alkylsulfonyl.

2. A compound of claim 1 wherein:

X and Y are N;

Z is O;

$R^3$ is halogen, $C_1$–$C_4$ haloalkyl, or $C_1$–$C_4$ haloalkoxy;

$R^4$ is H, halogen, $C_1$–$C_4$ haloalkyl, or $C_1$–$C_4$ haloalkoxy; or when $R^3$ and $R^4$ are attached to adjacent atoms, $R^3$ and $R^4$ can be taken together as $—OCH_2O—$ or $—OCH_2CH_2O—$; each $CH_2$ group of said taken together $R^3$ and $R^4$ optionally substituted with 1–2 fluorine atoms.

3. A compound of claim 2 wherein:

$R^1$ and $R^2$ are independently H, halogen, $C_1$–$C_4$ alkyl, $C_1$–$C_4$ haloalkyl, or $C_1$–$C_4$ haloalkoxy;

$R^5$ is H, halogen, $C_1$–$C_4$ alkyl, $C_1$–$C_4$ haloalkyl, or $C_1$–$C_4$ haloalkoxy; and $R^6$ is halogen, $C_1$–$C_4$ alkyl, $C_1$–$C_4$ haloalkyl, or $C_1$–$C_4$ haloalkoxy.

4. The compound of claim 1 which is selected from the group:

a) 3-(4-fluorophenyl)-1-[6-(trifluoromethyl)-2-pyridinyl]-1H-pyrido[2,3-e][1,3,4]oxadiazine;

b) 3-(3,4-difluorophenyl)-6-fluoro-1-[6-(trifluoromethyl)-2-pyridinyl]-1H-pyrido[2,3-e][1,3,4]oxadiazine;

c) 6-fluoro-3-(4-fluorophenyl)-1-[3-(trifluoromethyl)phenyl]-1H-pyrido[2,3-e][1,3,4]oxadiazine;

d) 6-fluoro-3-[2-fluoro-4-(trifluoromethyl)phenyl]-1-[6-(trifluoromethyl)-2-pyridinyl]-1H-pyrido[2,3-e][1,3,4]oxadiazine; and e) 6-fluoro-3-(4-fluorophenyl)-1-[3-(trifluoromethoxy)phenyl]-1H-pyrido[2,3-e][1,3,4]oxadiazine.

5. A herbicidal composition comprising a herbicidally effective amount of a compound of claim 1 and at least one of a surfactant, a solid diluent or a liquid diluent.

6. A herbicidal composition comprising a herbicidally effective amount of a compound of claim 2 and at least one of a surfactant, a solid diluent or a liquid diluent.

7. A herbicidal composition comprising a herbicidally effective amount of a compound of claim 3 and at least one of a surfactant, a solid diluent or a liquid diluent.

8. A herbicidal composition comprising a herbicidally effective amount of a compound of claim 4 and at least one of a surfactant, a solid diluent or a liquid diluent.

9. A method for controlling the growth of undesired vegetation comprising contacting the vegetation or its environment with a herbicidally effective amount of a compound of claim 1.

* * * * *